United States Patent
Abdou

(10) Patent No.: US 10,973,648 B1
(45) Date of Patent: Apr. 13, 2021

(54) DEVICES AND METHODS FOR VERTEBRAL BONE REALIGNMENT

(71) Applicant: Samy Abdou, San Diego, CA (US)

(72) Inventor: Samy Abdou, San Diego, CA (US)

( * ) Notice: Subject to any disclaimer, the term of this patent is extended or adjusted under 35 U.S.C. 154(b) by 0 days.

(21) Appl. No.: 16/780,815

(22) Filed: Feb. 3, 2020

Related U.S. Application Data

(63) Continuation-in-part of application No. 15/793,895, filed on Oct. 25, 2017.
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/4425* (2013.01); *A61F 2/4455* (2013.01); *A61F 2002/3055* (2013.01);
(Continued)

(58) Field of Classification Search
CPC ...... A61F 2/4455; A61F 2/3868; A61F 2/442; A61F 2/385; A61F 2/447; A61F 2/4465; A61F 2/4611; A61F 2002/2835; A61F 2002/304; A61F 2002/3052; A61F 2002/3055; A61F 2002/3084;
(Continued)

(56) References Cited

U.S. PATENT DOCUMENTS

| 167,625 A | 9/1875 | Charles |
|---|---|---|
| 203,512 A | 5/1878 | Nicholas |

(Continued)

FOREIGN PATENT DOCUMENTS

| DE | 3114872 A1 | 10/1982 |
|---|---|---|
| DE | 3741493 A1 | 6/1989 |

(Continued)

OTHER PUBLICATIONS

Abdou, Variable-Shaped, Expandable Device and Method for Minimally-Invasive Use, Mar. 28, 2011, U.S. Appl. No. 13/073,860.
(Continued)

*Primary Examiner* — Pedro Philogene
(74) *Attorney, Agent, or Firm* — Gazdzinski & Associates, PC

(57) ABSTRACT

Methods and apparatus for providing correction of one or more maladies or conditions of the spinal column of a living being. In one embodiment, the apparatus includes an implantable device configured to be selectively adjustable in one or more portions thereof so as to permit correction of asymmetries or irregularities of the spinal column via insertion into one or more affected intervertebral disc spaces. In one variant, the implantable device includes upper and lower host elements which are hinged or can pivot relative to one another, and an insertable distraction mechanism which is adjustable to enable one side or the other of the implantable device to alter height. In another variant, both sides of the implantable device can be adjusted for height via the host elements and one or more pivots or hinges. In one implementation, the distraction mechanism is adjustable from multiple approaches into the disc space.

36 Claims, 32 Drawing Sheets

Related U.S. Application Data

(60) Provisional application No. 62/496,721, filed on Oct. 25, 2016.

(52) U.S. Cl.
CPC ............... *A61F 2002/30538* (2013.01); *A61F 2002/30624* (2013.01); *A61F 2002/443* (2013.01); *A61F 2002/444* (2013.01)

(58) Field of Classification Search
CPC .... A61F 2002/3093; A61F 2002/30331; A61F 2002/30365; A61F 2002/30383; A61F 2002/30398; A61F 2002/30401; A61F 2002/30405; A61F 2002/30444; A61F 2002/30471; A61F 2002/30504; A61F 2002/30523; A61F 2002/30525; A61F 2002/30538; A61F 2002/30556; A61F 2002/30579; A61F 2002/30594; A61F 2002/30596; A61F 2002/30598; A61F 2002/30601; A61F 2002/30604; A61F 2002/30607; A61F 2002/30616; A61F 2002/30626; A61F 2002/30632; A61F 2002/30785; A61F 2002/30904; A61F 2002/4475; A61F 2310/00017; A61F 2310/00023; A61F 2310/00359
USPC ............................................ 623/17.11–17.16
See application file for complete search history.

(56) References Cited

U.S. PATENT DOCUMENTS

| | | |
|---|---|---|
| 203,624 A | 5/1878 | Josias |
| 229,347 A | 6/1880 | Shepherd |
| 267,269 A | 11/1882 | John |
| 824,983 A | 7/1906 | Charles |
| 944,725 A | 12/1909 | Ferguson, Jr. |
| 1,015,890 A | 1/1912 | Hyde |
| 1,156,440 A | 10/1915 | Smith |
| 1,213,599 A | 1/1917 | Dow |
| 1,785,709 A | 12/1930 | Harry et al. |
| 2,248,054 A | 7/1941 | Becker |
| 2,329,398 A | 9/1943 | Duffy |
| 2,370,407 A | 2/1945 | McCartney |
| 2,574,352 A | 11/1951 | Senter |
| 2,677,369 A | 5/1954 | Knowles |
| 2,774,350 A | 12/1956 | Cleveland, Jr. et al. |
| 3,025,853 A | 3/1962 | Mason |
| 3,037,596 A | 6/1962 | Fordyce |
| 3,072,423 A | 1/1963 | Charlton |
| 3,073,584 A | 1/1963 | Henry et al. |
| 3,090,386 A | 5/1963 | William et al. |
| 3,236,141 A | 2/1966 | Smith |
| 3,242,922 A | 3/1966 | Thomas |
| 3,260,412 A | 7/1966 | Larkin |
| 3,277,555 A | 10/1966 | Kutash |
| 3,374,786 A | 3/1968 | Callender, Jr. et al. |
| 3,383,769 A | 5/1968 | Davis |
| 3,384,077 A | 5/1968 | Gauthier |
| 3,426,364 A | 2/1969 | Lumb et al. |
| 3,604,487 A | 9/1971 | Richard |
| 3,648,691 A | 3/1972 | Lumb et al. |
| 3,659,595 A | 5/1972 | Edward |
| 3,695,259 A | 10/1972 | Yost et al. |
| 3,708,883 A | 1/1973 | Flander et al. |
| 3,741,205 A | 6/1973 | Markolf et al. |
| 3,749,088 A | 7/1973 | Kohlmann et al. |
| 3,791,380 A | 2/1974 | Dawidowski et al. |
| 3,795,981 A | 3/1974 | Franklin et al. |
| 3,805,219 A | 4/1974 | Bright et al. |
| 3,825,992 A | 7/1974 | Troeger et al. |
| 3,858,578 A | 1/1975 | Milo |
| 3,865,105 A | 2/1975 | Lode |
| 3,867,728 A | 2/1975 | Stubstad et al. |
| 3,892,232 A | 7/1975 | Neufeld |
| 3,965,890 A | 6/1976 | Gauthier |
| 4,009,712 A | 3/1977 | Burstein et al. |
| 4,037,592 A | 7/1977 | Kronner |
| 4,047,524 A | 9/1977 | Hall |
| 4,074,542 A | 2/1978 | Hankosky et al. |
| 4,135,506 A | 1/1979 | Ulrich |
| 4,143,883 A | 3/1979 | Paynter |
| 4,165,746 A | 8/1979 | Burgin |
| 4,175,555 A | 11/1979 | Herbert |
| 4,237,875 A | 12/1980 | Termanini |
| 4,254,763 A | 3/1981 | McCready et al. |
| 4,289,123 A | 9/1981 | Dunn |
| 4,309,777 A | 1/1982 | Patil |
| 4,349,921 A | 9/1982 | Kuntz et al. |
| 4,399,813 A | 8/1983 | Barber |
| 4,409,974 A | 10/1983 | Freedland |
| 4,432,358 A | 2/1984 | Fixel |
| 4,448,181 A | 5/1984 | Ishikawa et al. |
| 4,448,191 A | 5/1984 | Rodnyansky et al. |
| 4,488,543 A | 12/1984 | Tornier |
| 4,493,317 A | 1/1985 | Klaue |
| 4,494,535 A | 1/1985 | Haig |
| 4,503,848 A | 3/1985 | Caspar et al. |
| 4,545,374 A | 10/1985 | Jacobson et al. |
| 4,554,914 A | 11/1985 | Kapp et al. |
| 4,561,432 A | 12/1985 | Mazor |
| 4,569,662 A | 2/1986 | Dragan |
| 4,570,618 A | 2/1986 | Wu |
| 4,580,563 A | 4/1986 | Gross |
| 4,604,995 A | 8/1986 | Stephens et al. |
| 4,611,581 A | 9/1986 | Steffee |
| 4,611,582 A | 9/1986 | Duff |
| 4,612,920 A | 9/1986 | Lower |
| 4,632,101 A | 12/1986 | Freedland |
| 4,636,217 A | 1/1987 | Ogilvie et al. |
| 4,653,481 A | 3/1987 | Howland et al. |
| 4,655,462 A | 4/1987 | Balsells |
| 4,655,629 A | 4/1987 | Flaherty |
| 4,655,778 A | 4/1987 | Koeneman |
| 4,664,305 A | 5/1987 | Blake, III et al. |
| 4,697,582 A | 10/1987 | William |
| 4,699,076 A | 10/1987 | Curtis et al. |
| 4,702,230 A | 10/1987 | Pelta |
| 4,711,232 A | 12/1987 | Fischer et al. |
| 4,714,469 A | 12/1987 | Kenna |
| 4,722,331 A | 2/1988 | Fox |
| 4,747,394 A | 5/1988 | Watanabe |
| 4,747,395 A | 5/1988 | Brief |
| 4,756,711 A | 7/1988 | Mai et al. |
| 4,759,766 A | 7/1988 | Buettner-Janz et al. |
| 4,759,769 A | 7/1988 | Hedman et al. |
| 4,773,402 A | 9/1988 | Asher et al. |
| 4,787,908 A | 11/1988 | Wyss et al. |
| 4,790,303 A | 12/1988 | Steffee |
| 4,791,918 A | 12/1988 | Von |
| 4,794,918 A | 1/1989 | Wolter |
| 4,820,305 A | 4/1989 | Harms et al. |
| 4,834,757 A | 5/1989 | Brantigan |
| 4,867,404 A | 9/1989 | Harrington et al. |
| 4,874,389 A | 10/1989 | Downey |
| 4,877,020 A | 10/1989 | Vich |
| 4,881,525 A | 11/1989 | Williams |
| 4,887,595 A | 12/1989 | Heinig et al. |
| 4,898,156 A | 2/1990 | Gatturna et al. |
| 4,899,761 A | 2/1990 | Brown et al. |
| 4,903,692 A | 2/1990 | Reese |
| 4,904,110 A | 2/1990 | Klein |
| 4,907,577 A | 3/1990 | Wu |
| 4,911,718 A | 3/1990 | Lee et al. |
| 4,913,134 A | 4/1990 | Luque |
| 4,932,975 A | 6/1990 | Main et al. |
| 4,934,352 A | 6/1990 | Sullivan, Jr. |
| 4,938,769 A | 7/1990 | Shaw |
| 4,944,757 A | 7/1990 | Martinez et al. |
| 4,946,378 A | 8/1990 | Hirayama et al. |
| 4,946,468 A | 8/1990 | Li |
| 4,949,707 A | 8/1990 | Levahn et al. |

(56) References Cited

U.S. PATENT DOCUMENTS

| | | |
|---|---|---|
| 4,955,908 A | 9/1990 | Frey et al. |
| 4,957,495 A | 9/1990 | Kluger |
| 4,957,497 A | 9/1990 | Hoogland et al. |
| 4,961,740 A | 10/1990 | Ray et al. |
| 4,963,152 A | 10/1990 | Hofmann et al. |
| 4,964,403 A | 10/1990 | Karas et al. |
| 4,969,886 A | 11/1990 | Cziffer et al. |
| 4,969,887 A | 11/1990 | Sodhi |
| 4,973,332 A | 11/1990 | Kummer |
| 4,997,123 A | 3/1991 | Backus et al. |
| 4,997,432 A | 3/1991 | Keller |
| 5,002,550 A | 3/1991 | Li |
| 5,002,576 A | 3/1991 | Fuhrmann et al. |
| 5,007,880 A | 4/1991 | Walker |
| 5,007,910 A | 4/1991 | Anapliotis et al. |
| 5,011,484 A | 4/1991 | Breard |
| 5,015,247 A | 5/1991 | Michelson |
| 5,026,373 A | 6/1991 | Ray et al. |
| 5,052,711 A | 10/1991 | Pirkey et al. |
| 5,055,104 A | 10/1991 | Ray |
| 5,061,271 A | 10/1991 | Van |
| 5,071,437 A | 12/1991 | Steffee |
| 5,084,049 A | 1/1992 | Asher et al. |
| 5,087,266 A | 2/1992 | Connell et al. |
| 5,092,866 A | 3/1992 | Breard et al. |
| 5,092,893 A | 3/1992 | Smith |
| 5,098,435 A | 3/1992 | Stednitz et al. |
| 5,116,336 A | 5/1992 | Frigg |
| 5,122,130 A | 6/1992 | Keller |
| 5,122,131 A | 6/1992 | Tsou |
| 5,127,914 A | 7/1992 | Calderale et al. |
| 5,129,899 A | 7/1992 | Small et al. |
| 5,131,904 A | 7/1992 | Markoll |
| 5,133,717 A | 7/1992 | Chopin |
| 5,147,360 A | 9/1992 | Dubousset |
| 5,147,361 A | 9/1992 | Ojima et al. |
| 5,152,303 A | 10/1992 | Allen |
| 5,167,662 A | 12/1992 | Hayes et al. |
| 5,176,680 A | 1/1993 | Vignaud et al. |
| 5,180,381 A | 1/1993 | Aust et al. |
| 5,180,393 A | 1/1993 | Commarmond |
| 5,192,327 A | 3/1993 | Brantigan |
| 5,207,679 A | 5/1993 | Li |
| 5,222,954 A | 6/1993 | Baker et al. |
| 5,226,766 A | 7/1993 | Lasner |
| 5,234,431 A | 8/1993 | Keller |
| 5,234,432 A | 8/1993 | Brown |
| 5,234,447 A | 8/1993 | Kaster et al. |
| 5,236,460 A | 8/1993 | Barber |
| 5,242,444 A | 9/1993 | MacMillan |
| 5,242,445 A | 9/1993 | Ashman |
| 5,246,442 A | 9/1993 | Ashman et al. |
| 5,246,458 A | 9/1993 | Graham |
| 5,250,055 A | 10/1993 | Moore et al. |
| 5,252,016 A | 10/1993 | Schmid et al. |
| 5,254,118 A | 10/1993 | Mirkovic |
| 5,258,031 A | 11/1993 | Salib et al. |
| 5,261,907 A | 11/1993 | Vignaud et al. |
| 5,261,909 A | 11/1993 | Sutterlin et al. |
| 5,261,910 A | 11/1993 | Warden et al. |
| 5,261,911 A | 11/1993 | Carl |
| 5,261,914 A | 11/1993 | Warren |
| 5,275,600 A | 1/1994 | Allard et al. |
| 5,275,601 A | 1/1994 | Gogolewski et al. |
| 5,281,222 A | 1/1994 | Allard et al. |
| 5,282,801 A | 2/1994 | Sherman |
| 5,282,862 A | 2/1994 | Baker et al. |
| 5,290,312 A | 3/1994 | Kojimoto et al. |
| 5,300,074 A | 4/1994 | Frigg |
| 5,304,178 A | 4/1994 | Stahurski |
| 5,306,307 A | 4/1994 | Senter et al. |
| 5,312,405 A | 5/1994 | Korotko et al. |
| 5,324,290 A | 6/1994 | Zdeblick et al. |
| 5,324,292 A | 6/1994 | Meyers |
| 5,330,468 A | 7/1994 | Burkhart |
| 5,330,473 A | 7/1994 | Howland |
| 5,334,205 A | 8/1994 | Cain |
| 5,335,418 A | 8/1994 | Krivec |
| 5,336,225 A | 8/1994 | Zang |
| 5,336,226 A | 8/1994 | McDaniel et al. |
| 5,342,394 A | 8/1994 | Matsuno et al. |
| 5,344,421 A | 9/1994 | Crook |
| 5,344,422 A | 9/1994 | Frigg |
| 5,346,493 A | 9/1994 | Stahurski et al. |
| 5,350,380 A | 9/1994 | Goble et al. |
| 5,352,226 A | 10/1994 | Lin |
| 5,352,231 A | 10/1994 | Brumfield et al. |
| 5,354,292 A | 10/1994 | Braeuer et al. |
| 5,356,410 A | 10/1994 | Pennig |
| 5,358,289 A | 10/1994 | Banker et al. |
| 5,360,429 A | 11/1994 | Jeanson et al. |
| 5,360,431 A | 11/1994 | Puno et al. |
| 5,361,766 A | 11/1994 | Nichols et al. |
| 5,364,399 A | 11/1994 | Lowery et al. |
| 5,366,455 A | 11/1994 | Dove et al. |
| 5,370,697 A | 12/1994 | Baumgartner |
| 5,372,599 A | 12/1994 | Martins |
| 5,374,267 A | 12/1994 | Siegal |
| 5,375,823 A | 12/1994 | Navas |
| 5,380,324 A | 1/1995 | Mueller et al. |
| 5,385,583 A | 1/1995 | Cotrel |
| 5,387,176 A | 2/1995 | Markoll |
| 5,387,213 A | 2/1995 | Breard et al. |
| 5,395,371 A | 3/1995 | Miller et al. |
| 5,397,363 A | 3/1995 | Gelbard |
| 5,397,364 A | 3/1995 | Kozak et al. |
| 5,403,316 A | 4/1995 | Ashman |
| 5,413,576 A | 5/1995 | Rivard |
| 5,415,661 A | 5/1995 | Holmes |
| 5,417,712 A | 5/1995 | Whittaker et al. |
| 5,423,816 A | 6/1995 | Lin |
| 5,423,818 A | 6/1995 | Van et al. |
| 5,423,819 A | 6/1995 | Small et al. |
| 5,423,826 A | 6/1995 | Coates et al. |
| 5,425,772 A | 6/1995 | Brantigan |
| 5,425,773 A | 6/1995 | Boyd et al. |
| 5,427,418 A | 6/1995 | Watts |
| 5,429,639 A | 7/1995 | Judet |
| 5,431,658 A | 7/1995 | Moskovich |
| 5,437,669 A | 8/1995 | Yuan et al. |
| 5,437,670 A | 8/1995 | Sherman et al. |
| 5,437,672 A | 8/1995 | Alleyne |
| 5,437,674 A | 8/1995 | Worcel et al. |
| 5,439,339 A | 8/1995 | Batchelor |
| 5,439,463 A | 8/1995 | Lin |
| 5,443,467 A | 8/1995 | Biedermann et al. |
| 5,443,514 A | 8/1995 | Steffee |
| 5,449,257 A | 9/1995 | Giannuzzi |
| 5,453,073 A | 9/1995 | Markoll |
| 5,456,714 A | 10/1995 | Owen |
| 5,458,638 A | 10/1995 | Kuslich et al. |
| 5,466,237 A | 11/1995 | Byrd, III et al. |
| 5,468,241 A | 11/1995 | Metz-Stavenhagen et al. |
| 5,472,452 A | 12/1995 | Trott |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,478,342 A | 12/1995 | Kohrs |
| 5,480,401 A | 1/1996 | Navas |
| 5,484,437 A | 1/1996 | Michelson |
| 5,484,440 A | 1/1996 | Allard |
| 5,486,174 A | 1/1996 | Fournet-Fayard et al. |
| 5,486,176 A | 1/1996 | Hildebrand et al. |
| 5,487,742 A | 1/1996 | Cotrel |
| 5,489,307 A | 2/1996 | Kuslich et al. |
| 5,489,308 A | 2/1996 | Kuslich et al. |
| 5,490,750 A | 2/1996 | Gundy |
| 5,496,318 A | 3/1996 | Howland et al. |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,507,754 A | 4/1996 | Green et al. |

(56) References Cited

U.S. PATENT DOCUMENTS

| | | |
|---|---|---|
| 5,507,816 A | 4/1996 | Bullivant |
| 5,512,038 A | 4/1996 | O'Neal et al. |
| 5,514,180 A | 5/1996 | Heggeness et al. |
| 5,520,690 A | 5/1996 | Errico et al. |
| 5,522,899 A | 6/1996 | Michelson |
| 5,527,314 A | 6/1996 | Brumfield et al. |
| 5,531,747 A | 7/1996 | Ray |
| 5,531,751 A | 7/1996 | Schultheiss et al. |
| 5,534,001 A | 7/1996 | Schlapfer et al. |
| 5,534,002 A | 7/1996 | Brumfield et al. |
| 5,534,027 A | 7/1996 | Hodorek |
| 5,540,688 A | 7/1996 | Navas |
| 5,545,163 A | 8/1996 | Miller et al. |
| 5,545,164 A | 8/1996 | Howland |
| 5,545,165 A | 8/1996 | Harms et al. |
| 5,545,179 A | 8/1996 | Williamson, IV |
| 5,549,607 A | 8/1996 | Olson et al. |
| 5,549,612 A | 8/1996 | Yapp et al. |
| 5,554,157 A | 9/1996 | Errico et al. |
| 5,556,431 A | 9/1996 | Buettner-Janz |
| 5,558,674 A | 9/1996 | Heggeness et al. |
| 5,562,660 A | 10/1996 | Grob |
| 5,562,661 A | 10/1996 | Yoshimi et al. |
| 5,562,662 A | 10/1996 | Brumfield et al. |
| 5,562,663 A | 10/1996 | Wisnewski et al. |
| 5,562,737 A | 10/1996 | Graf |
| 5,562,738 A | 10/1996 | Boyd et al. |
| 5,569,247 A | 10/1996 | Morrison |
| 5,569,248 A | 10/1996 | Mathews |
| 5,569,250 A | 10/1996 | Sarver et al. |
| 5,569,251 A | 10/1996 | Baker et al. |
| 5,569,252 A | 10/1996 | Justin et al. |
| 5,575,792 A | 11/1996 | Errico et al. |
| 5,578,033 A | 11/1996 | Errico et al. |
| 5,578,034 A | 11/1996 | Estes |
| 5,582,612 A | 12/1996 | Lin |
| 5,584,833 A | 12/1996 | Fournet-Fayard et al. |
| 5,584,834 A | 12/1996 | Errico et al. |
| 5,586,984 A | 12/1996 | Errico et al. |
| 5,591,166 A | 1/1997 | Bernhardt et al. |
| 5,599,279 A | 2/1997 | Slotman et al. |
| 5,601,553 A | 2/1997 | Trebing et al. |
| 5,603,714 A | 2/1997 | Kaneda et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,609,634 A | 3/1997 | Voydeville |
| 5,609,635 A | 3/1997 | Michelson |
| 5,609,636 A | 3/1997 | Kohrs et al. |
| 5,609,637 A | 3/1997 | Biedermann et al. |
| 5,611,800 A | 3/1997 | Davis et al. |
| 5,616,142 A | 4/1997 | Yuan et al. |
| 5,620,169 A | 4/1997 | Payne |
| 5,620,443 A | 4/1997 | Gertzbein et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schaefer et al. |
| 5,643,262 A | 7/1997 | Metz-Stavenhagen et al. |
| 5,643,321 A | 7/1997 | McDevitt |
| 5,645,544 A | 7/1997 | Tai et al. |
| 5,645,599 A | 7/1997 | Samani |
| 5,647,873 A | 7/1997 | Errico et al. |
| 5,649,931 A | 7/1997 | Bryant et al. |
| 5,653,763 A | 8/1997 | Errico et al. |
| 5,662,652 A | 9/1997 | Schaefer et al. |
| 5,662,653 A | 9/1997 | Songer et al. |
| 5,665,049 A | 9/1997 | Markoll |
| 5,667,513 A | 9/1997 | Torrie et al. |
| 5,669,868 A | 9/1997 | Markoll |
| 5,669,909 A | 9/1997 | Zdeblick et al. |
| 5,669,911 A | 9/1997 | Errico et al. |
| 5,669,912 A | 9/1997 | Spetzler |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,666 A | 10/1997 | Oxland et al. |
| 5,676,697 A | 10/1997 | McDonald |
| 5,676,701 A | 10/1997 | Yuan et al. |
| 5,676,703 A | 10/1997 | Gelbard |
| 5,681,311 A | 10/1997 | Foley et al. |
| 5,681,312 A | 10/1997 | Yuan et al. |
| 5,681,313 A | 10/1997 | Diez |
| 5,681,319 A | 10/1997 | Biedermann et al. |
| 5,683,390 A | 11/1997 | Metz-Stavenhagen et al. |
| 5,683,391 A | 11/1997 | Boyd |
| 5,683,392 A | 11/1997 | Richelsoph et al. |
| 5,683,394 A | 11/1997 | Rinner |
| 5,683,464 A | 11/1997 | Wagner et al. |
| 5,688,275 A | 11/1997 | Koros et al. |
| 5,690,630 A | 11/1997 | Errico et al. |
| 5,697,929 A | 12/1997 | Mellinger |
| 5,702,451 A | 12/1997 | Biedermann et al. |
| 5,704,936 A | 1/1998 | Mazel |
| 5,707,372 A | 1/1998 | Errico et al. |
| 5,709,686 A | 1/1998 | Talos et al. |
| 5,711,709 A | 1/1998 | McCoy |
| 5,713,672 A | 2/1998 | Lu |
| 5,713,898 A | 2/1998 | Stuecker et al. |
| 5,713,899 A | 2/1998 | Marnay et al. |
| 5,713,900 A | 2/1998 | Benzel et al. |
| 5,713,904 A | 2/1998 | Errico et al. |
| 5,716,356 A | 2/1998 | Biedermann et al. |
| 5,716,357 A | 2/1998 | Rogozinski |
| 5,720,751 A | 2/1998 | Jackson |
| 5,722,976 A | 3/1998 | Brown |
| 5,722,977 A | 3/1998 | Wilhelmy |
| 5,723,013 A | 3/1998 | Jeanson et al. |
| 5,725,527 A | 3/1998 | Biedermann et al. |
| 5,725,528 A | 3/1998 | Errico et al. |
| 5,725,582 A | 3/1998 | Bevan et al. |
| 5,728,046 A | 3/1998 | Mayer et al. |
| 5,728,098 A | 3/1998 | Sherman et al. |
| 5,733,284 A | 3/1998 | Martin |
| 5,733,285 A | 3/1998 | Errico et al. |
| 5,733,286 A | 3/1998 | Errico et al. |
| 5,733,290 A | 3/1998 | McCue et al. |
| 5,735,853 A | 4/1998 | Olerud |
| 5,738,685 A | 4/1998 | Halm et al. |
| 5,741,254 A | 4/1998 | Henry et al. |
| 5,741,261 A | 4/1998 | Moskovitz et al. |
| 5,746,743 A | 5/1998 | Greenberg |
| 5,749,916 A | 5/1998 | Richelsoph |
| 5,749,968 A | 5/1998 | Melanson et al. |
| 5,752,957 A | 5/1998 | Ralph et al. |
| 5,755,660 A | 5/1998 | Tyagi |
| 5,755,732 A | 5/1998 | Green et al. |
| 5,766,252 A | 6/1998 | Henry et al. |
| 5,772,583 A | 6/1998 | Wright et al. |
| 5,776,135 A | 7/1998 | Errico et al. |
| 5,776,199 A | 7/1998 | Michelson |
| 5,782,830 A | 7/1998 | Farris |
| 5,782,832 A | 7/1998 | Larsen et al. |
| 5,782,833 A | 7/1998 | Haider |
| 5,782,919 A | 7/1998 | Zdeblick et al. |
| 5,792,044 A | 8/1998 | Foley et al. |
| 5,795,289 A | 8/1998 | Wyttenbach |
| 5,795,291 A | 8/1998 | Koros et al. |
| 5,795,584 A | 8/1998 | Totakura et al. |
| 5,797,911 A | 8/1998 | Sherman et al. |
| 5,800,433 A | 9/1998 | Benzel et al. |
| 5,800,435 A | 9/1998 | Errico et al. |
| 5,800,547 A | 9/1998 | Schaefer et al. |
| 5,807,403 A | 9/1998 | Beyar et al. |
| 5,810,818 A | 9/1998 | Errico et al. |
| 5,810,819 A | 9/1998 | Errico et al. |
| 5,817,094 A | 10/1998 | Errico et al. |
| 5,833,418 A | 11/1998 | Shoji |
| 5,836,948 A | 11/1998 | Zucherman et al. |

(56) References Cited

U.S. PATENT DOCUMENTS

| | | |
|---|---|---|
| 5,842,966 A | 12/1998 | Markoll |
| 5,846,192 A | 12/1998 | Teixido |
| 5,860,977 A | 1/1999 | Zucherman et al. |
| 5,863,293 A | 1/1999 | Richelsoph |
| 5,865,848 A | 2/1999 | Baker |
| 5,873,878 A | 2/1999 | Harms et al. |
| 5,876,402 A | 3/1999 | Errico et al. |
| 5,876,404 A | 3/1999 | Zucherman et al. |
| 5,879,350 A | 3/1999 | Sherman et al. |
| 5,879,351 A | 3/1999 | Viart |
| 5,882,298 A | 3/1999 | Sharratt |
| 5,882,350 A | 3/1999 | Ralph et al. |
| 5,882,351 A | 3/1999 | Fox |
| 5,884,702 A | 3/1999 | Yokley et al. |
| 5,885,286 A | 3/1999 | Sherman et al. |
| 5,888,197 A | 3/1999 | Mulac et al. |
| 5,888,222 A | 3/1999 | Coates et al. |
| 5,888,224 A | 3/1999 | Beckers et al. |
| 5,888,226 A | 3/1999 | Rogozinski |
| 5,890,271 A | 4/1999 | Bromley et al. |
| 5,891,145 A | 4/1999 | Morrison et al. |
| 5,893,831 A | 4/1999 | Koros et al. |
| 5,899,425 A | 5/1999 | Corey, Jr. et al. |
| 5,899,904 A | 5/1999 | Errico et al. |
| 5,899,905 A | 5/1999 | Errico et al. |
| 5,902,231 A | 5/1999 | Foley et al. |
| 5,902,233 A | 5/1999 | Farley et al. |
| 5,902,304 A | 5/1999 | Walker et al. |
| 5,904,683 A | 5/1999 | Pohndorf et al. |
| RE36,221 E | 6/1999 | Breard et al. |
| 5,908,382 A | 6/1999 | Koros et al. |
| 5,910,141 A | 6/1999 | Morrison et al. |
| 5,928,139 A | 7/1999 | Koros et al. |
| 5,928,231 A | 7/1999 | Klein et al. |
| 5,928,233 A | 7/1999 | Apfelbaum et al. |
| 5,931,777 A | 8/1999 | Sava |
| 5,938,663 A | 8/1999 | Petreto |
| 5,941,885 A | 8/1999 | Jackson |
| 5,944,465 A | 8/1999 | Janitzki |
| 5,944,658 A | 8/1999 | Koros et al. |
| 5,947,967 A | 9/1999 | Barker |
| 5,947,970 A | 9/1999 | Schmelzeisen et al. |
| 5,951,553 A | 9/1999 | Betz et al. |
| 5,951,558 A | 9/1999 | Fiz |
| 5,954,722 A | 9/1999 | Bono |
| 5,954,725 A | 9/1999 | Sherman et al. |
| 5,961,516 A | 10/1999 | Graf |
| 5,961,517 A | 10/1999 | Biedermann et al. |
| 5,961,518 A | 10/1999 | Errico et al. |
| 5,964,760 A | 10/1999 | Richelsoph |
| 5,964,762 A | 10/1999 | Biedermann et al. |
| 5,964,763 A | 10/1999 | Incavo et al. |
| 5,967,970 A | 10/1999 | Cowan et al. |
| 5,967,972 A | 10/1999 | Santilli et al. |
| 5,971,987 A | 10/1999 | Huxel et al. |
| 5,976,135 A | 11/1999 | Sherman et al. |
| 5,976,140 A | 11/1999 | Haas |
| 5,976,146 A | 11/1999 | Ogawa et al. |
| 5,976,186 A | 11/1999 | Bao et al. |
| 5,980,522 A | 11/1999 | Koros et al. |
| 5,984,865 A | 11/1999 | Farley et al. |
| 5,984,923 A | 11/1999 | Breard |
| 5,984,967 A | 11/1999 | Zdeblick et al. |
| 5,993,385 A | 11/1999 | Johnston et al. |
| 5,993,449 A | 11/1999 | Schlaepfer et al. |
| 5,997,539 A | 12/1999 | Errico et al. |
| 6,001,098 A | 12/1999 | Metz-Stavenhagen et al. |
| 6,001,130 A | 12/1999 | Bryan et al. |
| 6,004,326 A | 12/1999 | Castro et al. |
| 6,004,349 A | 12/1999 | Jackson |
| 6,010,503 A | 1/2000 | Richelsoph et al. |
| 6,010,692 A | 1/2000 | Goldberg et al. |
| 6,016,727 A | 1/2000 | Morgan |
| 6,017,342 A | 1/2000 | Rinner |
| 6,017,344 A | 1/2000 | Errico et al. |
| 6,019,759 A | 2/2000 | Rogozinski |
| 6,019,792 A | 2/2000 | Cauthen |
| 6,022,350 A | 2/2000 | Ganem |
| 6,022,376 A | 2/2000 | Assell et al. |
| 6,030,388 A | 2/2000 | Yoshimi et al. |
| 6,033,170 A | 3/2000 | Gold |
| 6,033,406 A | 3/2000 | Mathews |
| 6,033,436 A | 3/2000 | Steinke et al. |
| 6,039,740 A | 3/2000 | Olerud |
| 6,039,761 A | 3/2000 | Li et al. |
| D422,705 S | 4/2000 | Koros et al. |
| 6,045,555 A | 4/2000 | Smith et al. |
| 6,045,579 A | 4/2000 | Hochshuler et al. |
| 6,048,302 A | 4/2000 | Markoll |
| 6,048,342 A | 4/2000 | Zucherman et al. |
| 6,048,343 A | 4/2000 | Mathis et al. |
| 6,050,997 A | 4/2000 | Mullane |
| 6,053,917 A | 4/2000 | Sherman et al. |
| 6,059,785 A | 5/2000 | Schavan et al. |
| 6,059,786 A | 5/2000 | Jackson |
| 6,063,089 A | 5/2000 | Errico et al. |
| 6,063,090 A | 5/2000 | Schlaepfer |
| 6,066,174 A | 5/2000 | Farris |
| 6,066,175 A | 5/2000 | Henderson et al. |
| 6,068,630 A | 5/2000 | Zucherman et al. |
| 6,071,310 A | 6/2000 | Picha et al. |
| 6,074,343 A | 6/2000 | Nathanson et al. |
| 6,074,390 A | 6/2000 | Zucherman et al. |
| 6,074,391 A | 6/2000 | Metz-Stavenhagen et al. |
| 6,077,262 A | 6/2000 | Schlaepfer et al. |
| 6,080,193 A | 6/2000 | Hochshuler et al. |
| 6,083,224 A | 7/2000 | Gertzbein et al. |
| 6,083,225 A | 7/2000 | Winslow et al. |
| 6,083,624 A | 7/2000 | Hiura |
| 6,086,588 A | 7/2000 | Ameil et al. |
| 6,086,589 A | 7/2000 | Kuslich et al. |
| 6,086,613 A | 7/2000 | Camino et al. |
| 6,090,110 A | 7/2000 | Metz-Stavenhagen |
| 6,090,111 A | 7/2000 | Nichols |
| 6,090,113 A | 7/2000 | Le et al. |
| 6,093,205 A | 7/2000 | McLeod et al. |
| 6,096,060 A | 8/2000 | Fitts et al. |
| 6,099,528 A | 8/2000 | Saurat |
| 6,099,531 A | 8/2000 | Bonutti |
| 6,102,912 A | 8/2000 | Cazin et al. |
| 6,102,913 A | 8/2000 | Jackson |
| 6,110,172 A | 8/2000 | Jackson |
| 6,110,173 A | 8/2000 | Thomas, Jr. |
| 6,111,164 A | 8/2000 | Rainey et al. |
| 6,113,599 A | 9/2000 | Landsberger |
| 6,113,601 A | 9/2000 | Tatar |
| 6,113,638 A | 9/2000 | Williams et al. |
| 6,117,135 A | 9/2000 | Schlaepfer |
| 6,117,137 A | 9/2000 | Halm et al. |
| 6,119,631 A | 9/2000 | Markoll |
| 6,120,502 A | 9/2000 | Michelson |
| 6,123,706 A | 9/2000 | Lange |
| 6,123,707 A | 9/2000 | Wagner |
| 6,126,689 A | 10/2000 | Brett |
| 6,132,370 A | 10/2000 | Furnish et al. |
| 6,132,430 A | 10/2000 | Wagner |
| 6,132,431 A | 10/2000 | Nilsson et al. |
| 6,132,432 A | 10/2000 | Richelsoph |
| 6,132,434 A | 10/2000 | Sherman et al. |
| 6,132,464 A | 10/2000 | Martin |
| 6,136,000 A | 10/2000 | Louis et al. |
| 6,136,002 A | 10/2000 | Shih et al. |
| 6,139,316 A | 10/2000 | Sachdeva et al. |
| 6,139,493 A | 10/2000 | Koros et al. |
| 6,139,549 A | 10/2000 | Keller |
| 6,143,032 A | 11/2000 | Schafer et al. |
| 6,146,044 A | 11/2000 | Calvet |
| 6,146,383 A | 11/2000 | Studer et al. |
| 6,146,422 A | 11/2000 | Lawson |
| 6,149,650 A | 11/2000 | Michelson |
| 6,152,927 A | 11/2000 | Farris et al. |
| 6,156,037 A | 12/2000 | Lehuec et al. |
| 6,159,210 A | 12/2000 | Voor |
| 6,159,211 A | 12/2000 | Boriani et al. |

(56) References Cited

U.S. PATENT DOCUMENTS

| | | | |
|---|---|---|---|
| 6,159,215 A | 12/2000 | Urbahns et al. |
| 6,159,244 A | 12/2000 | Suddaby |
| 6,162,252 A | 12/2000 | Kuras et al. |
| 6,174,311 B1 | 1/2001 | Branch et al. |
| 6,176,882 B1 | 1/2001 | Biedermann et al. |
| 6,179,838 B1 | 1/2001 | Fiz |
| 6,179,873 B1 | 1/2001 | Zientek |
| 6,179,874 B1 | 1/2001 | Cauthen |
| 6,183,472 B1 | 2/2001 | Lutz |
| 6,183,473 B1 | 2/2001 | Ashman |
| 6,186,005 B1 | 2/2001 | Leidl |
| 6,186,718 B1 | 2/2001 | Fogard |
| 6,187,005 B1 | 2/2001 | Brace et al. |
| 6,193,720 B1 | 2/2001 | Yuan et al. |
| 6,193,721 B1 | 2/2001 | Michelson |
| 6,193,757 B1 | 2/2001 | Foley et al. |
| 6,197,033 B1 | 3/2001 | Haid, Jr. et al. |
| 6,200,322 B1 | 3/2001 | Branch et al. |
| 6,206,826 B1 | 3/2001 | Mathews et al. |
| 6,206,879 B1 | 3/2001 | Marnay et al. |
| 6,206,922 B1 | 3/2001 | Zdeblick et al. |
| 6,206,923 B1 | 3/2001 | Boyd et al. |
| D440,311 S | 4/2001 | Michelson |
| 6,210,376 B1 | 4/2001 | Grayson |
| 6,210,412 B1 | 4/2001 | Michelson |
| 6,210,413 B1 | 4/2001 | Justis et al. |
| 6,214,005 B1 | 4/2001 | Benzel et al. |
| 6,214,012 B1 | 4/2001 | Karpman et al. |
| 6,221,077 B1 | 4/2001 | Rinner et al. |
| RE37,161 E | 5/2001 | Michelson et al. |
| 6,224,545 B1 | 5/2001 | Cocchia et al. |
| 6,224,595 B1 | 5/2001 | Michelson |
| 6,224,596 B1 | 5/2001 | Jackson |
| 6,224,598 B1 | 5/2001 | Jackson |
| 6,224,602 B1 | 5/2001 | Hayes |
| 6,224,607 B1 | 5/2001 | Michelson |
| 6,226,548 B1 | 5/2001 | Foley et al. |
| 6,228,022 B1 | 5/2001 | Friesem et al. |
| 6,228,085 B1 | 5/2001 | Theken et al. |
| 6,231,575 B1 | 5/2001 | Krag |
| 6,234,705 B1 | 5/2001 | Troxell |
| 6,235,028 B1 | 5/2001 | Brumfield et al. |
| 6,235,034 B1 | 5/2001 | Bray |
| 6,235,726 B1 | 5/2001 | Burns et al. |
| 6,238,396 B1 | 5/2001 | Lombardo |
| 6,241,729 B1 | 6/2001 | Estes et al. |
| 6,241,730 B1 | 6/2001 | Alby |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,248,104 B1 | 6/2001 | Chopin et al. |
| 6,248,105 B1 | 6/2001 | Schlaepfer et al. |
| 6,248,106 B1 | 6/2001 | Ferree |
| 6,248,107 B1 | 6/2001 | Foley et al. |
| 6,248,110 B1 | 6/2001 | Reiley et al. |
| 6,250,984 B1 | 6/2001 | Jin et al. |
| 6,251,112 B1 | 6/2001 | Jackson |
| 6,251,140 B1 | 6/2001 | Marino et al. |
| 6,254,146 B1 | 7/2001 | Church |
| 6,254,602 B1 | 7/2001 | Justis |
| 6,254,603 B1 | 7/2001 | Gertzbein et al. |
| 6,258,089 B1 | 7/2001 | Campbell et al. |
| 6,258,125 B1 | 7/2001 | Paul et al. |
| 6,261,287 B1 | 7/2001 | Metz-Stavenhagen |
| 6,261,291 B1 | 7/2001 | Talaber et al. |
| 6,264,656 B1 | 7/2001 | Michelson |
| 6,267,764 B1 | 7/2001 | Elberg |
| 6,267,765 B1 | 7/2001 | Taylor et al. |
| 6,270,498 B1 | 8/2001 | Michelson |
| 6,273,888 B1 | 8/2001 | Justis |
| 6,273,889 B1 | 8/2001 | Richelsoph |
| 6,277,122 B1 | 8/2001 | McGahan et al. |
| 6,277,149 B1 | 8/2001 | Boyle et al. |
| 6,280,442 B1 | 8/2001 | Barker et al. |
| 6,280,445 B1 | 8/2001 | Morrison et al. |
| D448,081 S | 9/2001 | Koros et al. |
| 6,283,967 B1 | 9/2001 | Troxell et al. |
| 6,287,308 B1 | 9/2001 | Betz et al. |
| 6,287,309 B1 | 9/2001 | Baccelli et al. |
| 6,287,311 B1 | 9/2001 | Sherman et al. |
| 6,290,703 B1 | 9/2001 | Ganem |
| 6,293,949 B1 | 9/2001 | Justis et al. |
| 6,294,202 B1 | 9/2001 | Burns et al. |
| D449,692 S | 10/2001 | Michelson |
| 6,296,642 B1 | 10/2001 | Morrison et al. |
| 6,296,643 B1 | 10/2001 | Hopf et al. |
| 6,296,664 B1 | 10/2001 | Middleton |
| 6,299,613 B1 | 10/2001 | Ogilvie et al. |
| 6,302,843 B1 | 10/2001 | Lees et al. |
| 6,302,888 B1 | 10/2001 | Mellinger et al. |
| 6,302,914 B1 | 10/2001 | Michelson |
| 6,304,178 B1 | 10/2001 | Hayashida |
| 6,306,136 B1 | 10/2001 | Baccelli |
| 6,306,137 B2 | 10/2001 | Troxell |
| 6,306,170 B2 | 10/2001 | Ray |
| 6,309,391 B1 | 10/2001 | Crandall et al. |
| 6,312,431 B1 | 11/2001 | Asfora |
| 6,315,564 B1 | 11/2001 | Levisman |
| 6,315,779 B1 | 11/2001 | Morrison et al. |
| 6,317,957 B1 | 11/2001 | Gregor et al. |
| 6,319,002 B1 | 11/2001 | Pond |
| 6,319,257 B1 | 11/2001 | Carignan et al. |
| 6,322,500 B1 | 11/2001 | Sikora et al. |
| RE37,479 E | 12/2001 | Kuslich |
| 6,331,179 B1 | 12/2001 | Freid et al. |
| 6,332,882 B1 | 12/2001 | Zucherman et al. |
| 6,340,345 B1 | 1/2002 | Lees et al. |
| 6,342,074 B1 | 1/2002 | Simpson |
| 6,344,057 B1 | 2/2002 | Rabbe et al. |
| 6,348,058 B1 | 2/2002 | Melkent et al. |
| 6,348,071 B1 | 2/2002 | Steffee et al. |
| 6,350,283 B1 | 2/2002 | Michelson |
| 6,355,038 B1 | 3/2002 | Pisharodi |
| 6,355,039 B1 | 3/2002 | Troussel et al. |
| 6,355,040 B1 | 3/2002 | Richelsoph et al. |
| 6,360,750 B1 | 3/2002 | Gerber et al. |
| 6,361,258 B1 | 3/2002 | Heesch |
| RE37,665 E | 4/2002 | Ralph |
| 6,364,880 B1 | 4/2002 | Michelson |
| 6,364,881 B1 | 4/2002 | Apgar et al. |
| 6,364,883 B1 | 4/2002 | Santilli |
| 6,368,320 B1 | 4/2002 | Le et al. |
| 6,368,321 B1 | 4/2002 | Jackson |
| 6,368,350 B1 | 4/2002 | Erickson et al. |
| 6,371,957 B1 | 4/2002 | Amrein et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,375,681 B1 | 4/2002 | Truscott |
| 6,379,355 B1 | 4/2002 | Zucherman et al. |
| 6,379,357 B1 | 4/2002 | Bernstein et al. |
| 6,387,130 B1 | 5/2002 | Stone et al. |
| 6,389,391 B1 | 5/2002 | Terauchi |
| 6,395,031 B1 | 5/2002 | Foley et al. |
| 6,395,035 B2 | 5/2002 | Bresina et al. |
| 6,398,783 B1 | 6/2002 | Michelson |
| 6,402,749 B1 | 6/2002 | Ashman |
| 6,402,750 B1 | 6/2002 | Atkinson et al. |
| 6,402,751 B1 | 6/2002 | Hoeck et al. |
| 6,402,752 B2 | 6/2002 | Schaffler-Wachter et al. |
| 6,402,756 B1 | 6/2002 | Ralph et al. |
| 6,402,757 B1 | 6/2002 | Moore, III et al. |
| 6,402,785 B1 | 6/2002 | Zdeblick et al. |
| 6,406,478 B1 | 6/2002 | Kuo |
| 6,409,765 B1 | 6/2002 | Bianchi et al. |
| 6,412,999 B1 | 7/2002 | Pierpont |
| 6,413,258 B1 | 7/2002 | Bernhardt, Jr. |
| 6,413,259 B1 | 7/2002 | Lyons et al. |
| 6,413,278 B1 | 7/2002 | Marchosky |
| 6,416,465 B2 | 7/2002 | Brau |
| 6,416,515 B1 | 7/2002 | Wagner |
| 6,419,676 B1 | 7/2002 | Zucherman et al. |
| 6,419,677 B2 | 7/2002 | Zucherman et al. |

(56) References Cited

U.S. PATENT DOCUMENTS

| | | |
|---|---|---|
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Hoeck et al. |
| 6,428,542 B1 | 8/2002 | Michelson |
| 6,428,576 B1 | 8/2002 | Haldimann |
| 6,432,108 B1 | 8/2002 | Burgess et al. |
| 6,432,140 B1 | 8/2002 | Lin |
| 6,440,133 B1 | 8/2002 | Beale et al. |
| 6,440,137 B1 | 8/2002 | Horvath et al. |
| 6,440,139 B2 | 8/2002 | Michelson |
| 6,440,168 B1 | 8/2002 | Cauthen |
| 6,440,169 B1 | 8/2002 | Elberg et al. |
| 6,440,170 B1 | 8/2002 | Jackson |
| 6,443,956 B1 | 9/2002 | Ray |
| 6,443,989 B1 | 9/2002 | Jackson |
| 6,447,440 B1 | 9/2002 | Markoll |
| 6,447,443 B1 | 9/2002 | Keogh et al. |
| 6,447,547 B1 | 9/2002 | Michelson |
| 6,447,548 B1 | 9/2002 | Ralph et al. |
| 6,451,019 B1 | 9/2002 | Zucherman et al. |
| 6,451,020 B1 | 9/2002 | Zucherman et al. |
| 6,451,021 B1 | 9/2002 | Ralph et al. |
| 6,454,769 B2 | 9/2002 | Wagner et al. |
| 6,454,771 B1 | 9/2002 | Michelson |
| 6,454,773 B1 | 9/2002 | Sherman et al. |
| 6,458,159 B1 | 10/2002 | Thalgott |
| 6,461,358 B1 | 10/2002 | Faccioli et al. |
| 6,461,359 B1 | 10/2002 | Tribus et al. |
| 6,468,310 B1 | 10/2002 | Ralph et al. |
| 6,471,703 B1 | 10/2002 | Ashman |
| 6,471,704 B2 | 10/2002 | Gertzbein et al. |
| 6,471,705 B1 | 10/2002 | Biedermann et al. |
| 6,471,724 B2 | 10/2002 | Zdeblick et al. |
| 6,475,218 B2 | 11/2002 | Gournay et al. |
| 6,478,796 B2 | 11/2002 | Zucherman et al. |
| 6,478,798 B1 | 11/2002 | Howland |
| 6,478,800 B1 | 11/2002 | Fraser et al. |
| 6,478,801 B1 | 11/2002 | Ralph et al. |
| 6,482,234 B1 | 11/2002 | Weber et al. |
| 6,485,491 B1 | 11/2002 | Farris et al. |
| 6,485,492 B1 | 11/2002 | Halm et al. |
| 6,485,494 B1 | 11/2002 | Haider |
| 6,485,517 B1 | 11/2002 | Michelson |
| 6,485,518 B1 | 11/2002 | Cornwall et al. |
| 6,488,681 B2 | 12/2002 | Martin et al. |
| 6,497,726 B1 | 12/2002 | Carter et al. |
| 6,500,205 B1 | 12/2002 | Michelson |
| 6,503,250 B2 | 1/2003 | Paul |
| 6,508,818 B2 | 1/2003 | Steiner et al. |
| 6,508,839 B1 | 1/2003 | Lambrecht et al. |
| 6,511,484 B2 | 1/2003 | Torode et al. |
| 6,514,256 B2 | 2/2003 | Zucherman et al. |
| 6,514,260 B1 | 2/2003 | Zdeblick et al. |
| 6,517,580 B1 | 2/2003 | Ramadan et al. |
| 6,520,962 B1 | 2/2003 | Taylor et al. |
| 6,520,967 B1 | 2/2003 | Cauthen |
| 6,520,996 B1 | 2/2003 | Manasas et al. |
| 6,521,223 B1 | 2/2003 | Calias et al. |
| 6,524,233 B2 | 2/2003 | Markoll |
| 6,524,238 B2 | 2/2003 | Velikaris et al. |
| 6,524,312 B2 | 2/2003 | Landry et al. |
| 6,524,315 B1 | 2/2003 | Selvitelli et al. |
| 6,527,773 B1 | 3/2003 | Lin et al. |
| 6,527,803 B1 | 3/2003 | Crozet et al. |
| 6,527,804 B1 | 3/2003 | Gauchet et al. |
| 6,527,806 B2 | 3/2003 | Ralph et al. |
| 6,530,929 B1 | 3/2003 | Justis et al. |
| 6,531,146 B2 | 3/2003 | Calhoun et al. |
| 6,533,786 B1 | 3/2003 | Needham et al. |
| 6,537,276 B2 | 3/2003 | Metz-Stavenhagen |
| 6,537,279 B1 | 3/2003 | Michelson |
| 6,538,262 B1 | 3/2003 | Crespi et al. |
| 6,539,826 B2 | 4/2003 | Oesterle et al. |
| 6,540,749 B2 | 4/2003 | Schaefer et al. |
| 6,540,785 B1 | 4/2003 | Gill et al. |
| 6,547,790 B2 | 4/2003 | Harkey, III et al. |
| 6,547,795 B2 | 4/2003 | Schneiderman |
| 6,551,242 B1 | 4/2003 | Furnish et al. |
| 6,551,320 B2 | 4/2003 | Lieberman |
| 6,551,322 B1 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,038 B1 | 5/2003 | Morrison |
| 6,562,040 B1 | 5/2003 | Wagner |
| 6,562,046 B2 | 5/2003 | Sasso |
| 6,562,074 B2 | 5/2003 | Gerbec et al. |
| 6,565,565 B1 | 5/2003 | Yuan et al. |
| 6,565,567 B1 | 5/2003 | Haider |
| 6,565,571 B1 | 5/2003 | Jackowski et al. |
| 6,565,605 B2 | 5/2003 | Goble et al. |
| 6,569,168 B2 | 5/2003 | Lin |
| 6,572,618 B1 | 6/2003 | Morrison |
| 6,575,899 B1 | 6/2003 | Foley et al. |
| 6,575,981 B1 | 6/2003 | Boyd et al. |
| 6,576,016 B1 | 6/2003 | Hochshuler et al. |
| 6,579,291 B1 | 6/2003 | Keith et al. |
| 6,579,319 B2 | 6/2003 | Goble et al. |
| 6,582,431 B1 | 6/2003 | Ray |
| 6,582,433 B2 | 6/2003 | Yun |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,589,243 B1 | 7/2003 | Viart et al. |
| 6,592,585 B2 | 7/2003 | Lee et al. |
| 6,592,624 B1 | 7/2003 | Fraser et al. |
| 6,595,992 B1 | 7/2003 | Wagner et al. |
| 6,595,993 B2 | 7/2003 | Donno et al. |
| 6,595,995 B2 | 7/2003 | Zdeblick et al. |
| 6,599,240 B2 | 7/2003 | Puchovsky et al. |
| 6,599,290 B2 | 7/2003 | Bailey et al. |
| 6,599,292 B1 | 7/2003 | Ray |
| 6,599,294 B2 | 7/2003 | Fuss et al. |
| 6,599,295 B1 | 7/2003 | Tornier et al. |
| 6,599,320 B1 | 7/2003 | Kuslich et al. |
| 6,599,321 B2 | 7/2003 | Hyde, Jr. |
| 6,602,254 B2 | 8/2003 | Gertzbein et al. |
| 6,602,255 B1 | 8/2003 | Campbell et al. |
| 6,602,256 B1 | 8/2003 | Hayes |
| 6,602,257 B1 | 8/2003 | Thramann |
| 6,605,089 B1 | 8/2003 | Michelson |
| 6,607,530 B1 | 8/2003 | Carl et al. |
| 6,607,558 B2 | 8/2003 | Kuras |
| 6,610,063 B2 | 8/2003 | Kumar et al. |
| 6,610,089 B1 | 8/2003 | Liu et al. |
| 6,610,093 B1 | 8/2003 | Pisharodi |
| 6,613,050 B1 | 9/2003 | Wagner et al. |
| 6,613,089 B1 | 9/2003 | Estes et al. |
| 6,613,091 B1 | 9/2003 | Zdeblick et al. |
| 6,613,278 B1 | 9/2003 | Mills et al. |
| 6,616,664 B2 | 9/2003 | Walulik et al. |
| 6,616,665 B2 | 9/2003 | Grafton et al. |
| 6,616,667 B1 | 9/2003 | Steiger et al. |
| 6,616,669 B2 | 9/2003 | Ogilvie et al. |
| 6,616,695 B1 | 9/2003 | Crozet et al. |
| 6,620,163 B1 | 9/2003 | Michelson |
| 6,622,344 B1 | 9/2003 | Lu |
| 6,623,485 B2 | 9/2003 | Doubler et al. |
| 6,626,347 B2 | 9/2003 | Ng |
| 6,626,904 B1 | 9/2003 | Jammet et al. |
| 6,626,906 B1 | 9/2003 | Young |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |

(56) References Cited

U.S. PATENT DOCUMENTS

| | | |
|---|---|---|
| 6,635,086 B2 | 10/2003 | Lin |
| 6,635,087 B2 | 10/2003 | Angelucci et al. |
| 6,638,276 B2 | 10/2003 | Sharkey et al. |
| 6,638,310 B2 | 10/2003 | Lin et al. |
| 6,641,583 B2 | 11/2003 | Shluzas et al. |
| 6,641,585 B2 | 11/2003 | Sato et al. |
| 6,641,586 B2 | 11/2003 | Varieur |
| 6,641,614 B1 | 11/2003 | Wagner et al. |
| 6,645,206 B1 | 11/2003 | Zdeblick et al. |
| 6,645,207 B2 | 11/2003 | Dixon et al. |
| 6,645,208 B2 | 11/2003 | Apfelbaum et al. |
| 6,645,249 B2 | 11/2003 | Ralph et al. |
| 6,648,885 B1 | 11/2003 | Friesem |
| 6,648,887 B2 | 11/2003 | Ashman |
| 6,648,888 B1 | 11/2003 | Shluzas |
| 6,648,891 B2 | 11/2003 | Kim |
| 6,648,894 B2 | 11/2003 | Abdelgany et al. |
| 6,648,895 B2 | 11/2003 | Burkus et al. |
| 6,648,917 B2 | 11/2003 | Gerbec et al. |
| 6,652,525 B1 | 11/2003 | Assaker et al. |
| 6,652,526 B1 | 11/2003 | Arafiles |
| 6,652,533 B2 | 11/2003 | O'Neil |
| 6,652,584 B2 | 11/2003 | Michelson |
| 6,652,586 B2 | 11/2003 | Hunter et al. |
| 6,652,765 B1 | 11/2003 | Beaty |
| 6,652,818 B1 | 11/2003 | Mills et al. |
| 6,656,179 B1 | 12/2003 | Schaefer et al. |
| 6,656,181 B2 | 12/2003 | Dixon et al. |
| 6,656,224 B2 | 12/2003 | Middleton |
| 6,660,004 B2 | 12/2003 | Barker et al. |
| 6,660,006 B2 | 12/2003 | Markworth et al. |
| 6,663,631 B2 | 12/2003 | Kuntz |
| 6,663,632 B1 | 12/2003 | Frigg |
| 6,663,635 B2 | 12/2003 | Frigg et al. |
| 6,663,642 B2 | 12/2003 | Beyar et al. |
| 6,665,555 B2 | 12/2003 | Henderson et al. |
| 6,666,612 B2 | 12/2003 | Lorigny et al. |
| 6,666,866 B2 | 12/2003 | Martz et al. |
| 6,666,867 B2 | 12/2003 | Ralph et al. |
| 6,666,890 B2 | 12/2003 | Michelson |
| 6,666,891 B2 | 12/2003 | Boehm et al. |
| 6,668,688 B2 | 12/2003 | Zhao et al. |
| 6,669,700 B1 | 12/2003 | Farris et al. |
| 6,669,730 B2 | 12/2003 | Ralph et al. |
| 6,673,073 B1 | 1/2004 | Schaefer |
| 6,673,113 B2 | 1/2004 | Ralph et al. |
| 6,673,362 B2 | 1/2004 | Calhoun et al. |
| 6,675,805 B1 | 1/2004 | Graether |
| 6,676,661 B1 | 1/2004 | Martin et al. |
| 6,676,703 B2 | 1/2004 | Biscup |
| 6,679,833 B2 | 1/2004 | Smith et al. |
| 6,679,883 B2 | 1/2004 | Hawkes et al. |
| 6,679,887 B2 | 1/2004 | Nicholson et al. |
| 6,679,915 B1 | 1/2004 | Cauthen |
| 6,682,529 B2 | 1/2004 | Stahurski |
| 6,682,530 B2 | 1/2004 | Dixon et al. |
| 6,682,533 B1 | 1/2004 | Dinsdale et al. |
| 6,682,562 B2 | 1/2004 | Viart et al. |
| 6,683,690 B1 | 1/2004 | Tobias |
| 6,685,705 B1 | 2/2004 | Taylor |
| 6,689,133 B2 | 2/2004 | Morrison et al. |
| 6,689,134 B2 | 2/2004 | Ralph et al. |
| 6,692,495 B1 | 2/2004 | Zacouto |
| 6,695,842 B2 | 2/2004 | Zucherman et al. |
| 6,695,843 B2 | 2/2004 | Biedermann et al. |
| 6,695,846 B2 | 2/2004 | Richelsoph et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,699,249 B2 | 3/2004 | Schlaepfer et al. |
| 6,702,814 B2 | 3/2004 | Walulik et al. |
| 6,706,045 B2 | 3/2004 | Lin et al. |
| 6,706,067 B2 | 3/2004 | Shimp et al. |
| 6,706,068 B2 | 3/2004 | Ferree |
| 6,706,070 B1 | 3/2004 | Wagner et al. |
| 6,706,922 B2 | 3/2004 | Wolff et al. |
| 6,709,389 B2 | 3/2004 | Farascioni |
| 6,709,458 B2 | 3/2004 | Michelson |
| 6,709,461 B2 | 3/2004 | O'Neil et al. |
| 6,712,795 B1 | 3/2004 | Cohen |
| 6,712,818 B1 | 3/2004 | Michelson |
| 6,712,819 B2 | 3/2004 | Zucherman et al. |
| 6,712,852 B1 | 3/2004 | Chung et al. |
| 6,716,212 B1 | 4/2004 | Pickens |
| 6,716,213 B2 | 4/2004 | Shitoto |
| 6,716,214 B1 | 4/2004 | Jackson |
| 6,716,247 B2 | 4/2004 | Michelson |
| 6,719,794 B2 | 4/2004 | Gerber et al. |
| 6,719,795 B1 | 4/2004 | Cornwall et al. |
| 6,723,043 B2 | 4/2004 | Kleeman et al. |
| 6,723,096 B1 | 4/2004 | Dorchak et al. |
| 6,723,100 B2 | 4/2004 | Biedermann et al. |
| 6,723,126 B1 | 4/2004 | Berry |
| 6,723,127 B2 | 4/2004 | Ralph et al. |
| 6,723,128 B2 | 4/2004 | Uk |
| 6,726,685 B2 | 4/2004 | To et al. |
| 6,726,687 B2 | 4/2004 | Jackson |
| 6,726,720 B2 | 4/2004 | Ross et al. |
| 6,730,093 B2 | 5/2004 | Saint |
| 6,730,126 B2 | 5/2004 | Boehm, Jr. et al. |
| 6,730,127 B2 | 5/2004 | Michelson |
| 6,733,444 B2 | 5/2004 | Phillips |
| 6,733,496 B2 | 5/2004 | Sharkey et al. |
| 6,733,502 B2 | 5/2004 | Altarac et al. |
| 6,733,531 B1 | 5/2004 | Trieu |
| 6,733,534 B2 | 5/2004 | Sherman |
| 6,733,535 B2 | 5/2004 | Michelson |
| 6,736,816 B2 | 5/2004 | Ritland |
| 6,736,817 B2 | 5/2004 | Troxell et al. |
| 6,736,820 B2 | 5/2004 | Biedermann et al. |
| 6,739,068 B1 | 5/2004 | Rinner |
| 6,740,086 B2 | 5/2004 | Richelsoph |
| 6,740,087 B2 | 5/2004 | Knox |
| 6,740,090 B1 | 5/2004 | Cragg et al. |
| 6,740,118 B2 | 5/2004 | Eisermann et al. |
| 6,743,231 B1 | 6/2004 | Gray et al. |
| 6,743,255 B2 | 6/2004 | Ferree |
| 6,743,256 B2 | 6/2004 | Mason |
| 6,743,257 B2 | 6/2004 | Castro |
| 6,746,449 B2 | 6/2004 | Jones et al. |
| 6,746,454 B2 | 6/2004 | Winterbottom et al. |
| 6,749,613 B1 | 6/2004 | Conchy et al. |
| 6,749,614 B2 | 6/2004 | Teitelbaum et al. |
| 6,749,635 B1 | 6/2004 | Bryan |
| 6,749,636 B2 | 6/2004 | Michelson |
| 6,752,832 B2 | 6/2004 | Neumann |
| 6,755,829 B1 | 6/2004 | Bono et al. |
| 6,755,830 B2 | 6/2004 | Minfelde et al. |
| 6,755,833 B1 | 6/2004 | Paul et al. |
| 6,755,835 B2 | 6/2004 | Schultheiss et al. |
| 6,755,836 B1 | 6/2004 | Lewis |
| 6,755,841 B2 | 6/2004 | Fraser et al. |
| 6,758,861 B2 | 7/2004 | Ralph et al. |
| 6,761,719 B2 | 7/2004 | Justis et al. |
| 6,761,720 B1 | 7/2004 | Senegas |
| 6,761,721 B2 | 7/2004 | Burgess et al. |
| 6,761,723 B2 | 7/2004 | Buttermann et al. |
| 6,761,738 B1 | 7/2004 | Boyd |
| 6,764,515 B2 | 7/2004 | Ralph et al. |
| 6,767,351 B2 | 7/2004 | Orbay et al. |
| 6,767,367 B1 | 7/2004 | Michelson |
| 6,770,074 B2 | 8/2004 | Michelson |
| 6,770,075 B2 | 8/2004 | Howland |
| 6,770,096 B2 | 8/2004 | Bolger et al. |
| 6,778,861 B1 | 8/2004 | Liebrecht et al. |
| 6,780,186 B2 | 8/2004 | Errico et al. |
| 6,780,192 B2 | 8/2004 | McKay et al. |
| 6,783,527 B2 | 8/2004 | Drewry et al. |
| 6,783,547 B2 | 8/2004 | Castro |
| 6,790,209 B2 | 9/2004 | Beale et al. |
| 6,790,210 B1 | 9/2004 | Cragg et al. |
| 6,793,658 B2 | 9/2004 | Lehuec et al. |
| 6,802,844 B2 | 10/2004 | Ferree |
| 6,805,697 B1 | 10/2004 | Helm et al. |

(56) References Cited

U.S. PATENT DOCUMENTS

| | | |
|---|---|---|
| 6,805,713 B1 | 10/2004 | Carter et al. |
| 6,805,714 B2 | 10/2004 | Sutcliffe |
| 6,808,493 B1 | 10/2004 | Bookwalter et al. |
| 6,808,537 B2 | 10/2004 | Michelson |
| 6,811,567 B2 | 11/2004 | Reiley |
| 6,814,737 B2 | 11/2004 | Cauthen |
| 6,821,277 B2 | 11/2004 | Teitelbaum |
| 6,824,565 B2 | 11/2004 | Muhanna et al. |
| 6,827,719 B2 | 12/2004 | Ralph et al. |
| 6,827,722 B1 | 12/2004 | Schoenefeld |
| 6,830,570 B1 | 12/2004 | Frey et al. |
| 6,830,571 B2 | 12/2004 | Lenke et al. |
| 6,830,589 B2 | 12/2004 | Erickson |
| 6,832,997 B2 | 12/2004 | Uchida et al. |
| 6,832,999 B2 | 12/2004 | Ueyama et al. |
| 6,835,196 B2 | 12/2004 | Biedermann et al. |
| 6,835,206 B2 | 12/2004 | Jackson |
| 6,837,884 B2 | 1/2005 | Woloszko |
| 6,837,889 B2 | 1/2005 | Shluzas |
| 6,840,940 B2 | 1/2005 | Ralph et al. |
| 6,843,791 B2 | 1/2005 | Serhan |
| 6,849,076 B2 | 2/2005 | Blunn et al. |
| 6,849,093 B2 | 2/2005 | Michelson |
| 6,852,127 B2 | 2/2005 | Varga et al. |
| 6,852,128 B2 | 2/2005 | Lange |
| 6,852,129 B2 | 2/2005 | Gerbec et al. |
| 6,855,147 B2 | 2/2005 | Harrington et al. |
| 6,857,343 B1 | 2/2005 | Easterbrooks et al. |
| 6,858,030 B2 | 2/2005 | Martin et al. |
| 6,858,031 B2 | 2/2005 | Morrison et al. |
| 6,860,850 B2 | 3/2005 | Phillips et al. |
| 6,863,673 B2 | 3/2005 | Gerbec et al. |
| 6,869,398 B2 | 3/2005 | Obenchain et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,875,211 B2 | 4/2005 | Nichols et al. |
| 6,881,228 B2 | 4/2005 | Zdeblick et al. |
| 6,884,241 B2 | 4/2005 | Bertranou et al. |
| 6,884,242 B2 | 4/2005 | Lehuec et al. |
| 6,884,243 B2 | 4/2005 | Sellers |
| 6,885,243 B2 | 4/2005 | Burstein et al. |
| D505,205 S | 5/2005 | Freid |
| 6,887,242 B2 | 5/2005 | Doubler et al. |
| 6,890,355 B2 | 5/2005 | Michelson |
| 6,893,444 B2 | 5/2005 | Orbay |
| 6,896,675 B2 | 5/2005 | Leung et al. |
| 6,896,676 B2 | 5/2005 | Zubok et al. |
| 6,896,677 B1 | 5/2005 | Lin |
| 6,896,680 B2 | 5/2005 | Michelson |
| 6,899,714 B2 | 5/2005 | Vaughan |
| 6,899,716 B2 | 5/2005 | Cragg |
| 6,902,566 B2 | 6/2005 | Zucherman et al. |
| 6,902,580 B2 | 6/2005 | Fallin et al. |
| 6,911,045 B2 | 6/2005 | Shimp |
| 6,916,320 B2 | 7/2005 | Michelson |
| 6,916,340 B2 | 7/2005 | Metzger et al. |
| 6,918,910 B2 | 7/2005 | Smith et al. |
| 6,918,911 B2 | 7/2005 | Biedermann et al. |
| 6,921,403 B2 | 7/2005 | Cragg et al. |
| 6,923,811 B1 | 8/2005 | Carl et al. |
| 6,923,830 B2 | 8/2005 | Michelson |
| 6,926,658 B2 | 8/2005 | Farnan |
| 6,926,737 B2 | 8/2005 | Jackson |
| 6,929,606 B2 | 8/2005 | Ritland |
| 6,929,640 B1 | 8/2005 | Underwood et al. |
| 6,932,817 B2 | 8/2005 | Baynham et al. |
| 6,932,820 B2 | 8/2005 | Osman |
| 6,936,071 B1 | 8/2005 | Marnay et al. |
| 6,945,933 B2 | 9/2005 | Branch et al. |
| 6,945,972 B2 | 9/2005 | Frigg et al. |
| 6,945,973 B2 | 9/2005 | Bray |
| 6,945,975 B2 | 9/2005 | Dalton |
| 6,947,967 B2 | 9/2005 | Ferris et al. |
| 6,949,100 B1 | 9/2005 | Venturini |
| 6,949,105 B2 | 9/2005 | Bryan et al. |
| 6,951,538 B2 | 10/2005 | Ritland |
| 6,951,561 B2 | 10/2005 | Warren et al. |
| 6,953,462 B2 | 10/2005 | Lieberman |
| 6,953,477 B2 | 10/2005 | Berry |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,666 B2 | 11/2005 | Jackson |
| 6,964,667 B2 | 11/2005 | Shaolian et al. |
| 6,964,687 B1 | 11/2005 | Bernard et al. |
| 6,966,910 B2 | 11/2005 | Ritland |
| 6,966,929 B2 | 11/2005 | Mitchell |
| 6,972,019 B2 | 12/2005 | Michelson |
| 6,972,035 B2 | 12/2005 | Michelson |
| 6,974,460 B2 | 12/2005 | Carbone et al. |
| 6,979,334 B2 | 12/2005 | Dalton |
| 6,980,862 B2 | 12/2005 | Fredricks et al. |
| 6,981,973 B2 | 1/2006 | McKinley |
| 6,981,975 B2 | 1/2006 | Michelson |
| 6,984,234 B2 | 1/2006 | Bray |
| 6,984,245 B2 | 1/2006 | McGahan et al. |
| 6,986,771 B2 | 1/2006 | Paul et al. |
| 6,986,772 B2 | 1/2006 | Michelson |
| 6,989,011 B2 | 1/2006 | Paul et al. |
| 6,989,044 B2 | 1/2006 | Zhang et al. |
| 6,991,632 B2 | 1/2006 | Ritland |
| 6,991,654 B2 | 1/2006 | Foley |
| 6,994,688 B2 | 2/2006 | Brauckman et al. |
| 6,997,941 B2 | 2/2006 | Sharkey et al. |
| 7,001,385 B2 | 2/2006 | Bonutti |
| 7,001,432 B2 | 2/2006 | Keller et al. |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,008,426 B2 | 3/2006 | Paul |
| 7,008,453 B1 | 3/2006 | Michelson |
| 7,011,619 B1 | 3/2006 | Lewis et al. |
| 7,011,658 B2 | 3/2006 | Young |
| 7,011,660 B2 | 3/2006 | Sherman et al. |
| 7,014,608 B2 | 3/2006 | Larson et al. |
| 7,014,633 B2 | 3/2006 | Cragg |
| 7,018,378 B2 | 3/2006 | Biedermann et al. |
| 7,018,379 B2 | 3/2006 | Drewry et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,022,122 B2 | 4/2006 | Amrein et al. |
| 7,025,716 B1 | 4/2006 | Meloul et al. |
| 7,025,787 B2 | 4/2006 | Bryan et al. |
| 7,029,472 B1 | 4/2006 | Fortin |
| 7,029,475 B2 | 4/2006 | Panjabi |
| 7,033,362 B2 | 4/2006 | McGahan et al. |
| RE39,089 E | 5/2006 | Ralph et al. |
| 7,037,339 B2 | 5/2006 | Houfburg |
| 7,041,135 B2 | 5/2006 | Michelson |
| 7,041,136 B2 | 5/2006 | Goble et al. |
| 7,044,971 B2 | 5/2006 | Suddaby |
| 7,048,736 B2 | 5/2006 | Robinson et al. |
| 7,052,497 B2 | 5/2006 | Sherman et al. |
| 7,056,321 B2 | 6/2006 | Pagliuca et al. |
| 7,056,344 B2 | 6/2006 | Huppert et al. |
| 7,060,066 B2 | 6/2006 | Zhao et al. |
| 7,060,097 B2 | 6/2006 | Fraser et al. |
| 7,063,702 B2 | 6/2006 | Michelson |
| 7,066,062 B2 | 6/2006 | Flesher |
| 7,066,937 B2 | 6/2006 | Shluzas |
| 7,066,961 B2 | 6/2006 | Michelson |
| 7,070,598 B2 | 7/2006 | Lim et al. |
| 7,074,237 B2 | 7/2006 | Goble et al. |
| 7,081,116 B1 | 7/2006 | Carly |
| 7,083,621 B2 | 8/2006 | Shaolian et al. |
| 7,083,622 B2 | 8/2006 | Simonson |
| 7,083,625 B2 | 8/2006 | Berry |
| 7,083,649 B2 | 8/2006 | Zucherman et al. |
| 7,087,057 B2 | 8/2006 | Konieczynski et al. |
| 7,087,058 B2 | 8/2006 | Cragg |

(56) References Cited

U.S. PATENT DOCUMENTS

| | | |
|---|---|---|
| 7,087,083 B2 | 8/2006 | Pasquet et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,094,258 B2 | 8/2006 | Lambrecht et al. |
| 7,097,648 B1 | 8/2006 | Globerman et al. |
| 7,101,375 B2 | 9/2006 | Zucherman et al. |
| 7,101,399 B2 | 9/2006 | Errico et al. |
| 7,105,024 B2 | 9/2006 | Richelsoph |
| 7,108,698 B2 | 9/2006 | Robbins et al. |
| 7,112,206 B2 | 9/2006 | Michelson |
| 7,118,576 B2 | 10/2006 | Gitis et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,121,755 B2 | 10/2006 | Schlapfer et al. |
| 7,122,629 B2 | 10/2006 | Bejanin et al. |
| 7,125,410 B2 | 10/2006 | Freudiger |
| 7,125,425 B2 | 10/2006 | Simonton et al. |
| 7,125,426 B2 | 10/2006 | Moumene et al. |
| 7,128,743 B2 | 10/2006 | Metz-Stavenhagen |
| 7,128,760 B2 | 10/2006 | Michelson |
| 7,128,761 B2 | 10/2006 | Kuras et al. |
| 7,137,985 B2 | 11/2006 | Jahng |
| 7,137,986 B2 | 11/2006 | Troxell et al. |
| 7,141,051 B2 | 11/2006 | Janowski et al. |
| 7,144,396 B2 | 12/2006 | Shluzas |
| 7,144,397 B2 | 12/2006 | Lambrecht et al. |
| 7,147,599 B2 | 12/2006 | Phillips et al. |
| 7,150,714 B2 | 12/2006 | Myles |
| 7,153,281 B2 | 12/2006 | Holmes |
| 7,153,325 B2 | 12/2006 | Kim et al. |
| 7,156,806 B2 | 1/2007 | Dobrovolny |
| 7,160,300 B2 | 1/2007 | Jackson |
| 7,163,538 B2 | 1/2007 | Altarac et al. |
| 7,163,539 B2 | 1/2007 | Abdelgany et al. |
| 7,163,558 B2 | 1/2007 | Senegas et al. |
| 7,163,561 B2 | 1/2007 | Michelson |
| 7,166,073 B2 | 1/2007 | Ritland |
| 7,166,107 B2 | 1/2007 | Anderson |
| 7,166,108 B2 | 1/2007 | Mazda et al. |
| 7,166,121 B2 | 1/2007 | Reiley et al. |
| 7,169,183 B2 | 1/2007 | Liu et al. |
| 7,179,261 B2 | 2/2007 | Sicvol et al. |
| 7,182,729 B2 | 2/2007 | Abdelgany et al. |
| 7,186,255 B2 | 3/2007 | Baynham et al. |
| 7,188,626 B2 | 3/2007 | Foley et al. |
| 7,198,644 B2 | 4/2007 | Schultz et al. |
| 7,201,751 B2 | 4/2007 | Zucherman et al. |
| 7,204,851 B2 | 4/2007 | Trieu et al. |
| 7,204,852 B2 | 4/2007 | Marnay et al. |
| 7,204,853 B2 | 4/2007 | Gordon et al. |
| 7,207,949 B2 | 4/2007 | Miles et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,211,112 B2 | 5/2007 | Baynham et al. |
| 7,214,186 B2 | 5/2007 | Ritland |
| 7,214,227 B2 | 5/2007 | Colleran et al. |
| 7,217,291 B2 | 5/2007 | Zucherman et al. |
| 7,223,268 B2 | 5/2007 | Biedermann |
| 7,223,289 B2 | 5/2007 | Trieu et al. |
| 7,227,477 B2 | 6/2007 | Ye |
| 7,229,441 B2 | 6/2007 | Trieu et al. |
| 7,232,441 B2 | 6/2007 | Altarac et al. |
| 7,232,463 B2 | 6/2007 | Falahee |
| 7,232,464 B2 | 6/2007 | Mathieu et al. |
| 7,235,048 B2 | 6/2007 | Rein et al. |
| 7,235,105 B2 | 6/2007 | Jackson |
| 7,241,297 B2 | 7/2007 | Shaolian et al. |
| 7,250,052 B2 | 7/2007 | Landry et al. |
| 7,252,673 B2 | 8/2007 | Lim |
| 7,264,621 B2 | 9/2007 | Coates et al. |
| 7,270,665 B2 | 9/2007 | Morrison et al. |
| 7,273,496 B2 | 9/2007 | Mitchell |
| 7,276,081 B1 | 10/2007 | Coates et al. |
| 7,276,082 B2 | 10/2007 | Zdeblick et al. |
| 7,282,063 B2 | 10/2007 | Cohen et al. |
| 7,282,064 B2 | 10/2007 | Chin |
| 7,282,065 B2 | 10/2007 | Kirschman |
| 7,285,121 B2 | 10/2007 | Braun et al. |
| 7,291,149 B1 | 11/2007 | Michelson |
| 7,291,151 B2 | 11/2007 | Alvarez |
| 7,291,152 B2 | 11/2007 | Abdou |
| 7,291,153 B2 | 11/2007 | Glascott |
| 7,294,128 B2 | 11/2007 | Alleyne et al. |
| 7,294,129 B2 | 11/2007 | Hawkins et al. |
| 7,300,441 B2 | 11/2007 | Haid et al. |
| 7,303,563 B2 | 12/2007 | Poyner et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,306,628 B2 | 12/2007 | Zucherman et al. |
| 7,309,338 B2 | 12/2007 | Cragg |
| 7,311,734 B2 | 12/2007 | Hoeck et al. |
| 7,314,467 B2 | 1/2008 | Howland |
| 7,316,684 B1 | 1/2008 | Baccelli et al. |
| 7,316,714 B2 | 1/2008 | Gordon et al. |
| 7,318,817 B2 | 1/2008 | Hamada |
| 7,318,840 B2 | 1/2008 | McKay |
| 7,322,979 B2 | 1/2008 | Crandall et al. |
| 7,326,216 B2 | 2/2008 | Bertagnoli et al. |
| 7,329,258 B2 | 2/2008 | Studer |
| 7,331,961 B2 | 2/2008 | Abdou |
| 7,331,995 B2 | 2/2008 | Eisermann et al. |
| 7,335,201 B2 | 2/2008 | Doubler et al. |
| 7,335,202 B2 | 2/2008 | Matthis et al. |
| 7,335,203 B2 | 2/2008 | Winslow et al. |
| 7,338,490 B2 | 3/2008 | Ogilvie et al. |
| 7,338,491 B2 | 3/2008 | Baker et al. |
| 7,338,527 B2 | 3/2008 | Blatt et al. |
| 7,341,587 B2 | 3/2008 | Molz et al. |
| 7,347,874 B2 | 3/2008 | Disilvestro |
| 7,361,179 B2 | 4/2008 | Rousseau et al. |
| 7,361,196 B2 | 4/2008 | Fallin et al. |
| 7,374,534 B2 | 5/2008 | Dalton |
| 7,377,921 B2 | 5/2008 | Studer et al. |
| 7,377,942 B2 | 5/2008 | Berry |
| 7,396,328 B2 | 7/2008 | Penenberg |
| 7,396,360 B2 | 7/2008 | Lieberman |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,637 B2 | 11/2008 | Taylor |
| 7,455,639 B2 | 11/2008 | Ritland |
| 7,455,685 B2 | 11/2008 | Justis |
| 7,465,306 B2 | 12/2008 | Pond, Jr. et al. |
| 7,473,223 B2 | 1/2009 | Fetzer |
| 7,473,276 B2 | 1/2009 | Aebi et al. |
| 7,476,228 B2 | 1/2009 | Abdou |
| 7,476,238 B2 | 1/2009 | Panjabi |
| 7,479,160 B2 | 1/2009 | Branch et al. |
| 7,485,132 B1 | 2/2009 | McBride et al. |
| 7,491,205 B1 | 2/2009 | Michelson |
| 7,491,208 B2 | 2/2009 | Pond, Jr. et al. |
| 7,494,508 B2 | 2/2009 | Zeegers |
| 7,497,859 B2 | 3/2009 | Zucherman et al. |
| 7,503,918 B2 | 3/2009 | Baccelli et al. |
| 7,503,933 B2 | 3/2009 | Michelson |
| 7,520,888 B2 | 4/2009 | Trieu |
| 7,527,640 B2 | 5/2009 | Ziolo et al. |
| 7,534,265 B1 | 5/2009 | Boyd et al. |
| 7,537,565 B2 | 5/2009 | Bass |
| 7,537,616 B1 | 5/2009 | Branch et al. |
| 7,540,882 B2 | 6/2009 | Michelson |
| 7,547,308 B2 | 6/2009 | Bertagnoli et al. |
| 7,547,325 B2 | 6/2009 | Biedermann et al. |
| 7,556,639 B2 | 7/2009 | Rothman et al. |

(56) References Cited

U.S. PATENT DOCUMENTS

| | | |
|---|---|---|
| 7,559,930 B2 | 7/2009 | Allard et al. |
| 7,559,942 B2 | 7/2009 | Paul et al. |
| 7,563,274 B2 | 7/2009 | Justis et al. |
| 7,563,283 B2 | 7/2009 | Kwak |
| 7,566,345 B1 | 7/2009 | Fallin et al. |
| 7,569,014 B2 | 8/2009 | Bass et al. |
| 7,572,276 B2 | 8/2009 | Lim et al. |
| 7,575,580 B2 | 8/2009 | Lim et al. |
| 7,575,587 B2 | 8/2009 | Rezach et al. |
| 7,578,820 B2 | 8/2009 | Moore et al. |
| 7,578,849 B2 | 8/2009 | Trieu |
| 7,582,058 B1 | 9/2009 | Miles et al. |
| 7,582,107 B2 | 9/2009 | Trail et al. |
| 7,585,316 B2 | 9/2009 | Trieu |
| 7,588,537 B2 | 9/2009 | Bass |
| 7,588,579 B2 | 9/2009 | Mommaerts |
| 7,588,589 B2 | 9/2009 | Falahee |
| 7,588,593 B2 | 9/2009 | Aferzon |
| 7,591,839 B2 | 9/2009 | Biedermann et al. |
| 7,591,851 B2 | 9/2009 | Winslow et al. |
| 7,594,919 B2 | 9/2009 | Peterman |
| 7,594,931 B2 | 9/2009 | Louis et al. |
| 7,594,932 B2 | 9/2009 | Aferzon et al. |
| 7,597,694 B2 | 10/2009 | Lim et al. |
| 7,601,166 B2 | 10/2009 | Biedermann et al. |
| 7,601,170 B2 | 10/2009 | Winslow et al. |
| 7,604,643 B2 | 10/2009 | Ciccone et al. |
| 7,604,654 B2 | 10/2009 | Fallin et al. |
| 7,611,518 B2 | 11/2009 | Walder et al. |
| 7,618,423 B1 | 11/2009 | Valentine et al. |
| 7,618,443 B2 | 11/2009 | Abdou |
| 7,618,455 B2 | 11/2009 | Goble et al. |
| 7,618,456 B2 | 11/2009 | Mathieu et al. |
| 7,621,912 B2 | 11/2009 | Harms et al. |
| 7,621,939 B2 | 11/2009 | Zucherman et al. |
| 7,621,940 B2 | 11/2009 | Harms et al. |
| 7,621,942 B2 | 11/2009 | Piehl |
| 7,621,953 B2 | 11/2009 | Braddock et al. |
| 7,621,955 B2 | 11/2009 | Goble et al. |
| 7,621,957 B2 | 11/2009 | Errico et al. |
| 7,625,379 B2 | 12/2009 | Puno et al. |
| 7,625,380 B2 | 12/2009 | Drewry et al. |
| 7,625,393 B2 | 12/2009 | Fallin et al. |
| 7,625,396 B2 | 12/2009 | Jackson |
| 7,628,799 B2 | 12/2009 | Richelsoph et al. |
| 7,632,292 B2 | 12/2009 | Sengupta et al. |
| 7,635,366 B2 | 12/2009 | Abdou |
| 7,635,371 B2 | 12/2009 | McGahan et al. |
| 7,641,673 B2 | 1/2010 | Le et al. |
| 7,641,690 B2 | 1/2010 | Abdou |
| 7,641,693 B2 | 1/2010 | Gutlin et al. |
| 7,645,281 B2 | 1/2010 | Marik |
| 7,651,515 B2 | 1/2010 | Mack et al. |
| 7,654,954 B1 | 2/2010 | Phillips et al. |
| 7,655,026 B2 | 2/2010 | Justis et al. |
| 7,655,027 B2 | 2/2010 | Michelson |
| 7,655,028 B2 | 2/2010 | Kirschman |
| 7,655,042 B2 | 2/2010 | Foley et al. |
| 7,658,739 B2 | 2/2010 | Shluzas |
| 7,658,752 B2 | 2/2010 | Labrom et al. |
| 7,658,766 B2 | 2/2010 | Melkent et al. |
| 7,682,375 B2 | 3/2010 | Ritland |
| 7,682,396 B2 | 3/2010 | Beaurain et al. |
| 7,686,809 B2 | 3/2010 | Triplett et al. |
| 7,691,057 B2 | 4/2010 | Miles et al. |
| 7,691,129 B2 | 4/2010 | Felix |
| 7,695,496 B2 | 4/2010 | Labrom et al. |
| 7,695,498 B2 | 4/2010 | Ritland |
| 7,695,514 B2 | 4/2010 | Kwak |
| 7,695,516 B2 | 4/2010 | Zeegers |
| 7,695,517 B2 | 4/2010 | Benzel et al. |
| 7,704,271 B2 | 4/2010 | Abdou |
| 7,708,743 B2 | 5/2010 | Anderson et al. |
| 7,708,765 B2 | 5/2010 | Carl et al. |
| 7,722,618 B2 | 5/2010 | Estes et al. |
| 7,727,233 B2 | 6/2010 | Blackwell et al. |
| 7,727,280 B2 | 6/2010 | McLuen |
| 7,738,968 B2 | 6/2010 | Bleich |
| 7,744,635 B2 | 6/2010 | Sweeney et al. |
| 7,749,231 B2 | 7/2010 | Bonvallet et al. |
| 7,749,251 B2 | 7/2010 | Obenchain et al. |
| 7,749,252 B2 | 7/2010 | Zucherman et al. |
| 7,749,269 B2 | 7/2010 | Peterman et al. |
| 7,749,270 B2 | 7/2010 | Peterman |
| 7,749,274 B2 | 7/2010 | Razian |
| 7,753,844 B2 | 7/2010 | Sharratt et al. |
| 7,753,937 B2 | 7/2010 | Chervitz et al. |
| 7,753,938 B2 | 7/2010 | Aschmann et al. |
| 7,753,958 B2 | 7/2010 | Gordon et al. |
| 7,758,274 B2 | 7/2010 | Paul |
| 7,758,501 B2 | 7/2010 | Frasier et al. |
| 7,758,644 B2 | 7/2010 | Trieu et al. |
| 7,758,645 B2 | 7/2010 | Studer et al. |
| 7,758,648 B2 | 7/2010 | Castleman et al. |
| 7,763,074 B2 | 7/2010 | Altarac et al. |
| 7,763,078 B2 | 7/2010 | Peterman et al. |
| 7,766,918 B2 | 8/2010 | Allard et al. |
| 7,771,432 B2 | 8/2010 | Schwab et al. |
| 7,771,473 B2 | 8/2010 | Thramann |
| 7,771,475 B2 | 8/2010 | Michelson |
| 7,776,049 B1 | 8/2010 | Curran et al. |
| 7,776,067 B2 | 8/2010 | Jackson |
| 7,776,090 B2 | 8/2010 | Winslow et al. |
| 7,780,670 B2 | 8/2010 | Bonutti |
| 7,780,732 B2 | 8/2010 | Abernathie et al. |
| 7,789,914 B2 | 9/2010 | Michelson |
| 7,794,501 B2 | 9/2010 | Edie et al. |
| 7,799,053 B2 | 9/2010 | Haid, Jr. et al. |
| 7,799,081 B2 | 9/2010 | McKinley |
| 7,806,911 B2 | 10/2010 | Peckham |
| 7,806,913 B2 | 10/2010 | Fanger et al. |
| 7,811,326 B2 | 10/2010 | Braddock, Jr. et al. |
| 7,815,683 B2 | 10/2010 | Melkent et al. |
| 7,819,801 B2 | 10/2010 | Miles et al. |
| 7,819,903 B2 | 10/2010 | Fraser et al. |
| 7,824,445 B2 | 11/2010 | Biro et al. |
| 7,828,807 B2 | 11/2010 | Lehuec et al. |
| 7,828,847 B2 | 11/2010 | Abdou |
| 7,837,688 B2 | 11/2010 | Boyer, II et al. |
| 7,837,714 B2 | 11/2010 | Drewry et al. |
| 7,837,732 B2 | 11/2010 | Zucherman et al. |
| 7,837,734 B2 | 11/2010 | Zucherman et al. |
| 7,842,074 B2 | 11/2010 | Abdou |
| 7,846,186 B2 | 12/2010 | Taylor |
| 7,846,207 B2 | 12/2010 | Lechmann et al. |
| 7,850,608 B2 | 12/2010 | Hamada |
| 7,850,731 B2 | 12/2010 | Brittan et al. |
| 7,850,732 B2 | 12/2010 | Heinz |
| 7,850,733 B2 | 12/2010 | Baynham et al. |
| 7,854,752 B2 | 12/2010 | Colleran et al. |
| 7,857,818 B2 | 12/2010 | Trieu et al. |
| 7,857,833 B2 | 12/2010 | Abdou |
| 7,871,426 B2 | 1/2011 | Chin et al. |
| 7,875,034 B2 | 1/2011 | Josse et al. |
| 7,875,076 B2 | 1/2011 | Mathieu et al. |
| 7,875,078 B2 | 1/2011 | Wysocki et al. |
| 7,879,074 B2 | 2/2011 | Kwak et al. |
| 7,883,532 B2 | 2/2011 | Biscup et al. |
| 7,883,542 B2 | 2/2011 | Zipnick et al. |
| 7,887,591 B2 | 2/2011 | Aebi et al. |
| 7,892,173 B2 | 2/2011 | Miles et al. |
| 7,892,261 B2 | 2/2011 | Bonutti |
| 7,892,286 B2 | 2/2011 | Michelson |
| 7,901,409 B2 | 3/2011 | Canaveral et al. |
| 7,901,458 B2 | 3/2011 | Deridder et al. |
| 7,905,840 B2 | 3/2011 | Pimenta et al. |
| 7,905,886 B1 | 3/2011 | Curran et al. |
| 7,909,829 B2 | 3/2011 | Patel et al. |
| 7,909,848 B2 | 3/2011 | Patel et al. |
| 7,909,870 B2 | 3/2011 | Kraus |
| 7,909,871 B2 | 3/2011 | Abdou |
| 7,914,558 B2 | 3/2011 | Landry et al. |
| 7,918,792 B2 | 4/2011 | Drzyzga et al. |
| 7,922,658 B2 | 4/2011 | Cohen et al. |

(56) References Cited

U.S. PATENT DOCUMENTS

| | | |
|---|---|---|
| 7,922,745 B2 | 4/2011 | Hestad et al. |
| 7,922,750 B2 | 4/2011 | Trautwein et al. |
| 7,927,337 B2 | 4/2011 | Keller |
| 7,931,589 B2 | 4/2011 | Cohen et al. |
| 7,931,674 B2 | 4/2011 | Zucherman et al. |
| 7,935,134 B2 | 5/2011 | Reglos et al. |
| 7,935,147 B2 | 5/2011 | Wales |
| 7,935,149 B2 | 5/2011 | Michelson |
| 7,938,848 B2 | 5/2011 | Sweeney |
| 7,946,982 B2 | 5/2011 | Hamada |
| 7,951,198 B2 | 5/2011 | Sucec et al. |
| 7,955,390 B2 | 6/2011 | Fallin et al. |
| 7,955,392 B2 | 6/2011 | Dewey et al. |
| 7,959,564 B2 | 6/2011 | Ritland |
| 7,959,677 B2 | 6/2011 | Landry et al. |
| 7,972,363 B2 | 7/2011 | Moskowitz et al. |
| 7,976,566 B2 | 7/2011 | Michelson |
| 7,981,031 B2 | 7/2011 | Frasier et al. |
| 7,985,258 B2 | 7/2011 | Zdeblick et al. |
| 7,988,699 B2 | 8/2011 | Martz et al. |
| 8,002,802 B2 | 8/2011 | Abdou |
| 8,002,833 B2 | 8/2011 | Fabris et al. |
| 8,002,842 B2 | 8/2011 | Ronk |
| 8,012,207 B2 | 9/2011 | Kim |
| 8,021,393 B2 | 9/2011 | Seifert et al. |
| 8,021,401 B2 | 9/2011 | Carl et al. |
| 8,021,429 B2 | 9/2011 | Viker |
| 8,025,680 B2 | 9/2011 | Hayes et al. |
| 8,025,697 B2 | 9/2011 | McClellan, III et al. |
| 8,034,109 B2 | 10/2011 | Zwirkoski |
| 8,034,110 B2 | 10/2011 | Garner et al. |
| 8,038,716 B2 | 10/2011 | Duggal et al. |
| 8,043,334 B2 | 10/2011 | Fisher et al. |
| 8,043,343 B2 | 10/2011 | Miller et al. |
| 8,043,376 B2 | 10/2011 | Falahee |
| 8,043,380 B1 | 10/2011 | Park et al. |
| 8,048,120 B1 | 11/2011 | Fallin et al. |
| 8,062,299 B2 | 11/2011 | McGahan et al. |
| 8,062,336 B2 | 11/2011 | Triplett et al. |
| 8,062,337 B2 | 11/2011 | Bruneau et al. |
| 8,066,710 B2 | 11/2011 | Estes et al. |
| 8,066,714 B2 | 11/2011 | Shipp et al. |
| 8,066,741 B2 | 11/2011 | Fallin et al. |
| 8,066,742 B2 | 11/2011 | Anderson et al. |
| 8,066,749 B2 | 11/2011 | Winslow et al. |
| 8,070,749 B2 | 12/2011 | Stern |
| 8,070,816 B2 | 12/2011 | Taylor |
| 8,075,593 B2 | 12/2011 | Hess |
| 8,075,618 B2 | 12/2011 | Trieu et al. |
| 8,075,621 B2 | 12/2011 | Michelson |
| 8,080,046 B2 | 12/2011 | Suddaby |
| 8,083,798 B2 | 12/2011 | Allard et al. |
| 8,097,018 B2 | 1/2012 | Malandain et al. |
| 8,100,828 B2 | 1/2012 | Frey et al. |
| 8,105,358 B2 | 1/2012 | Phan |
| 8,114,131 B2 | 2/2012 | Kohm et al. |
| 8,123,807 B2 | 2/2012 | Kim |
| 8,128,659 B2 | 3/2012 | Ginsberg et al. |
| 8,128,664 B2 | 3/2012 | Pasquet |
| 8,137,284 B2 | 3/2012 | Miles et al. |
| 8,142,479 B2 | 3/2012 | Hess |
| 8,157,840 B2 | 4/2012 | Zucherman et al. |
| 8,163,026 B2 | 4/2012 | Gray |
| 8,167,887 B2 | 5/2012 | McLean |
| 8,167,908 B2 | 5/2012 | Ely et al. |
| 8,167,915 B2 | 5/2012 | Ferree et al. |
| 8,167,946 B2 | 5/2012 | Michelson |
| 8,167,949 B2 | 5/2012 | Tyber et al. |
| 8,172,855 B2 | 5/2012 | Abdou |
| 8,182,423 B2 | 5/2012 | Miles et al. |
| 8,192,358 B2 | 6/2012 | Leahy |
| 8,197,514 B2 | 6/2012 | Maas et al. |
| 8,197,522 B2 | 6/2012 | Park et al. |
| 8,206,420 B2 | 6/2012 | Patel et al. |
| 8,216,312 B2 | 7/2012 | Gray |
| 8,226,690 B2 | 7/2012 | Altarac et al. |
| 8,231,623 B1 | 7/2012 | Jordan |
| 8,241,330 B2 | 8/2012 | Lamborne et al. |
| 8,241,359 B2 | 8/2012 | Davis et al. |
| 8,241,362 B2 | 8/2012 | Voorhies |
| 8,251,997 B2 | 8/2012 | Michelson |
| 8,268,004 B2 | 9/2012 | Castleman et al. |
| 8,277,489 B2 | 10/2012 | Saidha et al. |
| 8,287,569 B1 | 10/2012 | Powell |
| 8,303,629 B1 | 11/2012 | Abdou |
| 8,303,660 B1 | 11/2012 | Abdou |
| 8,308,804 B2 | 11/2012 | Krueger |
| 8,343,046 B2 | 1/2013 | Miles et al. |
| 8,343,190 B1 | 1/2013 | Mueller et al. |
| 8,349,012 B2 | 1/2013 | McKay |
| 8,353,826 B2 | 1/2013 | Weiman et al. |
| 8,361,108 B2 | 1/2013 | Gold et al. |
| 8,382,801 B2 | 2/2013 | Lamborne et al. |
| 8,388,660 B1 | 3/2013 | Abdou |
| 8,388,687 B2 | 3/2013 | Gimbel et al. |
| 8,397,522 B2 | 3/2013 | Springer et al. |
| 8,403,959 B2 | 3/2013 | Doellinger |
| 8,419,738 B2 | 4/2013 | Smisson, III et al. |
| 8,419,772 B2 | 4/2013 | Thompson et al. |
| 8,425,602 B2 | 4/2013 | Guyer et al. |
| 8,435,268 B2 | 5/2013 | Thompson et al. |
| 8,435,269 B2 | 5/2013 | Woolley et al. |
| 8,439,953 B2 | 5/2013 | Mitchell et al. |
| 8,454,621 B2 | 6/2013 | Deridder et al. |
| 8,454,661 B2 | 6/2013 | Rathbun et al. |
| 8,454,694 B2 | 6/2013 | Armstrong et al. |
| 8,465,547 B2 | 6/2013 | Melkent et al. |
| RE44,380 E | 7/2013 | De et al. |
| 8,475,497 B2 | 7/2013 | Grizzard |
| 8,480,712 B1 | 7/2013 | Samuel et al. |
| 8,480,747 B2 | 7/2013 | Melkent et al. |
| 8,486,147 B2 | 7/2013 | De et al. |
| 8,491,471 B2 | 7/2013 | Deshmukh et al. |
| 8,506,629 B2 | 8/2013 | Weiland |
| 8,512,343 B2 | 8/2013 | Dziedzic et al. |
| 8,529,611 B2 | 9/2013 | Champagne et al. |
| 8,562,650 B2 | 10/2013 | Dace |
| 8,574,267 B2 | 11/2013 | Linares |
| 8,603,143 B2 | 12/2013 | Robinson |
| 8,623,088 B1 | 1/2014 | Tohmeh et al. |
| 8,636,655 B1 | 1/2014 | Childs |
| 8,636,772 B2 | 1/2014 | Schmierer et al. |
| 8,657,855 B2 | 2/2014 | Zhang |
| 8,663,331 B2 | 3/2014 | McClellan, III et al. |
| 8,685,065 B1 | 4/2014 | Taber et al. |
| 8,685,093 B2 | 4/2014 | Anderson et al. |
| 8,690,917 B2 | 4/2014 | Suh et al. |
| 8,690,950 B2 | 4/2014 | Refai et al. |
| 8,696,709 B2 | 4/2014 | Dinville et al. |
| 8,702,756 B2 | 4/2014 | Reimels |
| 8,721,686 B2 | 5/2014 | Gordon et al. |
| 8,721,689 B2 | 5/2014 | Butler et al. |
| 8,771,318 B2 | 7/2014 | Triplett et al. |
| 8,771,360 B2 * | 7/2014 | Jimenez ............... A61F 2/4465 623/17.16 |
| 8,795,335 B1 | 8/2014 | Abdou et al. |
| 8,795,375 B2 | 8/2014 | Malberg |
| 8,827,900 B1 | 9/2014 | Pimenta |
| 8,828,055 B2 | 9/2014 | Blain et al. |
| 8,828,056 B2 | 9/2014 | Buss et al. |
| 8,828,061 B2 | 9/2014 | Scrantz et al. |
| 8,845,728 B1 | 9/2014 | Abdou |
| 8,876,904 B2 | 11/2014 | Pimenta et al. |
| 8,900,137 B1 | 12/2014 | Lovell et al. |
| 8,906,092 B2 | 12/2014 | Abdou |
| 8,911,441 B2 | 12/2014 | Dace et al. |
| 8,940,019 B2 | 1/2015 | Gordon et al. |
| 8,940,051 B2 | 1/2015 | Gimbel et al. |
| 8,940,052 B2 | 1/2015 | Lechmann et al. |
| 8,956,415 B2 | 2/2015 | Cowan |
| 8,974,381 B1 | 3/2015 | Lovell et al. |
| 8,998,905 B2 | 4/2015 | Marik et al. |
| 9,005,248 B2 | 4/2015 | Taber et al. |
| 9,011,538 B2 | 4/2015 | Allard et al. |

(56) References Cited

U.S. PATENT DOCUMENTS

| | | |
|---|---|---|
| 9,044,280 B1 | 6/2015 | Arambula et al. |
| 9,113,853 B1 | 8/2015 | Casey et al. |
| 9,135,059 B2 | 9/2015 | Ballard et al. |
| 9,179,903 B2 | 11/2015 | Cianfrani et al. |
| 9,198,767 B2 | 12/2015 | Abdou |
| 9,211,147 B2 | 12/2015 | Gordon et al. |
| 9,247,968 B2 | 2/2016 | Taber et al. |
| 9,265,526 B1 | 2/2016 | Abdou |
| 9,308,099 B2 | 4/2016 | Triplett et al. |
| 9,320,506 B2 | 4/2016 | Bertagnoli et al. |
| 9,345,464 B2 | 5/2016 | Abdou et al. |
| 9,364,338 B2 | 6/2016 | Malberg |
| 9,408,596 B2 | 8/2016 | Blain |
| 9,408,717 B2 | 8/2016 | Perrow et al. |
| 9,445,918 B1 | 9/2016 | Lin et al. |
| 9,451,940 B2 | 9/2016 | Spann |
| 9,486,328 B2 * | 11/2016 | Jimenez ............... A61F 2/447 |
| 9,622,795 B2 | 4/2017 | Reitblat et al. |
| 9,655,505 B1 | 5/2017 | Gharib et al. |
| 9,687,356 B1 | 6/2017 | Spangler et al. |
| 9,687,357 B2 | 6/2017 | Bannigan et al. |
| 9,730,737 B2 | 8/2017 | Baynham et al. |
| 9,730,802 B1 | 8/2017 | Harvey |
| 9,795,367 B1 | 10/2017 | Lee et al. |
| 9,795,370 B2 | 10/2017 | O'Connell et al. |
| RE46,647 E | 12/2017 | Messerli et al. |
| 9,867,714 B1 | 1/2018 | Abdou |
| 9,901,458 B1 | 2/2018 | Abdou |
| 10,166,018 B2 | 1/2019 | Hunt et al. |
| 10,426,450 B2 | 10/2019 | Vogel et al. |
| 10,548,740 B1 * | 2/2020 | Abdou ................ A61F 2/447 |
| 2001/0001129 A1 | 5/2001 | McKay et al. |
| 2001/0012938 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2001/0047172 A1 | 11/2001 | Foley et al. |
| 2001/0053914 A1 | 12/2001 | Landry et al. |
| 2001/0056219 A1 | 12/2001 | Brauckman et al. |
| 2002/0016595 A1 | 2/2002 | Michelson |
| 2002/0019626 A1 | 2/2002 | Sharkey et al. |
| 2002/0019637 A1 | 2/2002 | Frey et al. |
| 2002/0026101 A1 | 2/2002 | Bookwalter et al. |
| 2002/0032484 A1 | 3/2002 | Hyde |
| 2002/0045899 A1 | 4/2002 | Errico et al. |
| 2002/0045904 A1 | 4/2002 | Fuss et al. |
| 2002/0045945 A1 | 4/2002 | Liu et al. |
| 2002/0049394 A1 | 4/2002 | Roy et al. |
| 2002/0049444 A1 | 4/2002 | Knox |
| 2002/0049446 A1 | 4/2002 | Harkey et al. |
| 2002/0055738 A1 | 5/2002 | Lieberman |
| 2002/0055741 A1 | 5/2002 | Schlapfer et al. |
| 2002/0058944 A1 | 5/2002 | Michelson |
| 2002/0065558 A1 | 5/2002 | Varga et al. |
| 2002/0077530 A1 | 6/2002 | Velikaris et al. |
| 2002/0082602 A1 | 6/2002 | Biedermann et al. |
| 2002/0082700 A1 | 6/2002 | Bianchi et al. |
| 2002/0099386 A1 | 7/2002 | Beger et al. |
| 2002/0111628 A1 | 8/2002 | Ralph et al. |
| 2002/0120268 A1 | 8/2002 | Berger |
| 2002/0128713 A1 | 9/2002 | Ferree |
| 2002/0138146 A1 | 9/2002 | Jackson |
| 2002/0143328 A1 | 10/2002 | Shluzas et al. |
| 2002/0143332 A1 | 10/2002 | Lin et al. |
| 2002/0143341 A1 | 10/2002 | Biedermann et al. |
| 2002/0147449 A1 | 10/2002 | Yun |
| 2002/0161368 A1 | 10/2002 | Foley et al. |
| 2002/0165550 A1 | 11/2002 | Frey et al. |
| 2002/0165612 A1 | 11/2002 | Gerber et al. |
| 2002/0169450 A1 | 11/2002 | Lange |
| 2002/0169453 A1 | 11/2002 | Berger |
| 2002/0183748 A1 | 12/2002 | Martin et al. |
| 2002/0183755 A1 | 12/2002 | Michelson |
| 2002/0183761 A1 | 12/2002 | Johnson et al. |
| 2002/0183848 A1 | 12/2002 | Ray et al. |
| 2002/0188296 A1 | 12/2002 | Michelson |
| 2003/0000350 A1 | 1/2003 | Zhao et al. |
| 2003/0004572 A1 | 1/2003 | Goble et al. |
| 2003/0014068 A1 | 1/2003 | Bonutti et al. |
| 2003/0014123 A1 | 1/2003 | Copf et al. |
| 2003/0018389 A1 | 1/2003 | Castro et al. |
| 2003/0023240 A1 | 1/2003 | Amrein et al. |
| 2003/0023243 A1 | 1/2003 | Biedermann et al. |
| 2003/0023305 A1 | 1/2003 | McKay |
| 2003/0023306 A1 | 1/2003 | Liu et al. |
| 2003/0023308 A1 | 1/2003 | Leroux et al. |
| 2003/0028251 A1 | 2/2003 | Mathews |
| 2003/0040746 A1 | 2/2003 | Mitchell et al. |
| 2003/0040798 A1 | 2/2003 | Michelson |
| 2003/0045878 A1 | 3/2003 | Petit et al. |
| 2003/0045935 A1 | 3/2003 | Angelucci et al. |
| 2003/0055430 A1 | 3/2003 | Kim |
| 2003/0060826 A1 | 3/2003 | Foley et al. |
| 2003/0065330 A1 | 4/2003 | Zucherman et al. |
| 2003/0065395 A1 | 4/2003 | Ralph et al. |
| 2003/0065396 A1 | 4/2003 | Michelson |
| 2003/0073997 A1 | 4/2003 | Doubler et al. |
| 2003/0074001 A1 | 4/2003 | Apfelbaum et al. |
| 2003/0074005 A1 | 4/2003 | Roth et al. |
| 2003/0078583 A1 | 4/2003 | Biedermann et al. |
| 2003/0078662 A1 | 4/2003 | Ralph et al. |
| 2003/0078664 A1 | 4/2003 | Ralph et al. |
| 2003/0083747 A1 | 5/2003 | Winterbottom et al. |
| 2003/0088251 A1 | 5/2003 | Braun et al. |
| 2003/0093153 A1 | 5/2003 | Banick et al. |
| 2003/0094812 A1 | 5/2003 | Balsells |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0125742 A1 | 7/2003 | Yuan et al. |
| 2003/0139813 A1 | 7/2003 | Messerli et al. |
| 2003/0149341 A1 | 8/2003 | Clifton |
| 2003/0149431 A1 | 8/2003 | Varieur |
| 2003/0149432 A1 | 8/2003 | Frigg et al. |
| 2003/0149484 A1 | 8/2003 | Michelson |
| 2003/0153911 A1 | 8/2003 | Shluzas |
| 2003/0153913 A1 | 8/2003 | Altarac et al. |
| 2003/0163133 A1 | 8/2003 | Altarac et al. |
| 2003/0163199 A1 | 8/2003 | Boehm et al. |
| 2003/0167058 A1 | 9/2003 | Shluzas |
| 2003/0171749 A1 | 9/2003 | Le et al. |
| 2003/0171751 A1 | 9/2003 | Ritland |
| 2003/0176862 A1 | 9/2003 | Taylor et al. |
| 2003/0176864 A1 | 9/2003 | Ueyama et al. |
| 2003/0176923 A1 | 9/2003 | Keller et al. |
| 2003/0181975 A1 | 9/2003 | Ishii et al. |
| 2003/0187436 A1 | 10/2003 | Bolger et al. |
| 2003/0187510 A1 | 10/2003 | Hyde |
| 2003/0191470 A1 | 10/2003 | Ritland |
| 2003/0195518 A1 | 10/2003 | Cragg |
| 2003/0195633 A1 | 10/2003 | Hyde |
| 2003/0199873 A1 | 10/2003 | Richelsoph |
| 2003/0199981 A1 | 10/2003 | Ferree |
| 2003/0208202 A1 | 11/2003 | Falahee |
| 2003/0208203 A1 | 11/2003 | Lim et al. |
| 2003/0208204 A1 | 11/2003 | Bailey et al. |
| 2003/0208273 A1 | 11/2003 | Eisermann et al. |
| 2003/0212398 A1 | 11/2003 | Jackson |
| 2003/0216735 A1 | 11/2003 | Altarac et al. |
| 2003/0216736 A1 | 11/2003 | Robinson et al. |
| 2003/0216737 A1 | 11/2003 | Biscup |
| 2003/0217809 A1 | 11/2003 | Morishige |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229347 A1 | 12/2003 | Sherman et al. |
| 2003/0233136 A1 | 12/2003 | Williams et al. |
| 2003/0236472 A1 | 12/2003 | Van et al. |
| 2003/0236572 A1 | 12/2003 | Bertram |
| 2004/0002708 A1 | 1/2004 | Ritland |
| 2004/0006342 A1 | 1/2004 | Altarac et al. |
| 2004/0006391 A1 | 1/2004 | Reiley |

(56) References Cited

U.S. PATENT DOCUMENTS

| | | |
|---|---|---|
| 2004/0010253 A1 | 1/2004 | Morrison |
| 2004/0012938 A1 | 1/2004 | Sylvester et al. |
| 2004/0018228 A1 | 1/2004 | Fischell et al. |
| 2004/0019263 A1 | 1/2004 | Jutras et al. |
| 2004/0030338 A1 | 2/2004 | Paul |
| 2004/0030346 A1 | 2/2004 | Frey et al. |
| 2004/0039387 A1 | 2/2004 | Gause et al. |
| 2004/0044412 A1 | 3/2004 | Lambrecht et al. |
| 2004/0049189 A1 | 3/2004 | Le et al. |
| 2004/0049190 A1 | 3/2004 | Biedermann et al. |
| 2004/0049271 A1 | 3/2004 | Biedermann et al. |
| 2004/0049280 A1 | 3/2004 | Cauthen |
| 2004/0054412 A1 | 3/2004 | Gerbec et al. |
| 2004/0059318 A1 | 3/2004 | Zhang et al. |
| 2004/0068261 A1 | 4/2004 | Fourcault et al. |
| 2004/0068318 A1 | 4/2004 | Coates et al. |
| 2004/0073215 A1 | 4/2004 | Carli |
| 2004/0073216 A1 | 4/2004 | Lieberman |
| 2004/0078079 A1 | 4/2004 | Foley |
| 2004/0078082 A1 | 4/2004 | Lange |
| 2004/0087947 A1 | 5/2004 | Lim et al. |
| 2004/0087948 A1 | 5/2004 | Suddaby |
| 2004/0087949 A1 | 5/2004 | Bono et al. |
| 2004/0087952 A1 | 5/2004 | Borgstrom et al. |
| 2004/0092930 A1 | 5/2004 | Petit et al. |
| 2004/0092933 A1 | 5/2004 | Shaolian et al. |
| 2004/0092934 A1 | 5/2004 | Howland |
| 2004/0093083 A1 | 5/2004 | Branch et al. |
| 2004/0097933 A1 | 5/2004 | Lourdel et al. |
| 2004/0097935 A1 | 5/2004 | Richelsoph et al. |
| 2004/0097940 A1 | 5/2004 | Paul |
| 2004/0098129 A1 | 5/2004 | Lin |
| 2004/0102780 A1 | 5/2004 | West |
| 2004/0106927 A1 | 6/2004 | Ruffner et al. |
| 2004/0106995 A1 | 6/2004 | Le et al. |
| 2004/0106996 A1 | 6/2004 | Liu et al. |
| 2004/0111136 A1 | 6/2004 | Sharkey et al. |
| 2004/0111141 A1 | 6/2004 | Brabec et al. |
| 2004/0116929 A1 | 6/2004 | Barker et al. |
| 2004/0116965 A1 | 6/2004 | Falkenberg |
| 2004/0122518 A1 | 6/2004 | Rhoda |
| 2004/0127963 A1 | 7/2004 | Uchida et al. |
| 2004/0127990 A1 | 7/2004 | Bartish et al. |
| 2004/0127994 A1 | 7/2004 | Kast et al. |
| 2004/0133207 A1 | 7/2004 | Abdou |
| 2004/0138662 A1 | 7/2004 | Landry et al. |
| 2004/0138671 A1 | 7/2004 | Zander et al. |
| 2004/0143264 A1 | 7/2004 | McAfee |
| 2004/0143265 A1 | 7/2004 | Landry et al. |
| 2004/0143270 A1 | 7/2004 | Zucherman et al. |
| 2004/0143332 A1 | 7/2004 | Krueger et al. |
| 2004/0147928 A1 | 7/2004 | Landry et al. |
| 2004/0147929 A1 | 7/2004 | Biedermann et al. |
| 2004/0153065 A1 | 8/2004 | Lim |
| 2004/0153070 A1 | 8/2004 | Barker et al. |
| 2004/0158247 A1 | 8/2004 | Sitiso et al. |
| 2004/0158254 A1 | 8/2004 | Eisermann |
| 2004/0162558 A1 | 8/2004 | Hegde et al. |
| 2004/0162560 A1 | 8/2004 | Raynor et al. |
| 2004/0167520 A1 | 8/2004 | Zucherman et al. |
| 2004/0167625 A1 | 8/2004 | Beyar et al. |
| 2004/0167626 A1 | 8/2004 | Geremakis et al. |
| 2004/0172022 A1 | 9/2004 | Landry et al. |
| 2004/0172025 A1 | 9/2004 | Drewry et al. |
| 2004/0172134 A1 | 9/2004 | Berry |
| 2004/0176766 A1 | 9/2004 | Shluzas |
| 2004/0181226 A1 | 9/2004 | Michelson |
| 2004/0181285 A1 | 9/2004 | Simonson |
| 2004/0186473 A1 | 9/2004 | Cournoyer et al. |
| 2004/0186572 A1 | 9/2004 | Lange et al. |
| 2004/0193151 A1 | 9/2004 | To et al. |
| 2004/0193159 A1 | 9/2004 | Zucherman et al. |
| 2004/0195089 A1 | 10/2004 | O'Brien |
| 2004/0204712 A1 | 10/2004 | Kolb et al. |
| 2004/0204713 A1 | 10/2004 | Abdou |
| 2004/0210216 A1 | 10/2004 | Farris et al. |
| 2004/0215190 A1 | 10/2004 | Nguyen et al. |
| 2004/0220567 A1 | 11/2004 | Eisermann et al. |
| 2004/0220670 A1 | 11/2004 | Eisermann et al. |
| 2004/0220671 A1 | 11/2004 | Ralph et al. |
| 2004/0225289 A1 | 11/2004 | Biedermann et al. |
| 2004/0225291 A1 | 11/2004 | Schwammberger et al. |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0230309 A1 | 11/2004 | Dimauro et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0236333 A1 | 11/2004 | Lin |
| 2004/0236425 A1 | 11/2004 | Huang |
| 2004/0243240 A1 | 12/2004 | Beaurain et al. |
| 2004/0249377 A1 | 12/2004 | Kaes et al. |
| 2004/0249379 A1 | 12/2004 | Winslow et al. |
| 2004/0249380 A1 | 12/2004 | Glascott |
| 2004/0249461 A1 | 12/2004 | Ferree |
| 2004/0254574 A1 | 12/2004 | Morrison et al. |
| 2004/0254575 A1 | 12/2004 | Obenchain et al. |
| 2004/0260283 A1 | 12/2004 | Wu et al. |
| 2004/0260291 A1 | 12/2004 | Jensen |
| 2004/0267264 A1 | 12/2004 | Konieczynski et al. |
| 2004/0267369 A1 | 12/2004 | Lyons et al. |
| 2005/0004573 A1 | 1/2005 | Abdou |
| 2005/0010227 A1 | 1/2005 | Paul |
| 2005/0010291 A1 | 1/2005 | Stinson et al. |
| 2005/0010301 A1 | 1/2005 | Disilvestro et al. |
| 2005/0012506 A1 | 1/2005 | Yudahira |
| 2005/0015149 A1 | 1/2005 | Michelson |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0021041 A1 | 1/2005 | Michelson |
| 2005/0027296 A1 | 2/2005 | Thramann et al. |
| 2005/0027360 A1 | 2/2005 | Webb et al. |
| 2005/0033296 A1 | 2/2005 | Bono et al. |
| 2005/0033298 A1 | 2/2005 | Hawkes et al. |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0038432 A1 | 2/2005 | Shaolian et al. |
| 2005/0038511 A1 | 2/2005 | Martz et al. |
| 2005/0043800 A1 | 2/2005 | Paul et al. |
| 2005/0043802 A1 | 2/2005 | Eisermann et al. |
| 2005/0049705 A1 | 3/2005 | Hale et al. |
| 2005/0049708 A1 | 3/2005 | Atkinson et al. |
| 2005/0055026 A1 | 3/2005 | Biedermann et al. |
| 2005/0055031 A1 | 3/2005 | Lim |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0069701 A1 | 3/2005 | Watanabe et al. |
| 2005/0070899 A1 | 3/2005 | Doubler et al. |
| 2005/0070901 A1 | 3/2005 | David |
| 2005/0071007 A1 | 3/2005 | Malek |
| 2005/0075636 A1 | 4/2005 | Gotzen |
| 2005/0080320 A1 | 4/2005 | Lee et al. |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0085909 A1 | 4/2005 | Eisermann |
| 2005/0096652 A1 | 5/2005 | Burton |
| 2005/0096653 A1 | 5/2005 | Doubler et al. |
| 2005/0096654 A1 | 5/2005 | Lin |
| 2005/0096745 A1 | 5/2005 | Andre et al. |
| 2005/0107788 A1 | 5/2005 | Beaurain et al. |
| 2005/0113830 A1 | 5/2005 | Rezach et al. |
| 2005/0113833 A1 | 5/2005 | Davison |
| 2005/0113927 A1 | 5/2005 | Malek |
| 2005/0113928 A1 | 5/2005 | Cragg et al. |
| 2005/0119663 A1 | 6/2005 | Keyer et al. |

(56) References Cited

U.S. PATENT DOCUMENTS

| | | |
|---|---|---|
| 2005/0119747 A1 | 6/2005 | Fabris et al. |
| 2005/0119748 A1 | 6/2005 | Reiley et al. |
| 2005/0124991 A1 | 6/2005 | Jahng |
| 2005/0125061 A1 | 6/2005 | Zucherman et al. |
| 2005/0125066 A1 | 6/2005 | McAfee |
| 2005/0126576 A1 | 6/2005 | Ferree |
| 2005/0131404 A1 | 6/2005 | Mazda et al. |
| 2005/0131406 A1 | 6/2005 | Reiley et al. |
| 2005/0131407 A1 | 6/2005 | Sicvol et al. |
| 2005/0131409 A1 | 6/2005 | Chervitz et al. |
| 2005/0131413 A1 | 6/2005 | O'Driscoll et al. |
| 2005/0131420 A1 | 6/2005 | Techiera et al. |
| 2005/0131421 A1 | 6/2005 | Anderson et al. |
| 2005/0137597 A1 | 6/2005 | Butler et al. |
| 2005/0137604 A1 | 6/2005 | Assell et al. |
| 2005/0143737 A1 | 6/2005 | Pafford et al. |
| 2005/0143822 A1 | 6/2005 | Paul |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149035 A1 | 7/2005 | Pimenta et al. |
| 2005/0149188 A1 | 7/2005 | Cook et al. |
| 2005/0149196 A1 | 7/2005 | Zucherman et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0154461 A1 | 7/2005 | Humphreys et al. |
| 2005/0159750 A1 | 7/2005 | Doherty |
| 2005/0159756 A1 | 7/2005 | Ray |
| 2005/0159813 A1 | 7/2005 | Molz, IV |
| 2005/0159815 A1 | 7/2005 | Kamimura et al. |
| 2005/0165396 A1 | 7/2005 | Fortin et al. |
| 2005/0165398 A1 | 7/2005 | Reiley |
| 2005/0165400 A1 | 7/2005 | Fernandez |
| 2005/0165487 A1 | 7/2005 | Muhanna et al. |
| 2005/0171540 A1 | 8/2005 | Lim et al. |
| 2005/0171541 A1 | 8/2005 | Boehm et al. |
| 2005/0171543 A1 | 8/2005 | Timm et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177163 A1 | 8/2005 | Abdou et al. |
| 2005/0177164 A1 | 8/2005 | Walters et al. |
| 2005/0177166 A1 | 8/2005 | Timm et al. |
| 2005/0177167 A1 | 8/2005 | Muckter |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0177240 A1 | 8/2005 | Blain |
| 2005/0182401 A1 | 8/2005 | Timm et al. |
| 2005/0182404 A1 | 8/2005 | Lauryssen et al. |
| 2005/0187548 A1 | 8/2005 | Butler et al. |
| 2005/0187555 A1 | 8/2005 | Biedermann et al. |
| 2005/0187628 A1 | 8/2005 | Michelson |
| 2005/0192571 A1 | 9/2005 | Abdelgany |
| 2005/0192577 A1 | 9/2005 | Mosca et al. |
| 2005/0192580 A1 | 9/2005 | Dalton |
| 2005/0192589 A1 | 9/2005 | Raymond et al. |
| 2005/0192671 A1 | 9/2005 | Bao et al. |
| 2005/0197660 A1 | 9/2005 | Haid, Jr. et al. |
| 2005/0197702 A1 | 9/2005 | Coppes et al. |
| 2005/0203511 A1 | 9/2005 | Wilson-Macdonald et al. |
| 2005/0203512 A1 | 9/2005 | Hawkins et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0203533 A1 | 9/2005 | Ferguson et al. |
| 2005/0203604 A1 | 9/2005 | Brabec et al. |
| 2005/0203624 A1 | 9/2005 | Serhan et al. |
| 2005/0209694 A1 | 9/2005 | Loeb |
| 2005/0215999 A1 | 9/2005 | Birkmeyer et al. |
| 2005/0216001 A1 | 9/2005 | David |
| 2005/0216003 A1 | 9/2005 | Biedermann et al. |
| 2005/0216083 A1 | 9/2005 | Michelson |
| 2005/0222682 A1 | 10/2005 | Link et al. |
| 2005/0222683 A1 | 10/2005 | Berry |
| 2005/0228376 A1 | 10/2005 | Boomer et al. |
| 2005/0228377 A1 | 10/2005 | Chao et al. |
| 2005/0228395 A1 | 10/2005 | Auxepaules et al. |
| 2005/0228400 A1 | 10/2005 | Chao et al. |
| 2005/0228501 A1 | 10/2005 | Miller et al. |
| 2005/0234449 A1 | 10/2005 | Aferzon |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234555 A1 | 10/2005 | Sutton et al. |
| 2005/0240181 A1 | 10/2005 | Boomer et al. |
| 2005/0240183 A1 | 10/2005 | Vaughan |
| 2005/0240265 A1 | 10/2005 | Kuiper et al. |
| 2005/0240273 A1 | 10/2005 | Khandkar et al. |
| 2005/0245928 A1 | 11/2005 | Colleran et al. |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0251258 A1 | 11/2005 | Jackson |
| 2005/0256576 A1 | 11/2005 | Moskowitz et al. |
| 2005/0256578 A1 | 11/2005 | Blatt et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0261768 A1 | 11/2005 | Trieu |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0267579 A1 | 12/2005 | Reiley et al. |
| 2005/0267580 A1 | 12/2005 | Suddaby |
| 2005/0273099 A1 | 12/2005 | Baccelli et al. |
| 2005/0273101 A1 | 12/2005 | Schumacher |
| 2005/0273120 A1 | 12/2005 | Abdou et al. |
| 2005/0273171 A1 | 12/2005 | Gordon et al. |
| 2005/0277919 A1 | 12/2005 | Slivka et al. |
| 2005/0277921 A1 | 12/2005 | Eisermann et al. |
| 2005/0277922 A1 | 12/2005 | Trieu et al. |
| 2005/0277923 A1 | 12/2005 | Sweeney |
| 2005/0277924 A1 | 12/2005 | Roychowdhury |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278026 A1 | 12/2005 | Gordon et al. |
| 2005/0283152 A1 | 12/2005 | Lindemann et al. |
| 2005/0283153 A1 | 12/2005 | Poyner et al. |
| 2005/0283157 A1 | 12/2005 | Coates et al. |
| 2005/0283236 A1 | 12/2005 | Razian |
| 2005/0283238 A1 | 12/2005 | Reiley |
| 2005/0283241 A1 | 12/2005 | Keller et al. |
| 2005/0283244 A1 | 12/2005 | Gordon et al. |
| 2005/0283245 A1 | 12/2005 | Gordon et al. |
| 2005/0288669 A1 | 12/2005 | Abdou et al. |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0004367 A1 | 1/2006 | Alamin et al. |
| 2006/0004453 A1 | 1/2006 | Bartish et al. |
| 2006/0009767 A1 | 1/2006 | Kiester |
| 2006/0009768 A1 | 1/2006 | Ritland |
| 2006/0009769 A1 | 1/2006 | Lieberman |

(56) References Cited

U.S. PATENT DOCUMENTS

| | | |
|---|---|---|
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0015181 A1 | 1/2006 | Elberg |
| 2006/0015183 A1 | 1/2006 | Gilbert et al. |
| 2006/0020342 A1 | 1/2006 | Ferree et al. |
| 2006/0024614 A1 | 2/2006 | Williamson |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030839 A1 | 2/2006 | Park et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036250 A1 | 2/2006 | Lange et al. |
| 2006/0036252 A1 | 2/2006 | Baynham et al. |
| 2006/0036254 A1 | 2/2006 | Lim |
| 2006/0036255 A1 | 2/2006 | Pond, Jr. et al. |
| 2006/0036256 A1 | 2/2006 | Carl et al. |
| 2006/0036258 A1 | 2/2006 | Zucherman et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0052870 A1 | 3/2006 | Ferree |
| 2006/0052872 A1 | 3/2006 | Studer et al. |
| 2006/0058788 A1 | 3/2006 | Hammer et al. |
| 2006/0058790 A1 | 3/2006 | Carl et al. |
| 2006/0058791 A1 | 3/2006 | Broman et al. |
| 2006/0058800 A1 | 3/2006 | Ainsworth et al. |
| 2006/0058878 A1 | 3/2006 | Michelson |
| 2006/0064090 A1 | 3/2006 | Park |
| 2006/0064091 A1 | 3/2006 | Ludwig et al. |
| 2006/0064092 A1 | 3/2006 | Howland |
| 2006/0064095 A1 | 3/2006 | Senn et al. |
| 2006/0069315 A1 | 3/2006 | Miles et al. |
| 2006/0069390 A1 | 3/2006 | Frigg et al. |
| 2006/0069436 A1 | 3/2006 | Sutton et al. |
| 2006/0069438 A1 | 3/2006 | Zucherman et al. |
| 2006/0074419 A1 | 4/2006 | Taylor et al. |
| 2006/0074445 A1 | 4/2006 | Gerber et al. |
| 2006/0074488 A1 | 4/2006 | Abdou et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth et al. |
| 2006/0079899 A1 | 4/2006 | Ritland |
| 2006/0079903 A1 | 4/2006 | Wong |
| 2006/0079905 A1 | 4/2006 | Beyar et al. |
| 2006/0084844 A1 | 4/2006 | Nehls |
| 2006/0084976 A1 | 4/2006 | Borgstrom et al. |
| 2006/0084977 A1 | 4/2006 | Lieberman |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084986 A1 | 4/2006 | Grinberg et al. |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085076 A1 | 4/2006 | Krishna et al. |
| 2006/0088398 A1 | 4/2006 | Lund |
| 2006/0089643 A1 | 4/2006 | Mujwid |
| 2006/0089644 A1 | 4/2006 | Felix |
| 2006/0089646 A1 | 4/2006 | Bonutti |
| 2006/0089647 A1 | 4/2006 | Culbert et al. |
| 2006/0089656 A1 | 4/2006 | Allard et al. |
| 2006/0089718 A1 | 4/2006 | Zucherman et al. |
| 2006/0095037 A1 | 5/2006 | Jones et al. |
| 2006/0106380 A1 | 5/2006 | Colleran et al. |
| 2006/0106381 A1 | 5/2006 | Ferree et al. |
| 2006/0106383 A1 | 5/2006 | Biedermann et al. |
| 2006/0106387 A1 | 5/2006 | Fanger et al. |
| 2006/0106395 A1 | 5/2006 | Link et al. |
| 2006/0106397 A1 | 5/2006 | Lins |
| 2006/0111714 A1 | 5/2006 | Foley |
| 2006/0111715 A1 | 5/2006 | Jackson |
| 2006/0111728 A1 | 5/2006 | Abdou |
| 2006/0116677 A1 | 6/2006 | Burd et al. |
| 2006/0116768 A1 | 6/2006 | Krueger et al. |
| 2006/0122597 A1 | 6/2006 | Jones et al. |
| 2006/0122599 A1 | 6/2006 | Drewry et al. |
| 2006/0122604 A1 | 6/2006 | Gorhan et al. |
| 2006/0122607 A1 | 6/2006 | Kolb |
| 2006/0122625 A1 | 6/2006 | Truckai et al. |
| 2006/0122701 A1 | 6/2006 | Kiester |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0129244 A1 | 6/2006 | Ensign |
| 2006/0136060 A1 | 6/2006 | Taylor |
| 2006/0136062 A1 | 6/2006 | Dinello et al. |
| 2006/0142758 A1 | 6/2006 | Petit |
| 2006/0142760 A1 | 6/2006 | McDonnell |
| 2006/0142761 A1 | 6/2006 | Landry et al. |
| 2006/0142858 A1 | 6/2006 | Colleran et al. |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149234 A1 | 7/2006 | De |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149244 A1 | 7/2006 | Amrein et al. |
| 2006/0149245 A1 | 7/2006 | Sweeney |
| 2006/0149278 A1 | 7/2006 | Abdou |
| 2006/0149284 A1 | 7/2006 | McCormack et al. |
| 2006/0149385 A1 | 7/2006 | McKay |
| 2006/0155277 A1 | 7/2006 | Metz-Stavenhagen |
| 2006/0155278 A1 | 7/2006 | Warnick |
| 2006/0155284 A1 | 7/2006 | Doherty et al. |
| 2006/0161152 A1 | 7/2006 | Ensign et al. |
| 2006/0161154 A1 | 7/2006 | McAfee |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0178746 A1 | 8/2006 | Bartish, Jr. et al. |
| 2006/0184112 A1 | 8/2006 | Horn et al. |
| 2006/0184171 A1 | 8/2006 | Biedermann et al. |
| 2006/0184180 A1 | 8/2006 | Augostino et al. |
| 2006/0184247 A1 | 8/2006 | Edidin et al. |
| 2006/0187562 A1 | 8/2006 | Mounnarat et al. |
| 2006/0189983 A1 | 8/2006 | Fallin et al. |
| 2006/0189984 A1 | 8/2006 | Fallin et al. |
| 2006/0189985 A1 | 8/2006 | Lewis |
| 2006/0190082 A1 | 8/2006 | Keller et al. |
| 2006/0195089 A1 | 8/2006 | Lehuec et al. |
| 2006/0195090 A1 | 8/2006 | Suddaby |
| 2006/0195093 A1 | 8/2006 | Jahng |
| 2006/0195096 A1 | 8/2006 | Lee et al. |
| 2006/0195098 A1 | 8/2006 | Schumacher |
| 2006/0195102 A1 | 8/2006 | Malandain |
| 2006/0195192 A1 | 8/2006 | Gordon et al. |
| 2006/0200121 A1 | 9/2006 | Mowery |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |

(56) References Cited

U.S. PATENT DOCUMENTS

| | | |
|---|---|---|
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman et al. |
| 2006/0212034 A1 | 9/2006 | Triplett et al. |
| 2006/0217710 A1 | 9/2006 | Abdou |
| 2006/0217712 A1 | 9/2006 | Mueller et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |
| 2006/0217731 A1 | 9/2006 | Gil et al. |
| 2006/0217809 A1 | 9/2006 | Albert et al. |
| 2006/0224159 A1 | 10/2006 | Anderson |
| 2006/0229608 A1 | 10/2006 | Foster et al. |
| 2006/0229609 A1 | 10/2006 | Wang |
| 2006/0229610 A1 | 10/2006 | Piehl |
| 2006/0229612 A1 | 10/2006 | Rothman et al. |
| 2006/0229613 A1 | 10/2006 | Timm et al. |
| 2006/0229614 A1 | 10/2006 | Foley et al. |
| 2006/0229615 A1 | 10/2006 | Abdou et al. |
| 2006/0229627 A1 | 10/2006 | Hunt et al. |
| 2006/0229715 A1 | 10/2006 | Istephanous et al. |
| 2006/0229729 A1 | 10/2006 | Gordon et al. |
| 2006/0235387 A1 | 10/2006 | Peterman |
| 2006/0235389 A1 | 10/2006 | Albert et al. |
| 2006/0235391 A1 | 10/2006 | Sutterlin, III |
| 2006/0235392 A1 | 10/2006 | Hammer et al. |
| 2006/0235393 A1 | 10/2006 | Bono et al. |
| 2006/0235403 A1 | 10/2006 | Blain |
| 2006/0235411 A1 | 10/2006 | Blain et al. |
| 2006/0235414 A1 | 10/2006 | Lim et al. |
| 2006/0235426 A1 | 10/2006 | Lim et al. |
| 2006/0235532 A1 | 10/2006 | Meunier et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241610 A1 | 10/2006 | Lim et al. |
| 2006/0241614 A1 | 10/2006 | Bruneau et al. |
| 2006/0241615 A1 | 10/2006 | Melkent |
| 2006/0241641 A1 | 10/2006 | Albans et al. |
| 2006/0241761 A1 | 10/2006 | Gately |
| 2006/0241769 A1 | 10/2006 | Gordon et al. |
| 2006/0241771 A1 | 10/2006 | Gordon et al. |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247634 A1 | 11/2006 | Warner et al. |
| 2006/0247635 A1 | 11/2006 | Gordon et al. |
| 2006/0247636 A1 | 11/2006 | Yuan et al. |
| 2006/0247637 A1 | 11/2006 | Colleran et al. |
| 2006/0247640 A1 | 11/2006 | Blackwell et al. |
| 2006/0247655 A1 | 11/2006 | Francis et al. |
| 2006/0247679 A1 | 11/2006 | Peterman |
| 2006/0247772 A1 | 11/2006 | McKay |
| 2006/0247778 A1 | 11/2006 | Ferree et al. |
| 2006/0247779 A1 | 11/2006 | Gordon et al. |
| 2006/0247782 A1 | 11/2006 | Molz, IV et al. |
| 2006/0253198 A1 | 11/2006 | Myint et al. |
| 2006/0253201 A1 | 11/2006 | McLuen |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0265077 A1 | 11/2006 | Zwirkoski |
| 2006/0269940 A1 | 11/2006 | Li et al. |
| 2006/0271046 A1 | 11/2006 | Kwak et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0276793 A1 | 12/2006 | Berry |
| 2006/0276803 A1 | 12/2006 | Salerni |
| 2006/0276900 A1 | 12/2006 | Carpenter |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282078 A1 | 12/2006 | Labrom et al. |
| 2006/0282079 A1 | 12/2006 | Labrom et al. |
| 2006/0287583 A1 | 12/2006 | Mangiardi |
| 2006/0293662 A1 | 12/2006 | Boyer, II et al. |
| 2007/0016218 A1 | 1/2007 | Winslow et al. |
| 2007/0016298 A1 | 1/2007 | Recoules-Arche et al. |
| 2007/0021836 A1 | 1/2007 | Doty |
| 2007/0027542 A1 | 2/2007 | Xu |
| 2007/0032790 A1 | 2/2007 | Aschmann et al. |
| 2007/0039837 A1 | 2/2007 | Hanina et al. |
| 2007/0043356 A1 | 2/2007 | Timm et al. |
| 2007/0043442 A1 | 2/2007 | Abernathie et al. |
| 2007/0049935 A1 | 3/2007 | Edidin et al. |
| 2007/0050030 A1 | 3/2007 | Kim |
| 2007/0050032 A1 | 3/2007 | Gittings et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073111 A1 | 3/2007 | Bass |
| 2007/0083266 A1 | 4/2007 | Lang |
| 2007/0090238 A1 | 4/2007 | Justis |
| 2007/0093817 A1 | 4/2007 | Barrus et al. |
| 2007/0093823 A1 | 4/2007 | Booth et al. |
| 2007/0093825 A1 | 4/2007 | Ferree et al. |
| 2007/0093828 A1 | 4/2007 | Abdou et al. |
| 2007/0093829 A1 | 4/2007 | Abdou |
| 2007/0093901 A1 | 4/2007 | Grotz et al. |
| 2007/0100212 A1 | 5/2007 | Pimenta et al. |
| 2007/0100340 A1 | 5/2007 | Lange et al. |
| 2007/0100341 A1 | 5/2007 | Reglos et al. |
| 2007/0106298 A1 | 5/2007 | Carli et al. |
| 2007/0106383 A1 | 5/2007 | Abdou et al. |
| 2007/0108383 A1 | 5/2007 | Combes et al. |
| 2007/0118121 A1 | 5/2007 | Purcell et al. |
| 2007/0118122 A1 | 5/2007 | Butler et al. |
| 2007/0118123 A1 | 5/2007 | Strausbaugh et al. |
| 2007/0118132 A1 | 5/2007 | Culbert et al. |
| 2007/0123867 A1 | 5/2007 | Kirschman |
| 2007/0123869 A1 | 5/2007 | Chin et al. |
| 2007/0123884 A1 | 5/2007 | Abdou |
| 2007/0129804 A1 | 6/2007 | Bentley et al. |
| 2007/0142916 A1 | 6/2007 | Olson, Jr. et al. |
| 2007/0149978 A1 | 6/2007 | Shezifi et al. |
| 2007/0151116 A1 | 7/2007 | Malandain |
| 2007/0156233 A1 | 7/2007 | Kapadia et al. |
| 2007/0161962 A1 | 7/2007 | Edie et al. |
| 2007/0161992 A1 | 7/2007 | Kwak et al. |
| 2007/0162000 A1 | 7/2007 | Perkins |
| 2007/0162001 A1 | 7/2007 | Chin et al. |
| 2007/0162005 A1 | 7/2007 | Peterson et al. |
| 2007/0162127 A1 | 7/2007 | Peterman et al. |
| 2007/0162133 A1 | 7/2007 | Doubler et al. |
| 2007/0162138 A1 | 7/2007 | Heinz |
| 2007/0167948 A1 | 7/2007 | Abdou |
| 2007/0168036 A1 | 7/2007 | Ainsworth et al. |
| 2007/0173831 A1 | 7/2007 | Abdou |
| 2007/0173842 A1 | 7/2007 | Abdou |
| 2007/0179493 A1 | 8/2007 | Kim |
| 2007/0179500 A1 | 8/2007 | Chin et al. |
| 2007/0179614 A1 | 8/2007 | Heinz et al. |
| 2007/0185367 A1 | 8/2007 | Abdou |
| 2007/0185376 A1 | 8/2007 | Wilson et al. |
| 2007/0185489 A1 | 8/2007 | Abdou |
| 2007/0191834 A1 | 8/2007 | Bruneau et al. |
| 2007/0191861 A1 | 8/2007 | Allard et al. |
| 2007/0191946 A1 | 8/2007 | Heinz et al. |
| 2007/0191951 A1 | 8/2007 | Branch, Jr. et al. |

(56) References Cited

U.S. PATENT DOCUMENTS

| | | |
|---|---|---|
| 2007/0191958 A1 | 8/2007 | Abdou |
| 2007/0198090 A1 | 8/2007 | Abdou |
| 2007/0208227 A1 | 9/2007 | Smith et al. |
| 2007/0213597 A1 | 9/2007 | Wooster |
| 2007/0213732 A1 | 9/2007 | Khanna et al. |
| 2007/0225724 A1 | 9/2007 | Edmond |
| 2007/0225726 A1 | 9/2007 | Dye et al. |
| 2007/0225807 A1 | 9/2007 | Phan et al. |
| 2007/0225808 A1 | 9/2007 | Warnick |
| 2007/0225812 A1 | 9/2007 | Gill |
| 2007/0233074 A1 | 10/2007 | Anderson et al. |
| 2007/0233077 A1 | 10/2007 | Khalili |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | Dipoto et al. |
| 2007/0233118 A1 | 10/2007 | McLain |
| 2007/0233129 A1 | 10/2007 | Bertagnoli et al. |
| 2007/0233247 A1 | 10/2007 | Schwab |
| 2007/0233251 A1 | 10/2007 | Abdou |
| 2007/0255389 A1 | 11/2007 | Oberti et al. |
| 2007/0255415 A1 | 11/2007 | Edie et al. |
| 2007/0270812 A1 | 11/2007 | Peckham |
| 2007/0270813 A1 | 11/2007 | Garamszegi |
| 2007/0270824 A1 | 11/2007 | Lim et al. |
| 2007/0270827 A1 | 11/2007 | Lim et al. |
| 2007/0270838 A1 | 11/2007 | Bruneau et al. |
| 2007/0270840 A1 | 11/2007 | Chin et al. |
| 2007/0270874 A1 | 11/2007 | Anderson |
| 2007/0270963 A1 | 11/2007 | Melkent et al. |
| 2007/0270968 A1 | 11/2007 | Baynham et al. |
| 2007/0274772 A1 | 11/2007 | Tiberghien et al. |
| 2007/0276370 A1 | 11/2007 | Altarac et al. |
| 2007/0282448 A1 | 12/2007 | Abdou |
| 2007/0293949 A1 | 12/2007 | Salerni et al. |
| 2007/0299445 A1 | 12/2007 | Shadduck et al. |
| 2007/0299521 A1 | 12/2007 | Glenn et al. |
| 2008/0009880 A1 | 1/2008 | Warnick et al. |
| 2008/0015580 A1 | 1/2008 | Chao |
| 2008/0015597 A1 | 1/2008 | Whipple |
| 2008/0015698 A1 | 1/2008 | Marino et al. |
| 2008/0021466 A1 | 1/2008 | Shadduck et al. |
| 2008/0021559 A1 | 1/2008 | Thramann |
| 2008/0027432 A1 | 1/2008 | Strauss et al. |
| 2008/0027438 A1 | 1/2008 | Abdou |
| 2008/0027458 A1 | 1/2008 | Aikins et al. |
| 2008/0027544 A1 | 1/2008 | Melkent |
| 2008/0027545 A1 | 1/2008 | Zucherman et al. |
| 2008/0027550 A1 | 1/2008 | Link et al. |
| 2008/0039837 A1 | 2/2008 | Gambale |
| 2008/0039843 A1 | 2/2008 | Abdou |
| 2008/0045963 A1 | 2/2008 | Abdou |
| 2008/0045968 A1 | 2/2008 | Yu et al. |
| 2008/0045983 A1 | 2/2008 | To et al. |
| 2008/0051783 A1 | 2/2008 | Null et al. |
| 2008/0051896 A1 | 2/2008 | Suddaby |
| 2008/0058606 A1 | 3/2008 | Miles et al. |
| 2008/0058810 A1 | 3/2008 | Abdou |
| 2008/0065219 A1 | 3/2008 | Dye |
| 2008/0065222 A1 | 3/2008 | Hamada |
| 2008/0081951 A1 | 4/2008 | Frasier et al. |
| 2008/0086080 A1 | 4/2008 | Mastri et al. |
| 2008/0091211 A1 | 4/2008 | Gately |
| 2008/0108993 A1 | 5/2008 | Bennett et al. |
| 2008/0114401 A1 | 5/2008 | Liu et al. |
| 2008/0114455 A1 | 5/2008 | Lange et al. |
| 2008/0119853 A1 | 5/2008 | Felt et al. |
| 2008/0119935 A1 | 5/2008 | Alvarez |
| 2008/0125813 A1 | 5/2008 | Erickson et al. |
| 2008/0125865 A1 | 5/2008 | Abdelgany |
| 2008/0126813 A1 | 5/2008 | Kawakami |
| 2008/0132951 A1 | 6/2008 | Reiley et al. |
| 2008/0133012 A1 | 6/2008 | McGuckin |
| 2008/0133014 A1 | 6/2008 | Gately et al. |
| 2008/0133016 A1 | 6/2008 | Heinz |
| 2008/0133017 A1 | 6/2008 | Beyar et al. |
| 2008/0139879 A1 | 6/2008 | Olson et al. |
| 2008/0140085 A1 | 6/2008 | Gately et al. |
| 2008/0140125 A1 | 6/2008 | Mitchell et al. |
| 2008/0140204 A1 | 6/2008 | Heinz |
| 2008/0140207 A1 | 6/2008 | Olmos et al. |
| 2008/0147123 A1 | 6/2008 | Schermerhorn |
| 2008/0147190 A1 | 6/2008 | Dewey et al. |
| 2008/0154308 A1 | 6/2008 | Sherman et al. |
| 2008/0154374 A1 | 6/2008 | Labrom |
| 2008/0161818 A1 | 7/2008 | Kloss et al. |
| 2008/0161821 A1 | 7/2008 | Heinz |
| 2008/0161853 A1 | 7/2008 | Arnold et al. |
| 2008/0161856 A1 | 7/2008 | Liu et al. |
| 2008/0167655 A1 | 7/2008 | Wang et al. |
| 2008/0167657 A1 | 7/2008 | Greenhalgh |
| 2008/0177271 A1 | 7/2008 | Yeh |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177326 A1 | 7/2008 | Thompson |
| 2008/0177391 A1 | 7/2008 | Mitchell et al. |
| 2008/0183204 A1 | 7/2008 | Greenhalgh et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0188898 A1 | 8/2008 | Jackson |
| 2008/0188941 A1 | 8/2008 | Grotz |
| 2008/0195152 A1 | 8/2008 | Altarac et al. |
| 2008/0234735 A1 | 9/2008 | Joshi |
| 2008/0243185 A1 | 10/2008 | Felix et al. |
| 2008/0243186 A1 | 10/2008 | Abdou |
| 2008/0243188 A1 | 10/2008 | Walder et al. |
| 2008/0243189 A1 | 10/2008 | Purcell et al. |
| 2008/0249622 A1 | 10/2008 | Gray |
| 2008/0249628 A1 | 10/2008 | Altarac et al. |
| 2008/0262318 A1 | 10/2008 | Gorek et al. |
| 2008/0262554 A1 | 10/2008 | Hayes et al. |
| 2008/0269904 A1 | 10/2008 | Voorhies |
| 2008/0281346 A1 | 11/2008 | Greenhalgh et al. |
| 2008/0281358 A1 | 11/2008 | Abdou |
| 2008/0281359 A1 | 11/2008 | Abdou |
| 2008/0288073 A1 | 11/2008 | Renganath et al. |
| 2008/0294199 A1 | 11/2008 | Kohm et al. |
| 2008/0294200 A1 | 11/2008 | Kohm et al. |
| 2008/0300598 A1 | 12/2008 | Barreiro et al. |
| 2008/0300685 A1 | 12/2008 | Carls et al. |
| 2008/0300686 A1 | 12/2008 | Khoo |
| 2008/0306601 A1 | 12/2008 | Dreyfuss |
| 2008/0312655 A1 | 12/2008 | Kirschman et al. |
| 2008/0312692 A1 | 12/2008 | Brennan et al. |
| 2008/0312741 A1 | 12/2008 | Lee et al. |
| 2008/0312743 A1 | 12/2008 | Vila et al. |
| 2008/0319487 A1 | 12/2008 | Fielding et al. |
| 2008/0319549 A1 | 12/2008 | Greenhalgh et al. |
| 2009/0012566 A1 | 1/2009 | Fauth |
| 2009/0012623 A1 | 1/2009 | Sack et al. |
| 2009/0024166 A1 | 1/2009 | Carl et al. |
| 2009/0024217 A1 | 1/2009 | Levy et al. |
| 2009/0030423 A1 | 1/2009 | Puno |
| 2009/0030457 A1 | 1/2009 | Janowski et al. |
| 2009/0030465 A1 | 1/2009 | Altarac et al. |
| 2009/0030519 A1 | 1/2009 | Falahee |
| 2009/0030520 A1 | 1/2009 | Biedermann et al. |
| 2009/0036746 A1 | 2/2009 | Blackwell et al. |
| 2009/0036927 A1 | 2/2009 | Vestgaarden |
| 2009/0036929 A1 | 2/2009 | Reglos et al. |
| 2009/0036988 A1 | 2/2009 | Peckham |
| 2009/0048668 A1 | 2/2009 | Wilson et al. |
| 2009/0054931 A1 | 2/2009 | Metz-Stavenhagen |
| 2009/0062869 A1 | 3/2009 | Claverie et al. |
| 2009/0062915 A1 | 3/2009 | Kohm et al. |
| 2009/0062918 A1 | 3/2009 | Wang et al. |
| 2009/0062920 A1 | 3/2009 | Tauber |
| 2009/0076333 A1 | 3/2009 | Bjork |
| 2009/0076516 A1 | 3/2009 | Lowry et al. |
| 2009/0076615 A1 | 3/2009 | Duggal et al. |
| 2009/0082808 A1 | 3/2009 | Butler et al. |

(56) References Cited

U.S. PATENT DOCUMENTS

| | | |
|---|---|---|
| 2009/0082813 A1 | 3/2009 | Long et al. |
| 2009/0093884 A1 | 4/2009 | Bass |
| 2009/0099601 A1 | 4/2009 | Aferzon et al. |
| 2009/0105547 A1 | 4/2009 | Vayser et al. |
| 2009/0105761 A1 | 4/2009 | Robie |
| 2009/0105768 A1 | 4/2009 | Cragg et al. |
| 2009/0105773 A1 | 4/2009 | Lange et al. |
| 2009/0105830 A1 | 4/2009 | Jones et al. |
| 2009/0105831 A1 | 4/2009 | Jones et al. |
| 2009/0118766 A1 | 5/2009 | Park et al. |
| 2009/0118771 A1 | 5/2009 | Gonzalez-Hernandez |
| 2009/0124861 A1 | 5/2009 | Fetzer |
| 2009/0125062 A1 | 5/2009 | Arnin |
| 2009/0125071 A1 | 5/2009 | Skinlo et al. |
| 2009/0132054 A1 | 5/2009 | Zeegers |
| 2009/0143859 A1 | 6/2009 | McClellan, III et al. |
| 2009/0149956 A1 | 6/2009 | Greenhalgh et al. |
| 2009/0149959 A1 | 6/2009 | Conner et al. |
| 2009/0157186 A1 | 6/2009 | Magerl |
| 2009/0157188 A1 | 6/2009 | Zeegers |
| 2009/0163920 A1 | 6/2009 | Hochschuler et al. |
| 2009/0163957 A1 | 6/2009 | St et al. |
| 2009/0163961 A1 | 6/2009 | Kirschman |
| 2009/0164020 A1 | 6/2009 | Janowski et al. |
| 2009/0171394 A1 | 7/2009 | Abdou |
| 2009/0177262 A1 | 7/2009 | Oberti et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0187249 A1 | 7/2009 | Osman |
| 2009/0192613 A1 | 7/2009 | Wing et al. |
| 2009/0192615 A1 | 7/2009 | Tyber et al. |
| 2009/0198211 A1 | 8/2009 | Thorne, Jr. et al. |
| 2009/0198277 A1 | 8/2009 | Gordon et al. |
| 2009/0204151 A1 | 8/2009 | Bracken |
| 2009/0204154 A1 | 8/2009 | Kiester |
| 2009/0204218 A1 | 8/2009 | Richelsoph |
| 2009/0204219 A1 | 8/2009 | Beaurain et al. |
| 2009/0210007 A1 | 8/2009 | Levy et al. |
| 2009/0210015 A1 | 8/2009 | Cermak et al. |
| 2009/0210062 A1 | 8/2009 | Thalgott et al. |
| 2009/0216234 A1 | 8/2009 | Farr et al. |
| 2009/0216241 A1 | 8/2009 | Dinville |
| 2009/0222046 A1 | 9/2009 | Gorek |
| 2009/0222092 A1 | 9/2009 | Davis et al. |
| 2009/0222100 A1 | 9/2009 | Cipoletti et al. |
| 2009/0227845 A1 | 9/2009 | Lo et al. |
| 2009/0228045 A1 | 9/2009 | Hayes et al. |
| 2009/0228108 A1 | 9/2009 | Keller |
| 2009/0228110 A1 | 9/2009 | McClintock |
| 2009/0234364 A1 | 9/2009 | Crook |
| 2009/0234455 A1 | 9/2009 | Moskowitz et al. |
| 2009/0240334 A1 | 9/2009 | Richelsoph |
| 2009/0240335 A1 | 9/2009 | Arcenio et al. |
| 2009/0247819 A1 | 10/2009 | Wilson et al. |
| 2009/0248078 A1 | 10/2009 | Dant |
| 2009/0248089 A1 | 10/2009 | Jacofsky et al. |
| 2009/0254125 A1 | 10/2009 | Predick |
| 2009/0259257 A1 | 10/2009 | Prevost |
| 2009/0259316 A1 | 10/2009 | Ginn |
| 2009/0265007 A1 | 10/2009 | Colleran |
| 2009/0270918 A1 | 10/2009 | Attia et al. |
| 2009/0270989 A1 | 10/2009 | Conner et al. |
| 2009/0270990 A1 | 10/2009 | Louis et al. |
| 2009/0276040 A1 | 11/2009 | Rowe et al. |
| 2009/0276049 A1 | 11/2009 | Weiland |
| 2009/0281628 A1 | 11/2009 | Oglaza et al. |
| 2009/0290316 A1 | 11/2009 | Kariya |
| 2009/0292361 A1 | 11/2009 | Lopez |
| 2009/0299478 A1 | 12/2009 | Carls et al. |
| 2009/0326538 A1 | 12/2009 | Sennett et al. |
| 2009/0326581 A1 | 12/2009 | Galley et al. |
| 2009/0326584 A1 | 12/2009 | Slivka et al. |
| 2010/0004664 A1 | 1/2010 | Boyajian et al. |
| 2010/0009929 A1 | 1/2010 | Cheng et al. |
| 2010/0016897 A1 | 1/2010 | Le et al. |
| 2010/0016906 A1 | 1/2010 | Abdou |
| 2010/0023061 A1 | 1/2010 | Randol et al. |
| 2010/0023064 A1 | 1/2010 | Brunger et al. |
| 2010/0036423 A1 | 2/2010 | Hayes et al. |
| 2010/0036495 A1 | 2/2010 | Daum et al. |
| 2010/0042149 A1 | 2/2010 | Chao et al. |
| 2010/0049324 A1 | 2/2010 | Valdevit et al. |
| 2010/0069929 A1 | 3/2010 | Abdou |
| 2010/0069962 A1 | 3/2010 | Harms et al. |
| 2010/0069965 A1 | 3/2010 | Abdou |
| 2010/0070041 A1 | 3/2010 | Peterman et al. |
| 2010/0076448 A1 | 3/2010 | Abdou |
| 2010/0082109 A1 | 4/2010 | Greenhalgh et al. |
| 2010/0087858 A1 | 4/2010 | Abdou |
| 2010/0087869 A1 | 4/2010 | Abdou |
| 2010/0087878 A1 | 4/2010 | Abdou |
| 2010/0087923 A1 | 4/2010 | Abdou |
| 2010/0094422 A1 | 4/2010 | Hansell et al. |
| 2010/0100137 A1 | 4/2010 | Justis et al. |
| 2010/0106250 A1 | 4/2010 | Abdou |
| 2010/0121384 A1 | 5/2010 | Abdou |
| 2010/0130827 A1 | 5/2010 | Pimenta et al. |
| 2010/0152778 A1 | 6/2010 | Saint |
| 2010/0174315 A1 | 7/2010 | Scodary et al. |
| 2010/0179657 A1 | 7/2010 | Greenhalgh et al. |
| 2010/0185291 A1 | 7/2010 | Jimenez et al. |
| 2010/0191336 A1 | 7/2010 | Greenhalgh |
| 2010/0191337 A1 | 7/2010 | Zamani et al. |
| 2010/0204795 A1 | 8/2010 | Greenhalgh |
| 2010/0211101 A1 | 8/2010 | Blackwell et al. |
| 2010/0211176 A1 | 8/2010 | Greenhalgh |
| 2010/0211177 A1 | 8/2010 | Abdou |
| 2010/0217382 A1 | 8/2010 | Chau et al. |
| 2010/0222644 A1 | 9/2010 | Sebastian et al. |
| 2010/0222816 A1 | 9/2010 | Gabelberger et al. |
| 2010/0222884 A1 | 9/2010 | Greenhalgh et al. |
| 2010/0234889 A1 | 9/2010 | Hess |
| 2010/0234952 A1 | 9/2010 | Peterman |
| 2010/0234956 A1 | 9/2010 | Attia et al. |
| 2010/0241168 A1 | 9/2010 | Franck et al. |
| 2010/0249933 A1 | 9/2010 | Trieu |
| 2010/0256759 A1 | 10/2010 | Hansell et al. |
| 2010/0256760 A1 | 10/2010 | Hansell |
| 2010/0262245 A1 | 10/2010 | Alfaro et al. |
| 2010/0262248 A1 | 10/2010 | Sournac et al. |
| 2010/0268281 A1 | 10/2010 | Abdou |
| 2010/0280622 A1 | 11/2010 | McKinley |
| 2010/0286483 A1 | 11/2010 | Bettuchi et al. |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0305705 A1 | 12/2010 | Butler et al. |
| 2010/0312282 A1 | 12/2010 | Abdou |
| 2010/0312347 A1 | 12/2010 | Arramon et al. |
| 2010/0318128 A1 | 12/2010 | Abdou |
| 2010/0331883 A1 | 12/2010 | Schmitz et al. |
| 2010/0331887 A1 | 12/2010 | Jackson et al. |
| 2010/0331889 A1 | 12/2010 | Abdou |
| 2010/0331981 A1 | 12/2010 | Mohammed |
| 2010/0331985 A1 | 12/2010 | Gordon et al. |
| 2011/0004248 A1 | 1/2011 | Abdou |
| 2011/0009969 A1 | 1/2011 | Puno |
| 2011/0009970 A1 | 1/2011 | Puno |
| 2011/0022090 A1 | 1/2011 | Gordon et al. |
| 2011/0029083 A1 | 2/2011 | Hynes et al. |
| 2011/0029085 A1 | 2/2011 | Hynes et al. |
| 2011/0035011 A1 | 2/2011 | Cain |
| 2011/0046679 A1 | 2/2011 | Chow et al. |
| 2011/0046740 A1 | 2/2011 | Chen et al. |
| 2011/0054531 A1 | 3/2011 | Lamborne et al. |
| 2011/0060366 A1 | 3/2011 | Heim et al. |
| 2011/0066186 A1 | 3/2011 | Boyer, II et al. |
| 2011/0082551 A1 | 4/2011 | Kraus |
| 2011/0082553 A1 | 4/2011 | Abdou |
| 2011/0093074 A1 | 4/2011 | Glerum et al. |
| 2011/0098749 A1 | 4/2011 | Boomer et al. |
| 2011/0106163 A1 | 5/2011 | Hochschuler et al. |
| 2011/0106259 A1 | 5/2011 | Lindenmann et al. |

(56) References Cited

U.S. PATENT DOCUMENTS

| | | |
|---|---|---|
| 2011/0118552 A1 | 5/2011 | Fischvogt |
| 2011/0125266 A1 | 5/2011 | Rodgers et al. |
| 2011/0130793 A1 | 6/2011 | Woolley et al. |
| 2011/0137353 A1 | 6/2011 | Buttermann |
| 2011/0144692 A1 | 6/2011 | Saladin et al. |
| 2011/0166600 A1 | 7/2011 | Lamborne et al. |
| 2011/0172720 A1 | 7/2011 | Metcalf, Jr. et al. |
| 2011/0172772 A1 | 7/2011 | Abdou |
| 2011/0184471 A1 | 7/2011 | Foley et al. |
| 2011/0190825 A1 | 8/2011 | Thalgott et al. |
| 2011/0196492 A1 | 8/2011 | Lambrecht et al. |
| 2011/0213465 A1 | 9/2011 | Landry et al. |
| 2011/0224496 A1 | 9/2011 | Weiman |
| 2011/0224497 A1 | 9/2011 | Weiman et al. |
| 2011/0238181 A1 | 9/2011 | Trieu |
| 2011/0251693 A1* | 10/2011 | Barreiro ................ A61F 2/442 623/17.16 |
| 2011/0264218 A1 | 10/2011 | Asaad |
| 2011/0264228 A1 | 10/2011 | Johnson et al. |
| 2011/0276099 A1 | 11/2011 | Champagne et al. |
| 2011/0276142 A1 | 11/2011 | Niemiec et al. |
| 2011/0282459 A1 | 11/2011 | Mcclellan, III et al. |
| 2011/0288588 A1 | 11/2011 | Chin et al. |
| 2011/0288594 A1 | 11/2011 | Woolley et al. |
| 2011/0288644 A1 | 11/2011 | Gray et al. |
| 2011/0288645 A1 | 11/2011 | Braddock, Jr. et al. |
| 2011/0301710 A1 | 12/2011 | Mather et al. |
| 2011/0301712 A1 | 12/2011 | Palmatier et al. |
| 2011/0307011 A1 | 12/2011 | Moskowitz et al. |
| 2011/0307012 A1 | 12/2011 | Mir et al. |
| 2011/0319995 A1 | 12/2011 | Voellmicke et al. |
| 2012/0010472 A1 | 1/2012 | Spann |
| 2012/0010658 A1 | 1/2012 | Kirschman |
| 2012/0016481 A1 | 1/2012 | Zwirkoski |
| 2012/0029565 A1 | 2/2012 | Seifert et al. |
| 2012/0029639 A1 | 2/2012 | Blackwell et al. |
| 2012/0035424 A1 | 2/2012 | Schulte |
| 2012/0041272 A1 | 2/2012 | Dietze, Jr. et al. |
| 2012/0071980 A1 | 3/2012 | Purcell et al. |
| 2012/0078301 A1 | 3/2012 | Hess |
| 2012/0089184 A1 | 4/2012 | Yeh |
| 2012/0095512 A1 | 4/2012 | Nihalani |
| 2012/0101528 A1 | 4/2012 | Souza et al. |
| 2012/0136442 A1 | 5/2012 | Kleiner |
| 2012/0150229 A1 | 6/2012 | Hess |
| 2012/0150302 A1 | 6/2012 | Gray |
| 2012/0158060 A1 | 6/2012 | Abrahams et al. |
| 2012/0158140 A1 | 6/2012 | Miller et al. |
| 2012/0158150 A1 | 6/2012 | Siegal |
| 2012/0179260 A1 | 7/2012 | Nottingham |
| 2012/0185045 A1 | 7/2012 | Morris et al. |
| 2012/0190933 A1 | 7/2012 | Kleyman |
| 2012/0191135 A1 | 7/2012 | Abdou |
| 2012/0197297 A1 | 8/2012 | Bootwala et al. |
| 2012/0197401 A1 | 8/2012 | Duncan et al. |
| 2012/0197402 A1 | 8/2012 | Blackwell et al. |
| 2012/0203279 A1 | 8/2012 | Walters et al. |
| 2012/0209271 A1 | 8/2012 | Cohen et al. |
| 2012/0209383 A1 | 8/2012 | Tsuang et al. |
| 2012/0215316 A1 | 8/2012 | Mohr et al. |
| 2012/0221049 A1 | 8/2012 | Blain et al. |
| 2012/0226313 A1 | 9/2012 | Dace |
| 2012/0232592 A1 | 9/2012 | Massoudi |
| 2012/0232658 A1 | 9/2012 | Morgenstern et al. |
| 2012/0238825 A1 | 9/2012 | Smith |
| 2012/0245425 A1 | 9/2012 | Okoniewski |
| 2012/0245431 A1 | 9/2012 | Baudouin et al. |
| 2012/0245432 A1 | 9/2012 | Karpowicz et al. |
| 2012/0245704 A1 | 9/2012 | Childs et al. |
| 2012/0253393 A1 | 10/2012 | Fiorella |
| 2012/0253396 A1 | 10/2012 | Stern et al. |
| 2012/0259416 A1 | 10/2012 | Blackwell et al. |
| 2012/0265021 A1 | 10/2012 | Nottmeier |
| 2012/0271119 A1 | 10/2012 | White |
| 2012/0277864 A1 | 11/2012 | Brodke et al. |
| 2012/0283521 A1 | 11/2012 | Smith et al. |
| 2012/0290017 A1 | 11/2012 | Haidukewych |
| 2012/0290096 A1 | 11/2012 | Messerli |
| 2012/0296171 A1 | 11/2012 | Lovell et al. |
| 2012/0296377 A1 | 11/2012 | Ferree et al. |
| 2013/0018467 A1 | 1/2013 | Suh |
| 2013/0023933 A1 | 1/2013 | Haas |
| 2013/0023937 A1 | 1/2013 | Biedermann et al. |
| 2013/0030467 A1 | 1/2013 | Karas et al. |
| 2013/0030469 A1 | 1/2013 | Karas et al. |
| 2013/0030470 A1 | 1/2013 | Karas et al. |
| 2013/0041471 A1 | 2/2013 | Siegal et al. |
| 2013/0053896 A1 | 2/2013 | Voyadzis |
| 2013/0060284 A1 | 3/2013 | Abdou |
| 2013/0066374 A1 | 3/2013 | Galley et al. |
| 2013/0079883 A1 | 3/2013 | Butler et al. |
| 2013/0090691 A1 | 4/2013 | Zhang et al. |
| 2013/0103088 A1 | 4/2013 | Karahalios et al. |
| 2013/0103089 A1 | 4/2013 | Gordon et al. |
| 2013/0123849 A1 | 5/2013 | Abdou |
| 2013/0131738 A1 | 5/2013 | Powell et al. |
| 2013/0144339 A1 | 6/2013 | Choi et al. |
| 2013/0144340 A1 | 6/2013 | Sheffer et al. |
| 2013/0150886 A1 | 6/2013 | Altarac et al. |
| 2013/0150970 A1 | 6/2013 | Thaiyananthan |
| 2013/0158359 A1 | 6/2013 | Predick et al. |
| 2013/0165982 A1 | 6/2013 | Ek et al. |
| 2013/0172932 A1 | 7/2013 | Altarac et al. |
| 2013/0172933 A1 | 7/2013 | Altarac et al. |
| 2013/0172934 A1 | 7/2013 | Walker et al. |
| 2013/0184752 A1 | 7/2013 | Binder |
| 2013/0184758 A1 | 7/2013 | Karim |
| 2013/0190573 A1 | 7/2013 | Smith |
| 2013/0190575 A1 | 7/2013 | Mast et al. |
| 2013/0204091 A1 | 8/2013 | Menendez et al. |
| 2013/0218166 A1 | 8/2013 | Elmore |
| 2013/0226240 A1 | 8/2013 | Abdou |
| 2013/0245383 A1 | 9/2013 | Friedrich et al. |
| 2013/0253585 A1 | 9/2013 | Garcia et al. |
| 2013/0253586 A1 | 9/2013 | Rathbun et al. |
| 2013/0261401 A1 | 10/2013 | Hawkins et al. |
| 2013/0261666 A1 | 10/2013 | Gundanna |
| 2013/0274883 A1 | 10/2013 | McLuen et al. |
| 2013/0274884 A1 | 10/2013 | Matsumoto et al. |
| 2013/0296939 A1 | 11/2013 | Perkins |
| 2013/0296940 A1 | 11/2013 | Northcutt et al. |
| 2013/0310942 A1 | 11/2013 | Abdou |
| 2013/0325128 A1 | 12/2013 | Perloff et al. |
| 2014/0005484 A1 | 1/2014 | Charles |
| 2014/0031874 A1 | 1/2014 | Kucharzyk et al. |
| 2014/0058512 A1 | 2/2014 | Petersheim |
| 2014/0081331 A1 | 3/2014 | Zappacosta et al. |
| 2014/0107783 A1 | 4/2014 | Abdou |
| 2014/0114137 A1 | 4/2014 | Reglos et al. |
| 2014/0114138 A1 | 4/2014 | Fedorov et al. |
| 2014/0114139 A1 | 4/2014 | Ziolo et al. |
| 2014/0135584 A1 | 5/2014 | Lee et al. |
| 2014/0148652 A1 | 5/2014 | Weiman |
| 2014/0148856 A1 | 5/2014 | Ibarra et al. |
| 2014/0155939 A1 | 6/2014 | Sugawara |
| 2014/0172002 A1 | 6/2014 | Predick |
| 2014/0172105 A1 | 6/2014 | Frasier et al. |
| 2014/0172107 A1 | 6/2014 | Thirugnanasambandam et al. |
| 2014/0188223 A1 | 7/2014 | Jensen et al. |
| 2014/0188233 A1 | 7/2014 | Mutchler et al. |
| 2014/0249631 A1 | 9/2014 | Weiman |
| 2014/0257466 A1 | 9/2014 | Board et al. |
| 2014/0277143 A1 | 9/2014 | Zappacosta |
| 2014/0277486 A1 | 9/2014 | Abdou |
| 2014/0277490 A1 | 9/2014 | Perloff et al. |
| 2014/0277499 A1 | 9/2014 | Ainsworth et al. |
| 2014/0277502 A1 | 9/2014 | Schiffman et al. |
| 2014/0288480 A1 | 9/2014 | Zimmerman et al. |
| 2014/0309741 A1 | 10/2014 | Ganter et al. |
| 2014/0336471 A1 | 11/2014 | Pfabe et al. |
| 2014/0343608 A1 | 11/2014 | Whiton et al. |
| 2014/0343678 A1 | 11/2014 | Suddaby et al. |
| 2014/0350347 A1 | 11/2014 | Karpowicz et al. |
| 2014/0379032 A1 | 12/2014 | Hennard |

(56) References Cited

U.S. PATENT DOCUMENTS

| | | | |
|---|---|---|---|
| 2014/0379086 A1 | 12/2014 | Elahinia et al. | |
| 2015/0018829 A1 | 1/2015 | Woodburn, Sr. et al. | |
| 2015/0057755 A1 | 2/2015 | Suddaby et al. | |
| 2015/0080973 A1 | 3/2015 | Eastlack | |
| 2015/0094814 A1* | 4/2015 | Emerick | A61F 2/4611 623/17.16 |
| 2015/0190242 A1 | 7/2015 | Blain et al. | |
| 2015/0202053 A1 | 7/2015 | Willis et al. | |
| 2015/0305785 A1 | 10/2015 | Taber et al. | |
| 2015/0313585 A1 | 11/2015 | Abidin et al. | |
| 2015/0313650 A1 | 11/2015 | Taber et al. | |
| 2015/0351738 A1 | 12/2015 | Perrow | |
| 2015/0351925 A1 | 12/2015 | Emerick et al. | |
| 2015/0359640 A1 | 12/2015 | Taber et al. | |
| 2016/0000419 A1 | 1/2016 | Weisshaupt et al. | |
| 2016/0030030 A1 | 2/2016 | Bass | |
| 2016/0045333 A1 | 2/2016 | Baynham | |
| 2016/0081681 A1 | 3/2016 | Waugh et al. | |
| 2016/0089247 A1* | 3/2016 | Nichols | A61F 2/30767 623/17.16 |
| 2016/0103689 A1 | 4/2016 | Sanghi et al. | |
| 2016/0213443 A1 | 7/2016 | Lueck et al. | |
| 2016/0270772 A1 | 9/2016 | Beale et al. | |
| 2016/0287236 A1 | 10/2016 | Garcia-Bengochea et al. | |
| 2016/0310294 A1 | 10/2016 | McConnell et al. | |
| 2016/0317323 A1 | 11/2016 | Cho et al. | |
| 2016/0317324 A1 | 11/2016 | Cho et al. | |
| 2016/0354210 A1 | 12/2016 | Tran | |
| 2016/0361177 A1 | 12/2016 | Biedermann et al. | |
| 2017/0007226 A1 | 1/2017 | Fehling | |
| 2017/0014117 A1 | 1/2017 | Capote | |
| 2017/0042527 A1 | 2/2017 | Farley et al. | |
| 2017/0056194 A1 | 3/2017 | Biedermann et al. | |
| 2017/0065269 A1 | 3/2017 | Thommen et al. | |
| 2017/0112635 A1 | 4/2017 | Ty et al. | |
| 2017/0143325 A1 | 5/2017 | Lynn et al. | |
| 2017/0172759 A1 | 6/2017 | Kukkar et al. | |
| 2017/0172760 A1 | 6/2017 | Loebl et al. | |
| 2017/0231613 A1 | 8/2017 | Casey et al. | |
| 2017/0245997 A1 | 8/2017 | Trischler | |
| 2017/0340451 A1 | 11/2017 | McCormack et al. | |
| 2018/0021149 A1 | 1/2018 | Boehm et al. | |
| 2018/0085105 A1 | 3/2018 | Kim | |
| 2018/0206834 A1 | 7/2018 | Villamil et al. | |
| 2018/0235724 A1 | 8/2018 | Nowatschin et al. | |
| 2018/0249992 A1 | 9/2018 | Truckey | |
| 2018/0256363 A1 | 9/2018 | Moon | |
| 2018/0289506 A1 | 10/2018 | Kim et al. | |
| 2018/0303624 A1 | 10/2018 | Shoshtaev | |
| 2018/0310927 A1 | 11/2018 | Garcia-Bengochea et al. | |
| 2018/0333061 A1 | 11/2018 | Pracyk et al. | |
| 2018/0344481 A1 | 12/2018 | Garcia-Bengochea | |
| 2018/0360621 A1 | 12/2018 | Moon | |
| 2019/0192312 A1 | 6/2019 | Ullrich, Jr. et al. | |
| 2019/0209154 A1 | 7/2019 | Richter et al. | |
| 2019/0216450 A1 | 7/2019 | Bjork et al. | |
| 2019/0216453 A1 | 7/2019 | Predick et al. | |
| 2019/0307439 A1 | 10/2019 | Chhit et al. | |
| 2019/0321022 A1 | 10/2019 | Karpowicz et al. | |
| 2020/0085530 A1 | 3/2020 | Sauer | |
| 2020/0113713 A1 | 4/2020 | LaMarca et al. | |

FOREIGN PATENT DOCUMENTS

| | | |
|---|---|---|
| DE | 29911422 U1 | 8/1999 |
| DE | 1003518 A1 | 2/2002 |
| DE | 20320454 U1 | 10/2004 |
| DE | 10323363 A1 | 12/2004 |
| EP | 0077159 A1 | 4/1983 |
| EP | 0274713 A1 | 7/1988 |
| EP | 0301489 A1 | 2/1989 |
| EP | 0317972 A1 | 5/1989 |
| EP | 0333990 A2 | 9/1989 |
| EP | 0356112 A1 | 2/1990 |
| EP | 0418387 A1 | 3/1991 |
| EP | 0512529 A1 | 11/1992 |
| EP | 0560141 A1 | 9/1993 |
| EP | 0566810 A1 | 10/1993 |
| EP | 0611116 A1 | 8/1994 |
| EP | 0614649 A1 | 9/1994 |
| EP | 0637439 A1 | 2/1995 |
| EP | 0697200 A1 | 2/1996 |
| EP | 0611116 B1 | 7/1996 |
| EP | 0566810 B1 | 8/1996 |
| EP | 0747025 A1 | 12/1996 |
| EP | 0951879 A2 | 10/1999 |
| EP | 0955021 A1 | 11/1999 |
| EP | 0965313 A1 | 12/1999 |
| EP | 1180348 A2 | 2/2002 |
| EP | 1192910 A2 | 4/2002 |
| EP | 1222903 A1 | 7/2002 |
| EP | 1254640 A2 | 11/2002 |
| EP | 1287795 A1 | 3/2003 |
| EP | 1442715 A2 | 8/2004 |
| EP | 1504733 A1 | 2/2005 |
| EP | 1374808 B1 | 12/2005 |
| EP | 1758511 A2 | 3/2007 |
| EP | 1848352 A2 | 10/2007 |
| EP | 1872731 A1 | 1/2008 |
| EP | 1942816 A2 | 7/2008 |
| EP | 1942838 A2 | 7/2008 |
| EP | 1980222 A1 | 10/2008 |
| EP | 1389978 B1 | 1/2009 |
| EP | 2032086 A2 | 3/2009 |
| EP | 2101691 A2 | 9/2009 |
| EP | 2113228 A1 | 11/2009 |
| EP | 2327375 A1 | 6/2011 |
| EP | 2340788 A1 | 7/2011 |
| EP | 2363080 A1 | 9/2011 |
| EP | 2131790 B1 | 10/2012 |
| EP | 3111896 A1 | 1/2017 |
| FR | 1037262 A | 9/1953 |
| FR | 2124815 A5 | 9/1972 |
| FR | 2632516 A1 | 12/1989 |
| FR | 2659226 A1 | 9/1991 |
| FR | 2703239 A1 | 10/1994 |
| FR | 2703580 A1 | 10/1994 |
| FR | 2723841 A1 | 3/1996 |
| FR | 2724108 A1 | 3/1996 |
| FR | 2730159 A1 | 8/1996 |
| FR | 2733413 A1 | 10/1996 |
| FR | 2747034 A1 | 10/1997 |
| FR | 2781359 A1 | 1/2000 |
| FR | 2787021 A1 | 6/2000 |
| FR | 2788958 A1 | 8/2000 |
| FR | 2806614 A1 | 9/2001 |
| FR | 2808995 A1 | 11/2001 |
| FR | 2813782 A1 | 3/2002 |
| FR | 2824261 A1 | 11/2002 |
| FR | 2827156 A1 | 1/2003 |
| FR | 2831796 A1 | 5/2003 |
| FR | 2846550 A1 | 5/2004 |
| FR | 2856271 A1 | 12/2004 |
| FR | 2861582 A1 | 5/2005 |
| FR | 2865629 A1 | 8/2005 |
| FR | 2879436 A1 | 6/2006 |
| FR | 2880795 A1 | 7/2006 |
| FR | 2887762 A1 | 1/2007 |
| FR | 2891135 A1 | 3/2007 |
| FR | 2893838 A1 | 6/2007 |
| FR | 2897259 A1 | 8/2007 |
| FR | 2902639 A1 | 12/2007 |
| FR | 2916956 A1 | 12/2008 |
| FR | 2930718 A1 | 11/2009 |
| GB | 780652 A | 8/1957 |
| GB | 2178323 A | 2/1987 |
| JP | H02261446 A | 10/1990 |
| JP | H0998983 A | 4/1997 |
| WO | WO-9000037 A1 | 1/1990 |
| WO | WO-9107931 A1 | 6/1991 |
| WO | WO-9301771 A1 | 2/1993 |
| WO | WO-9307823 A1 | 4/1993 |
| WO | WO-9314721 A1 | 8/1993 |

(56) References Cited

FOREIGN PATENT DOCUMENTS

| | | |
|---|---|---|
| WO | WO-9404100 A1 | 3/1994 |
| WO | WO-9420048 A1 | 9/1994 |
| WO | WO-9508306 A1 | 3/1995 |
| WO | WO-9510240 A1 | 4/1995 |
| WO | WO-9515133 A1 | 6/1995 |
| WO | WO-9525474 A1 | 9/1995 |
| WO | WO-9715248 A1 | 5/1997 |
| WO | WO-9723174 A1 | 7/1997 |
| WO | WO-9730666 A2 | 8/1997 |
| WO | WO-9737620 A1 | 10/1997 |
| WO | WO-9801091 A1 | 1/1998 |
| WO | WO-9817209 A2 | 4/1998 |
| WO | WO-9855052 A1 | 12/1998 |
| WO | WO-9900065 A1 | 1/1999 |
| WO | WO-9904718 A1 | 2/1999 |
| WO | WO-9909914 A1 | 3/1999 |
| WO | WO-9921500 A1 | 5/1999 |
| WO | WO-9921502 A1 | 5/1999 |
| WO | WO-9933405 A1 | 7/1999 |
| WO | WO-9938463 A2 | 8/1999 |
| WO | WO-9953871 A1 | 10/1999 |
| WO | WO-9956653 A1 | 11/1999 |
| WO | WO-9956675 A1 | 11/1999 |
| WO | WO-9956676 A1 | 11/1999 |
| WO | WO-9963914 A1 | 12/1999 |
| WO | WO-9965412 A1 | 12/1999 |
| WO | WO-9966864 A1 | 12/1999 |
| WO | WO-0015125 A1 | 3/2000 |
| WO | WO-0018312 A1 | 4/2000 |
| WO | WO-0023015 A1 | 4/2000 |
| WO | WO-0024325 A1 | 5/2000 |
| WO | WO-0024327 A2 | 5/2000 |
| WO | WO-0053127 A1 | 9/2000 |
| WO | WO-0064362 A1 | 11/2000 |
| WO | WO-0072770 A1 | 12/2000 |
| WO | WO-0074606 A1 | 12/2000 |
| WO | WO-0078238 A1 | 12/2000 |
| WO | WO-0101874 A1 | 1/2001 |
| WO | WO-0103592 A1 | 1/2001 |
| WO | WO-0106940 A1 | 2/2001 |
| WO | WO-0119295 A1 | 3/2001 |
| WO | WO-0126566 A1 | 4/2001 |
| WO | WO-0128465 A2 | 4/2001 |
| WO | WO-0141680 A1 | 6/2001 |
| WO | WO-0143620 A2 | 6/2001 |
| WO | WO-0145577 A2 | 6/2001 |
| WO | WO-0160270 A1 | 8/2001 |
| WO | WO-0162191 A2 | 8/2001 |
| WO | WO-0170141 A1 | 9/2001 |
| WO | WO-0187194 A1 | 11/2001 |
| WO | WO-0211633 A2 | 2/2002 |
| WO | WO-0213732 A2 | 2/2002 |
| WO | WO-0228299 A1 | 4/2002 |
| WO | WO-0230307 A2 | 4/2002 |
| WO | WO-02051326 A1 | 7/2002 |
| WO | WO-02058599 A2 | 8/2002 |
| WO | WO-02058600 A2 | 8/2002 |
| WO | WO-02071960 A1 | 9/2002 |
| WO | WO-02076315 A1 | 10/2002 |
| WO | WO-02080788 A1 | 10/2002 |
| WO | WO-02089701 A2 | 11/2002 |
| WO | WO-03005939 A2 | 1/2003 |
| WO | WO-03007829 A1 | 1/2003 |
| WO | WO-03015646 A2 | 2/2003 |
| WO | WO-03024298 A2 | 3/2003 |
| WO | WO-03026522 A2 | 4/2003 |
| WO | WO-03032850 A1 | 4/2003 |
| WO | WO-03032851 A1 | 4/2003 |
| WO | WO-03037200 A2 | 5/2003 |
| WO | WO-03039400 A2 | 5/2003 |
| WO | WO-03045262 A2 | 6/2003 |
| WO | WO-03049629 A1 | 6/2003 |
| WO | WO-03051212 A2 | 6/2003 |
| WO | WO-03059212 A1 | 7/2003 |
| WO | WO-03075803 A1 | 9/2003 |
| WO | WO-03075804 A1 | 9/2003 |
| WO | WO-2004016217 A2 | 2/2004 |
| WO | WO-2004032726 A2 | 4/2004 |
| WO | WO-2004034935 A1 | 4/2004 |
| WO | WO-2004039283 A2 | 5/2004 |
| WO | WO-2004039291 A1 | 5/2004 |
| WO | WO-2004041129 A1 | 5/2004 |
| WO | WO-2004049915 A2 | 6/2004 |
| WO | WO-2004062482 A2 | 7/2004 |
| WO | WO-2004084774 A1 | 10/2004 |
| WO | WO-2004093702 A2 | 11/2004 |
| WO | WO-2004105577 A2 | 12/2004 |
| WO | WO-2005007040 A1 | 1/2005 |
| WO | WO-2005009262 A2 | 2/2005 |
| WO | WO-2005011522 A2 | 2/2005 |
| WO | WO-2005020829 A1 | 3/2005 |
| WO | WO-2005044119 A2 | 5/2005 |
| WO | WO-2005046534 A1 | 5/2005 |
| WO | WO-2005051243 A2 | 6/2005 |
| WO | WO-2005074839 A1 | 8/2005 |
| WO | WO-2005077288 A1 | 8/2005 |
| WO | WO-2005104996 A1 | 11/2005 |
| WO | WO-2005117728 A1 | 12/2005 |
| WO | WO-2005122922 A2 | 12/2005 |
| WO | WO-2006016384 A1 | 2/2006 |
| WO | WO-2006041963 A2 | 4/2006 |
| WO | WO-2006042335 A1 | 4/2006 |
| WO | WO-2006045089 A2 | 4/2006 |
| WO | WO-2006047587 A2 | 5/2006 |
| WO | WO-2006058221 A2 | 6/2006 |
| WO | WO-2006062960 A2 | 6/2006 |
| WO | WO-2006086241 A2 | 8/2006 |
| WO | WO-2006089292 A2 | 8/2006 |
| WO | WO-2006096756 A2 | 9/2006 |
| WO | WO-2006106268 A2 | 10/2006 |
| WO | WO-2006110578 A2 | 10/2006 |
| WO | WO-2006120505 A1 | 11/2006 |
| WO | WO-2006130460 A2 | 12/2006 |
| WO | WO-2006136760 A2 | 12/2006 |
| WO | WO-2007000634 A1 | 1/2007 |
| WO | WO-2007000654 A2 | 1/2007 |
| WO | WO-2007034310 A1 | 3/2007 |
| WO | WO-2007038475 A2 | 4/2007 |
| WO | WO-2007041648 A2 | 4/2007 |
| WO | WO-2007044705 A2 | 4/2007 |
| WO | WO-2007044836 A2 | 4/2007 |
| WO | WO-2007056516 A2 | 5/2007 |
| WO | WO-2007059207 A2 | 5/2007 |
| WO | WO-2007063398 A2 | 6/2007 |
| WO | WO-2007078978 A2 | 7/2007 |
| WO | WO-2007087535 A2 | 8/2007 |
| WO | WO-2007089975 A1 | 8/2007 |
| WO | WO-2007093900 A2 | 8/2007 |
| WO | WO-2007095333 A2 | 8/2007 |
| WO | WO-2007106573 A2 | 9/2007 |
| WO | WO-2007075843 A3 | 12/2007 |
| WO | WO-2007140382 A2 | 12/2007 |
| WO | WO-2008013960 A2 | 1/2008 |
| WO | WO-2008021319 A2 | 2/2008 |
| WO | WO-2008024373 A2 | 2/2008 |
| WO | WO-2008067452 A1 | 6/2008 |
| WO | WO-2008073447 A2 | 6/2008 |
| WO | WO-2008082836 A1 | 7/2008 |
| WO | WO-2008085521 A1 | 7/2008 |
| WO | WO-2008099277 A2 | 8/2008 |
| WO | WO-2008106140 A2 | 9/2008 |
| WO | WO-2008131084 A2 | 10/2008 |
| WO | WO-2008149223 A2 | 12/2008 |
| WO | WO-2009033100 A1 | 3/2009 |
| WO | WO-2009064787 A2 | 5/2009 |
| WO | WO-2009135208 A1 | 11/2009 |
| WO | WO-2009152126 A1 | 12/2009 |

(56) References Cited

FOREIGN PATENT DOCUMENTS

| WO | WO-2010057980 A1 | 5/2010 |
|----|------------------|--------|
| WO | WO-2013006830 A1 | 1/2013 |

OTHER PUBLICATIONS

Abstract for French Patent Publication FR2781359, Published Jan. 28, 2000, entitled: "Osteosynthesis Frame for Spinal Surgery has Rod with Clamps to Hold Cross Bars with Anchor Screws". Accession No. 9867555 (Derwent Information Ltd.).
Abstract for French Patent Publication FR2856271, Published Dec. 24, 2004, Osteo-Synthesis Vertebral Column Plate, has Connection Head Integrated with Plate and Movable in Three Directions of Space So as to Adapt itself to Connection Rod, and Including Opening to Facilitate Introduction of Rod. Accession No. 14694557, (Derwent Information Ltd.).
Abstract for German Patent No. DE10035182. (Derwent Information Ltd.), publication date Feb. 7, 2002.
Andersen T., et al., "Pain 5 years After Instrumented and Non-Instrumented Posterolateral Lumbar Spinal Fusion," European Spine Journal, 2003, vol. 12 (4), pp. 393-399.
Asazuma T., et al., "Intersegmental Spinal Flexibility With Lumbosacral Instrumentation. An In Vitro Biomechanical Investigation," Spine (Phila Pa 1976), 1990, vol. 15 (11), pp. 1153-1158.
Balderston R.A., et al., "Technique for Achievement and Maintenance of Reduction for Severe Spondylolisthesis Using Spinous Process Traction Wiring and External Fixation of the Pelvis," Spine (Phila Pa 1976), 1985, vol. 10 (4), pp. 376-382.
Barbre C.J.,, "Devices for Targeting the Needle," Neurosurgery Clinics of North America, 2009, vol. 20 (2), pp. 187-191.
Bendo J.A., et al., "Instrumented Posterior Arthrodesis of the Lumbar Spine in Patients with Diabetes Mellitus," American Journal of Orthopedics (Belle Mead, NJ), 2000, vol. 29 (8), pp. 617-620.
Benz R.J., et al., "Current Techniques of Decompression of the Lumbar Spine," Clinical Orthopaedics and Related Research, 2001, No. (384), pp. 75-81.
Bostman O., et al., "Posterior Spinal Fusion Using Internal Fixation with the Daab Plate," Acta Orthopaedica Scandinavica, 1984, vol. 55 (3), pp. 310-314.
Branch C.L., et al., "Posterior Lumbar Interbody Fusion with the Keystone Graft: Technique and Results," Surgical Neurology, 1987, vol. 27 (5), pp. 449-454.
Bridwell K. H., et al., "Decision Making Regarding Smith-Petersen vs. Pedicle Subtraction Osteotomy vs. Vertebral Column Resection for Spinal Deformity," Spine, 2006, vol. 31(19S), pp. S171-S178.
Chen W.J., et al., "Surgical Treatment of Adjacent Instability After Lumbar Spine Fusion," Spine (Phila Pa 1976), 2001, vol. 26 (22), pp. E519-E524.
Chiba M., et al., "Short-Segment Pedicle Instrumentation. Biomechanical Analysis of Supplemental Hook Fixation," Spine (Phila Pa 1976), 1996, vol. 21 (3), pp. 288-294.
Cobo S.J., et al., "Predictors of Outcome After Decompressive Lumbar Surgery and Instrumented Posterolateral Fusion," European Spine Journal, 2010, vol. 19 (11), pp. 1841-1848.
Collins P., Carbon Multiwall Nanotubes: A High-Performance Conductive Additive for Demanding Plastics Applications, Materials Integrity Management Symposium, Jun. 2004, Retrieved from the Internet URL : (http://hyperioncatalysis.com/PDFs/CMWNT.pdf>).
"Curve, The Ultimate Control and Information Center" from https://www.brainlab.com/surgery-products/overview-platform-products/curve-image-guided-surgery/, 8 pages, downloaded from the Internet Mar. 27, 2014.
Dar G., et al., "The Epiphyses Ring: A Long Forgotten Anatomical Structure with Significant Physiological Function", Spine Anatomy, (PA 1976). May 15, 2011, vol. 36 (11), pp. 850-856.
Dawson E.G., et al., "Intertransverse Process Lumbararthodesis with Autogenous Bone Graft," Clinical Orthopaedics and Related Research, 1981, No. (154), pp. 90-96.

Deguchi M., et al., "Biomechanical Comparison of Spondylolysis Fixation Techniques," Spine (Phila Pa 1976), 1999, vol. 24 (4), pp. 328-333.
Denis, F., "The Three Column Spine and its Significance in the Classification of Acute Thoracolumbar Spinal Injuries," Spine (Phila Pa 1976), 1983, vol. 8 (8), pp. 817-831.
Dove J., "Internal Fixation of the Lumbar Spine. The Hartshill Rectangle," Clinical Orthopaedics and Related Research, 1986, No. (203), pp. 135-140.
Fischgrund J.S., et al., "1997 Volvo Award Winner in Clinical Studies. Degenerative Lumbar Spondylolisthesis with Spinal Stenosis: A Prospective, Randomized Study Comparing Decompressive Laminectomy and Arthrodesis with and without Spinal Instrumentation," Spine (Phila Pa 1976), 1997, vol. 22 (24), pp. 2807-2812.
"Flexural Pivot Bearings for Frictionless Applications" printout of web page as displayed from Feb. 10, 2010 accessed Sep. 16, 2019 via the Internet Wayback Machine.https://web.archive.org/web/20100210030115/http://www.flexpivots.com/.
Freeman B.J., et al., "Posterior Lumbar Interbody Fusion Combined with Instrumented Postero-Lateral Fusion: 5-year Results in 60 Patients," European Spine Journal, 2000, vol. 9 (1), pp. 42-46.
Frogley M.D., et al., "Mechanical Properties of Carbon Nanoparticle-Reinforced Elastomers," Composites Science and Technology, 2003, vol. 63 (11), pp. 1647-1654.
Gibson J.N., et al., "Surgery for Degenerative Lumbar Spondylosis," Cochrane Database of Systematic Reviews, 2005, No. (4), pp. CD001352.
Gill G.G., "Long-Term Follow-Up Evaluation of a Few Patients with Spondylolisthesis Treated by Excision of the Loose Lamina with Decompression of the Nerve Roots without Spinal Fusion," Clinical Orthopaedics and Related Research, 1984, No. (182), pp. 215-219.
Greenough C.G., et al., "Instrumented Posterolateral Lumbar Fusion. Results and Comparison with Anterior Interbody Fusion," Spine (Phila Pa 1976), 1998, vol. 23 (4), pp. 479-486.
Gunzburg R., et al., "The Conservative Surgical Treatment of Lumbar Spinal Stenosis in the Elderly," European Spine Journal, 2003, vol. 12 (Suppl. 2), pp. S176-S180.
Hajek P.D., et al., "Biomechanical Study of C1-C2 Posterior Arthrodesis Techniques," Spine (Phila Pa 1976), 1993, vol. 18 (2), pp. 173-177.
Heggeness M.H., et al., "Translaminar Facet Joint Screw Fixation for Lumbar and Lumbosacral Fusion. A Clinical and Biomechanical Study," Spine (Phila Pa 1976), 1991, vol. 16 (6 Suppl), pp. S266-S269.
Holland N.R., et al., "Intraoperative Electromyography During Thoracolumbar Spinal Surgery," Spine (Phila Pa 1976), 1998, vol. 23 (17), pp. 1915-1922.
Hoshide R., et al., "Cadaveric Analysis of the Kambin's Triangle" Cureus, Feb. 2, 2016, vol. 8 (2), pp. e475.
Katz J.N., et al., "Lumbar Laminectomy Alone or with Instrumented or Noninstrumented Arthrodesis in Degenerative Lumbar Spinal Stenosis. Patient Selection, Costs, and Surgical Outcomes," Spine (Phila Pa 1976), 1997, vol. 22 (10), pp. 1123-1131.
Kis A., et al., "Reinforcement of Single-Walled Carbon Nanotube Bundles by Intertube Bridging," Nature Materials, 2004, vol. 3 (3), pp. 153-157.
Korkala O., et al., "Reduction and Fixation of Late Diagnosed Lower Ccervical Spine Dislocations Using the Daab Plate. A Report of Two Cases," Archives of Orthopaedic and Trauma Surgery, 1984, vol. 103 (5), pp. 353-355.
Krag M.H., et al., "An Internal Fixator for Posterior Application to Short Segments of the Thoracic, Lumbar, or Lumbosacral Spine. Design and Testing," Clinical Orthopaedics and Related Research, 1986, No. (203), pp. 75-98.
Lin P.M., et al., "Internal Decompression for Multiple Levels of Lumbar Spinal Stenosis: A Technical Note," Neurosurgery, 1982, vol. 11 (4), pp. 546-549.
Liquidmetal Technologies product page from http://liquidmetal.com/our-products/product-parts/, What we Sell, 5 pages, downloaded from the internet Mar. 27, 2014.
Lorenz M., et al., "A Comparison of Single-Level Fusions with and without Hardware," Spine (Phila Pa 1976), 1991, vol. 16 (8 Suppl), pp. S455-S458.

(56) References Cited

OTHER PUBLICATIONS

Lowery G.L., "Orion Anterior Cervical Plate System" in: Spinal Instrumentation—Surgical Techniques, Kim D.H., et al., eds., Thieme Medical Publications (New York), 2005, pp. 116-122.

Luque E.R., "Segmental Spinal Instrumentation of the Lumbar Spine," Clinical Orthopaedics and Related Research, 1986, No. (203), pp. 126-134.

Madan S., et al., "Outcome of Posterior Lumbar Interbody Fusion Versus Posterolateral Fusion for Spondylolytic Spondylolisthesis," Spine (Phila Pa 1976), 2002, vol. 27 (14), pp. 1536-1542.

Madan S.S., et al., "Circumferential and Posterolateral Fusion for Lumbar Disc Disease," Clinical Orthopaedics and Related Research, 2003, No. (409), pp. 114-123.

Marotta N., et al., "A Novel Minimally Invasive Presacral Approach and Instrumentation Technique for Anterior L5-S1 Intervertebral Discectomy and Fusion: Technical Description and Case Presentations," Neurosurgical Focus, 2006, vol. 20 (1), pp. E9.

McInerney J., et al., "Frameless Stereotaxy of the Brain," The Mount Sinai Journal of Medicine, 2000, vol. 67 (4), pp. 300-310.

Moskowitz A., "Transforaminal Lumbar Interbody Fusion," Orthopedic Clinics of North America, 2002, vol. 33 (2), pp. 359-366.

Nardi P., et al., "Aperius PercLID Stand Alone Interspinous System for the Treatment of Degenerative Lumbar Stenosis: Experience on 152 Cases," Journal of Spinal Disorders & Techniques, 2010, vol. 23 (3), pp. 203-207.

Neo M., et al., "Spinous Process Plate Fixation as a Salvage Operation for Failed Anterior Cervical Fusion. Technical Note," Journal of Neurosurgery: Spine, 2006, vol. 4 (1), pp. 78-81.

Netter F., Atlas of Human Anatomy, 3rd Edition, Icon Learning Systems, Tegerboro, New Jersey (2004).

O'Leary P.F., et al., "Distraction Laminoplasty for Decompression of Lumbar Spinal Stenosis," Clinical Orthopaedics and Related Research, 2001, No. (384), pp. 26-34.

Ozgur B.M., et al., "Extreme Lateral Interbody Fusion (XLIF): A Novel Surgical Technique for Anterior Lumbar Interbody Fusion," Spine Journal, 2006, vol. 6 (4), pp. 435-443.

Polly D.W., et al., "Surgical Treatment for the Painful Motion Segment: Matching Technology with the Indications: Posterior Lumbar Fusion," Spine (Phila Pa 1976), 2005, vol. 30 (16 Suppl), pp. S44-S51.

Qian D., et al., "Mechanics of Carbon Nanotubes," Applied Mechanics Reviews, 2002, vol. 55 (2), pp. 495-533.

Rapoff A.J., et al., "Biomechanical Comparison of Posterior Lumbar Interbody Fusion Cages," Spine (Phila Pa 1976), 1997, vol. 22 (20), pp. 2375-2379.

Rompe J.D., et al., "Degenerative Lumbar Spinal Stenosis. Long-Term Results After Undercutting Decompression Compared with Decompressive Laminectomy Alone or with Instrumented Fusion," Neurosurgical Review, 1999, vol. 22 (2-3), pp. 102-106.

Rousseau M.A., et al., "Predictors of Outcomes After Posterior Decompression and Fusion in Degenerative Spondylolisthesis," European Spine Journal, 2005, vol. 14 (1), pp. 55-60.

Santoni BG., et al., "Cortical Bone Trajectory for Lumbar Pedicle Screws" The Spine Journal, 2009, vol. 9 (5), pp. 366-373.

Sasso R.C., et al., "Translaminar Facet Screw Fixation," World Spine Journal, 2006, vol. 1 (1), pp. 34-39.

Sidhu K.S., et al., "Spinal Instrumentation in the Management of Degenerative Disorders of the Lumbar Spine," Clinical Orthopaedics and Related Research, 1997, No. (335), pp. 39-53.

Smith M.D., et al., "A Biomechanical Analysis of Atlantoaxial Stabilization Methods Using a Bovine Model. C1/C2 Fixation Analysis," Clinical Orthopaedics and Related Research, 1993, No. (290), pp. 285-295.

Stambough J.L., et al., "Instrumented One and Two Level Posterolateral Fusions with Recombinant Human Bone Morphogenetic Protein-2 and Allograft: A Computed Tomography Study," Spine (Phila Pa 1976), 2010, vol. 35 (1), pp. 124-129.

Stambough J.L., "Lumbosacral Instrumented Fusion: Analysis of 124 Consecutive Cases," Journal of Spinal Disorders, 1999, vol. 12 (1), pp. 1-9.

Suzuki Y., "Shape Memory and Super-Elasticity Effects in NiTi Alloys," Titanium-Zirconium, 1982, vol. 30 (4), pp. 185-192.

Swanson K.E., et al., "The Effects of an Interspinous Implant on Intervertebral Disc Pressures," Spine (Phila Pa 1976), 2003, vol. 28 (1), pp. 26-32.

Thomsen K., et al., "1997 Volvo Award Winner in Clinical Studies. The Effect of Pedicle Screw Instrumentation on Functional Outcome and Fusion Rates in Posterolateral Lumbar Spinal Fusion: A Prospective, Randomized Clinical Study," Spine (Phila Pa 1976), 1997, vol. 22 (24), pp. 2813-2822.

Tseng Y.C., et al., "Monolithic Integration of Carbon Nanotube Devices with Silicon MOS Technology," Nano Letters, 2004, vol. 4 (1), pp. 123-127.

Vaccaro, et al., Principles of Practice of Spine Surgery; Mosby Press, Philadelphia, PA; 2003.

Vamvanij V., et al., "Surgical Treatment of Internal Disc Disruption: An Outcome Study of Four Fusion Techniques," Journal of Spinal Disorders, 1998, vol. 11 (5), pp. 375-382.

Voor M.J., et al., "Biomechanical Evaluation of Posterior and Anterior Lumbar Interbody Fusion Techniques," Journal of Spinal Disorders, 1998, vol. 11 (4), pp. 328-334.

Wang J.C., et al., "Comparison of CD HORIZON SPIRE Spinous Process Plate Stabilization and Pedicle Screw Fixation after Anterior Lumbar Interbody Fusion. Invited Submission from the Joint Section Meeting on Disorders of the Spine and Peripheral Nerves, Mar. 2005," Journal of Neurosurgery: Spine, 2006, vol. 4 (2), pp. 132-136.

Wang J.C., et al., "SPIRE Spinous Process Stabilization Plate: Biomechanical Evaluation of a Novel Technology. Invited Submission from the Joint Section Meeting on Disorders of the Spine and Peripheral Nerves, Mar. 2005," Journal of Neurosurgery: Spine, 2006, vol. 4 (2), pp. 160-164.

Webster T.J., et al., "Increased Osteoblast Adhesion on Nanophase Metals: Ti, Ti6Al4V, and CoCrMo," Biomaterials, 2004, vol. 25 (19), pp. 4731-4739.

Willard, F. H., et al., "The Thoracolumbar Fascia: Anatomy, Function and Clinical Considerations." Journal of Anatomy, 2012, vol. 221(6), pp. 507-536.

Wohns R.N.W., et al., Day Surgery for Anterior Cervical Microdiskectomy: Experience with 75 Cases, Jul. 11, 2002, pp. 1-3.

Wood M.J., et al., "Improving Accuracy and Reducing Radiation Exposure in Minimally Invasive Lumbar Interbody Fusion," Journal of Neurosurgery: Spine, 2010, vol. 12 (5), pp. 533-539.

Yang C.K., et al., "Binding energies and electronic Structures of Adsorbed Titanium Chains on Carbon Nanotubes," Physical Review 66, 2002, 041403-1.

Yerby S., et al., "The Effect of Cutting Flute Design on the Insertion and Pullout Properties of Self-tapping Bone Screws," Jul. 2, 2002, pp. 1-2.

\* cited by examiner

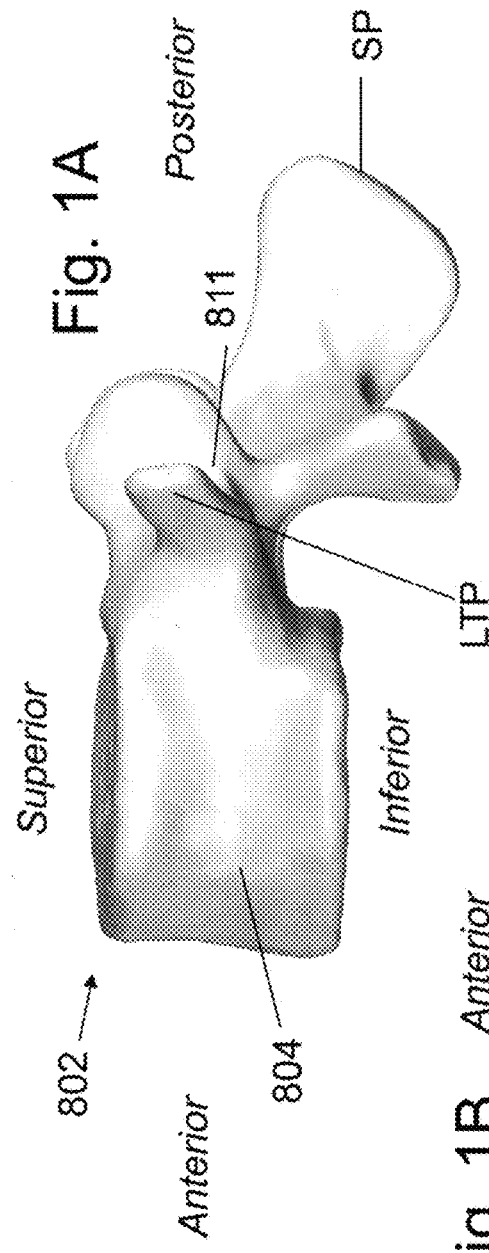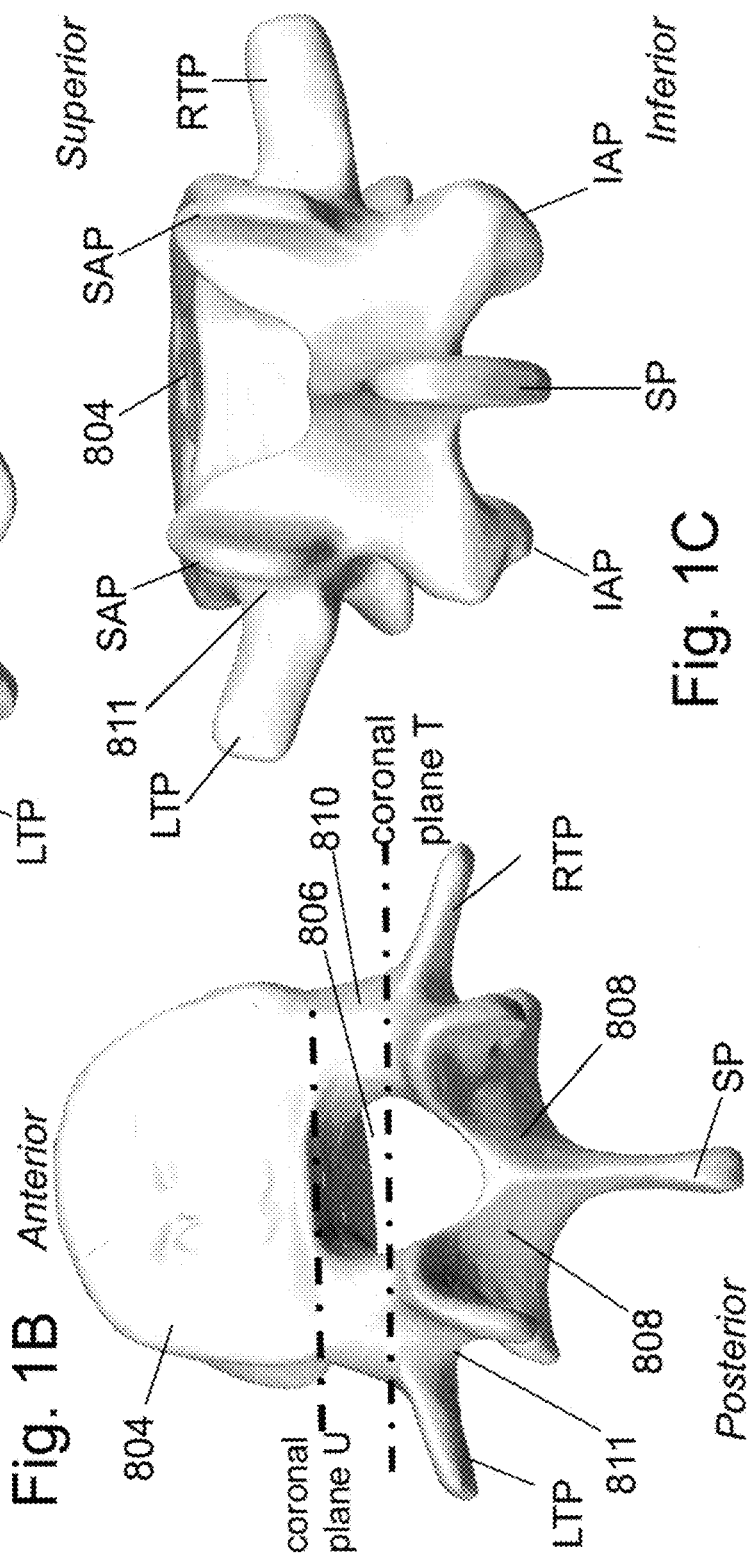

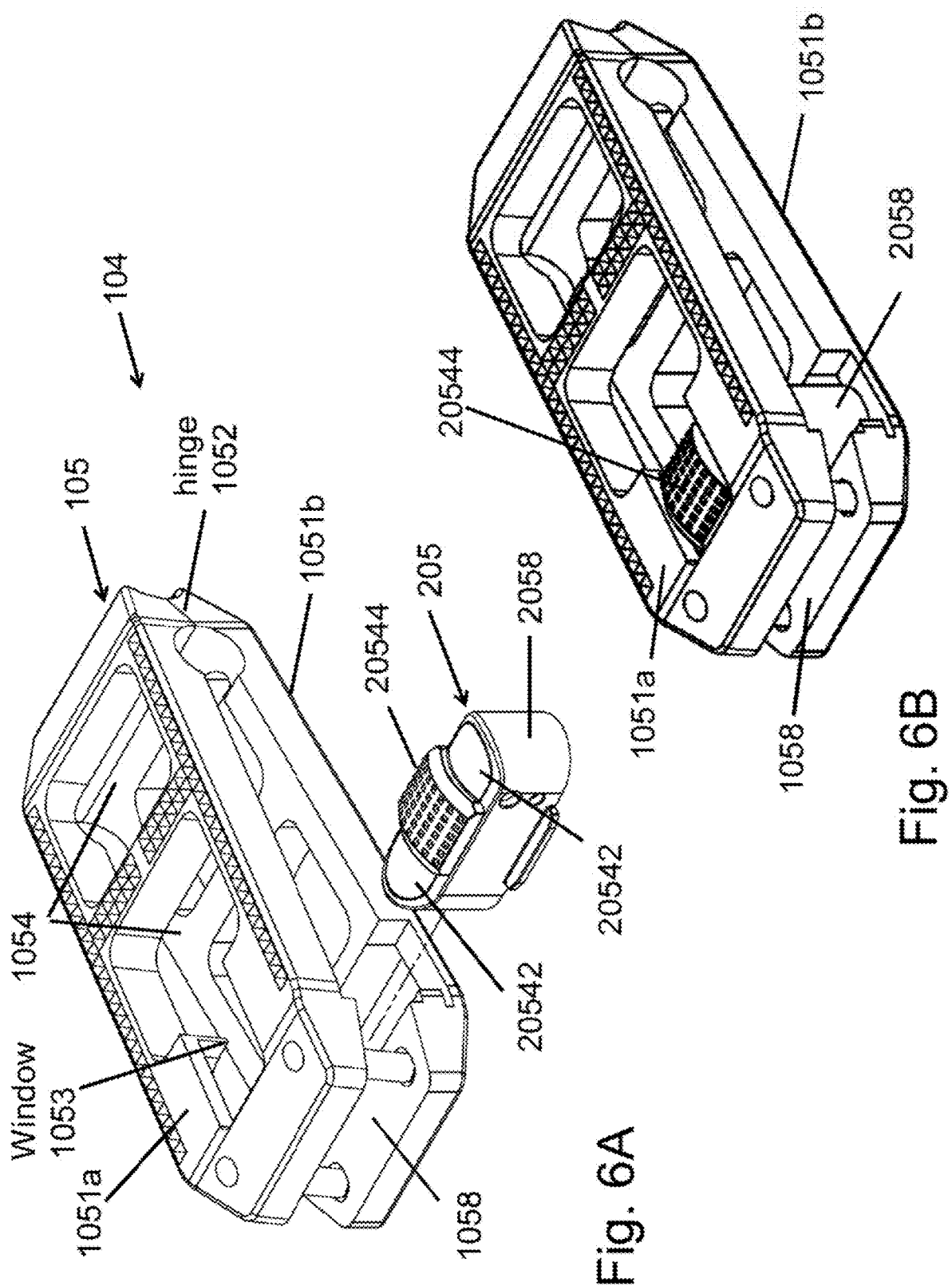

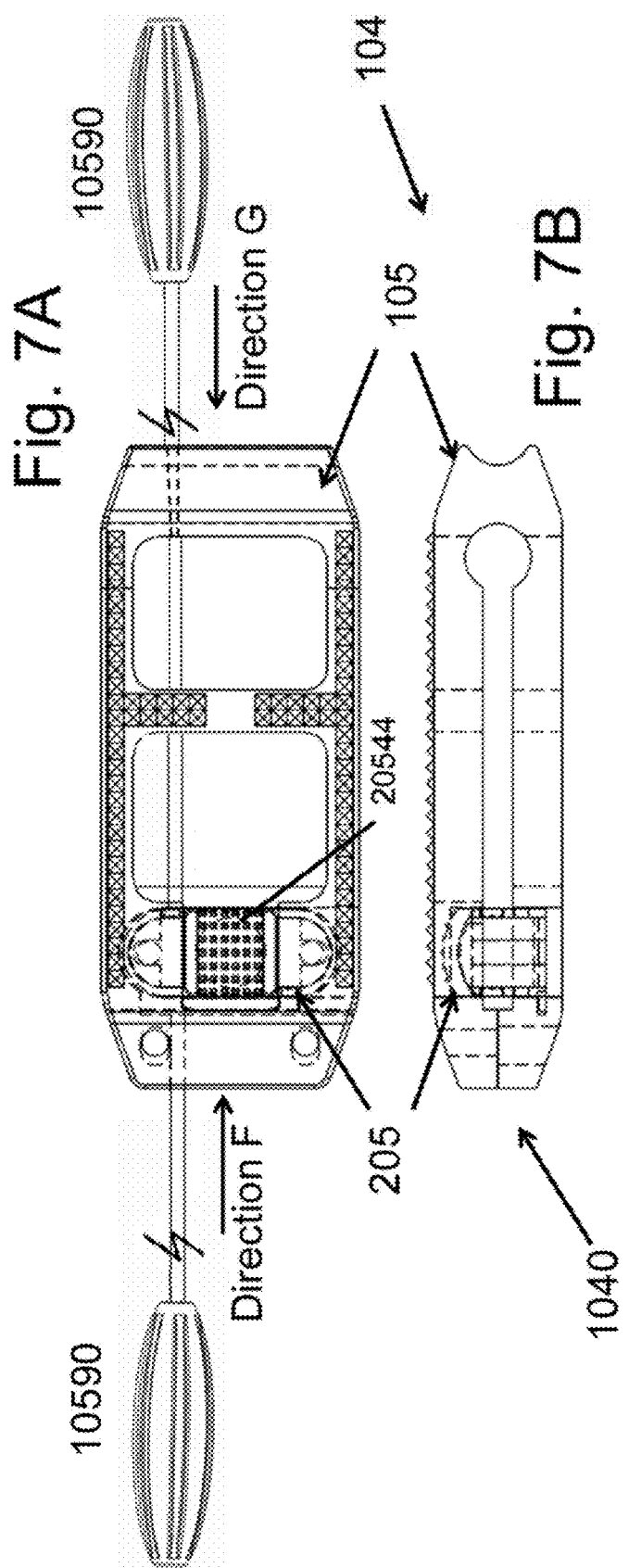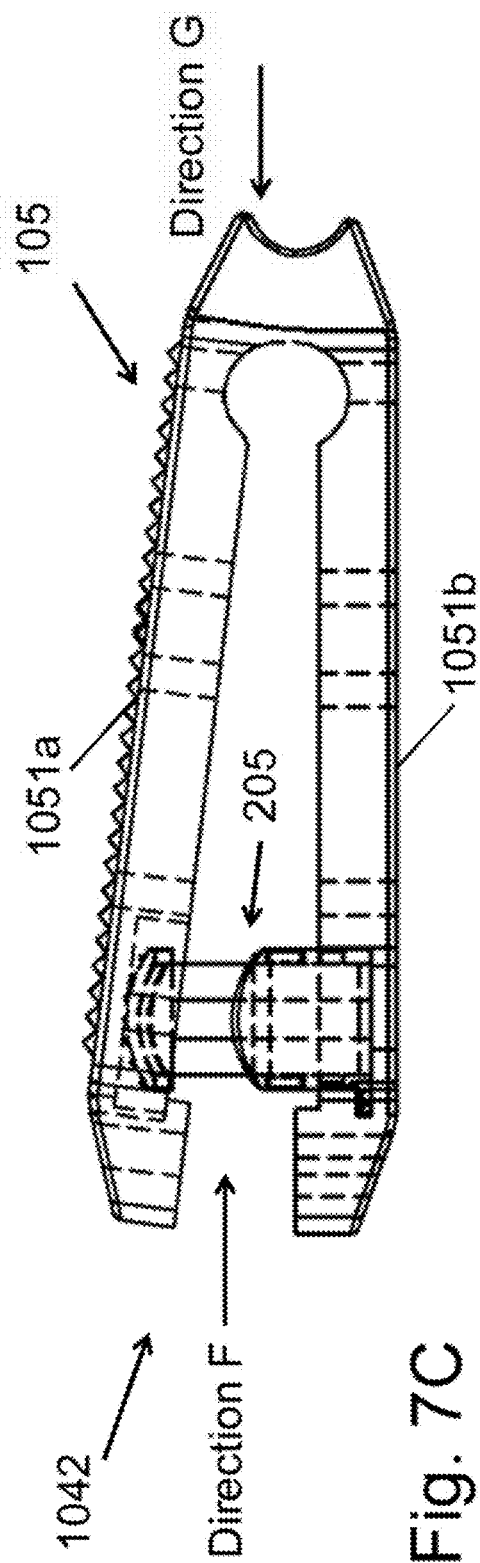

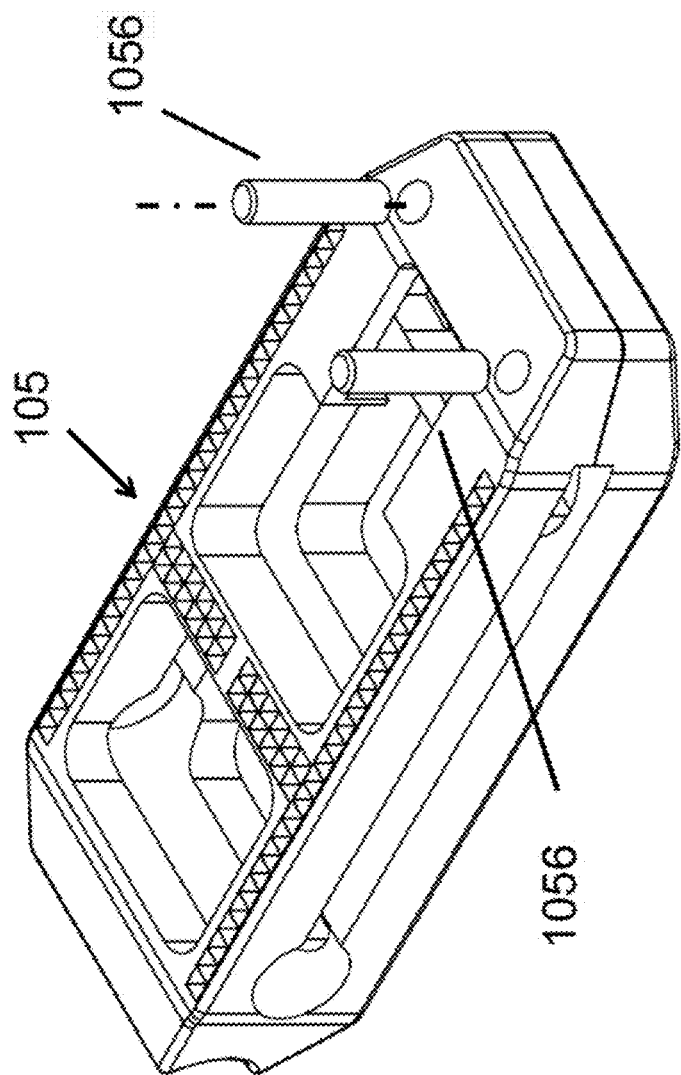
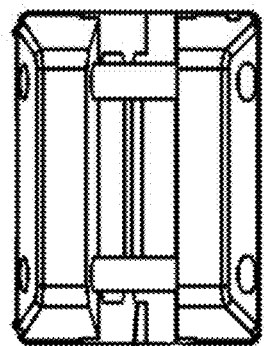
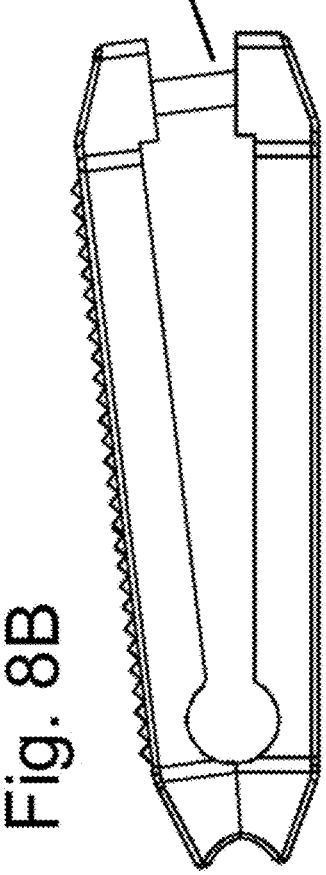

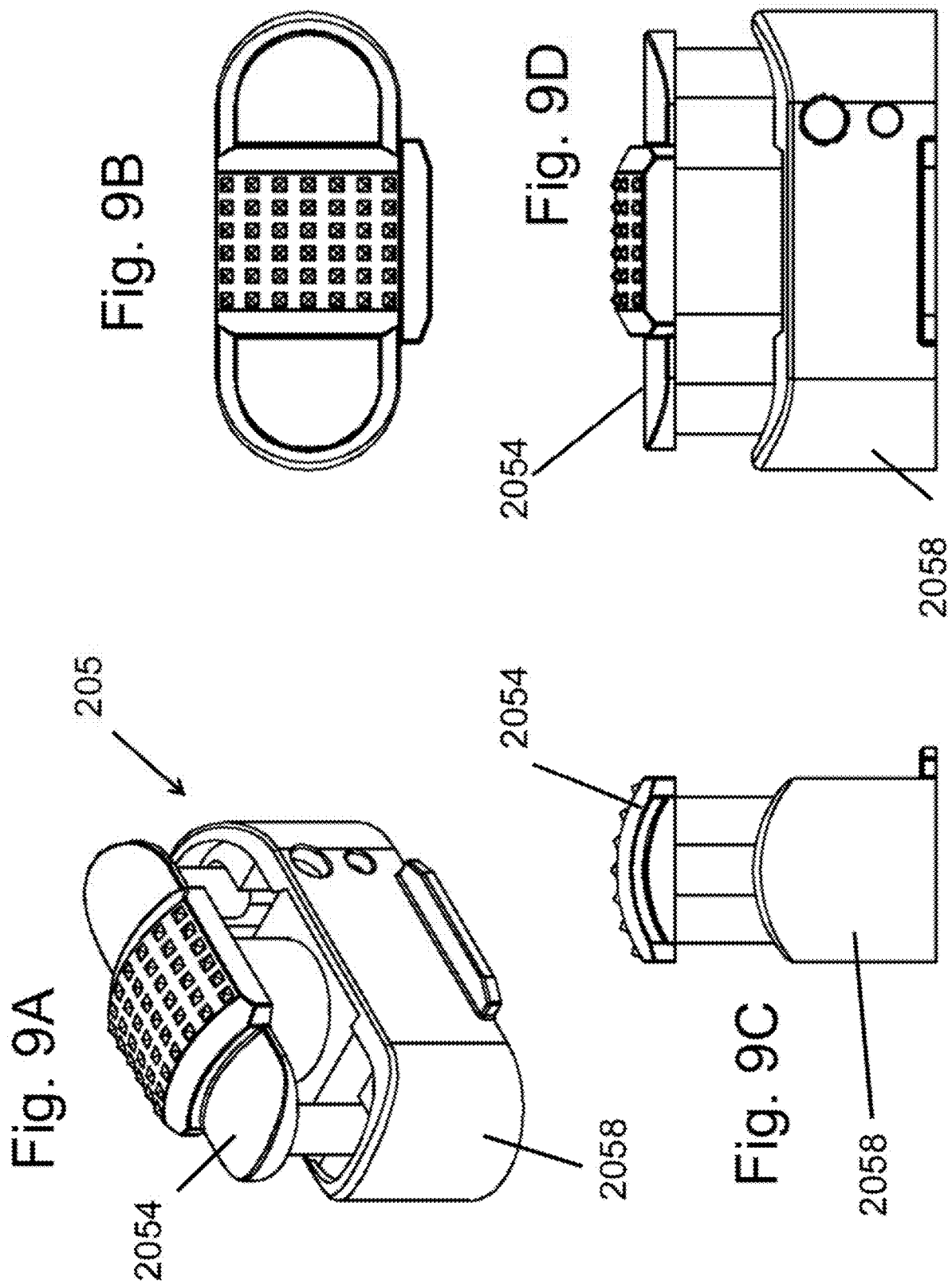

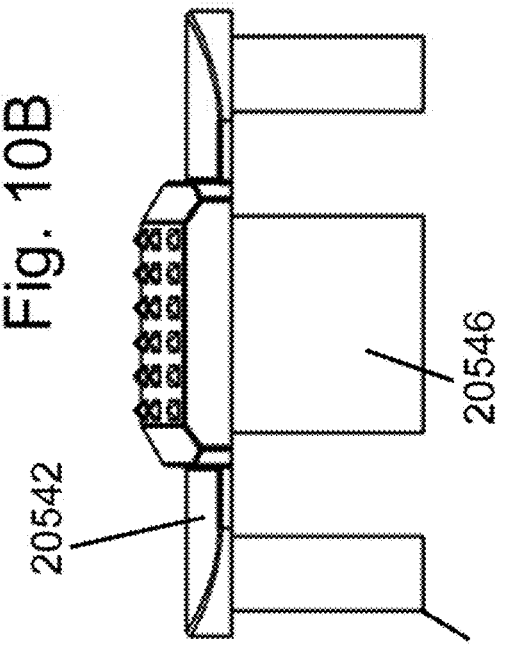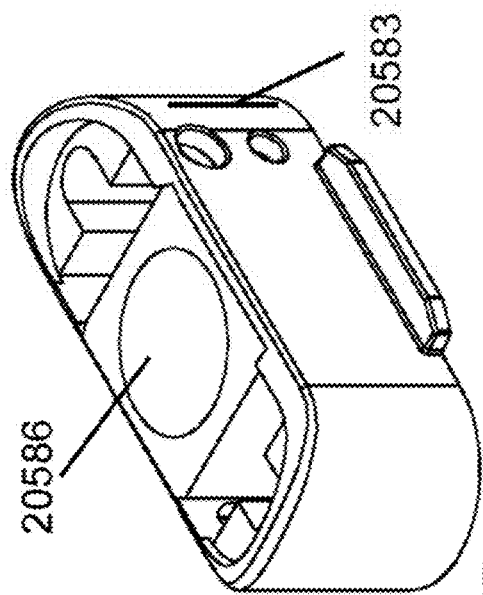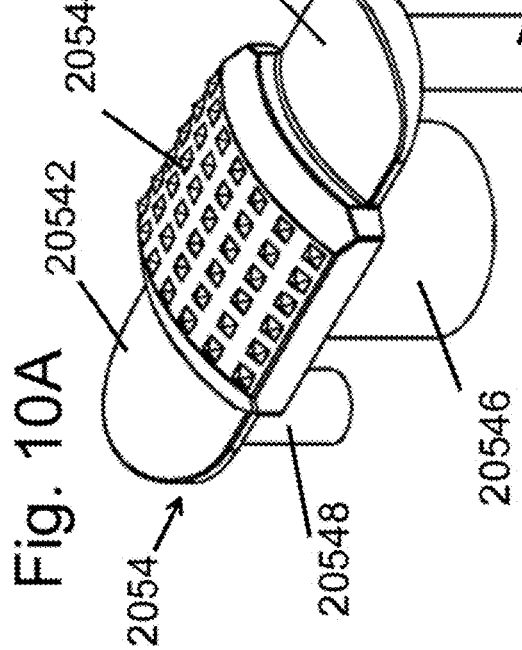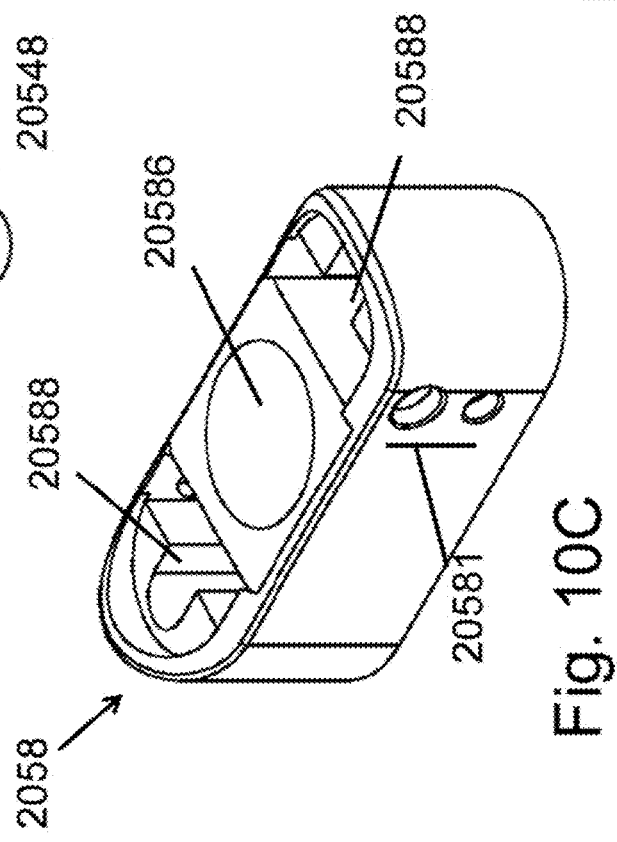

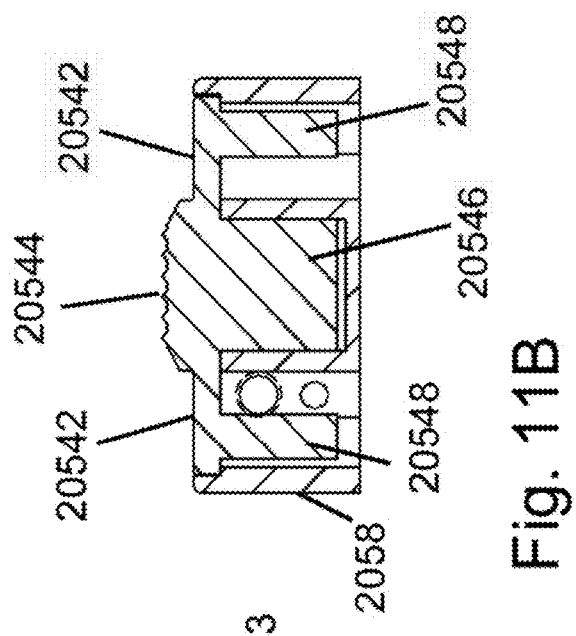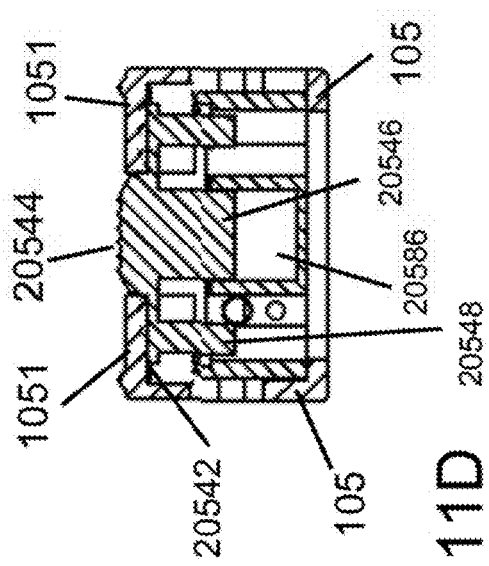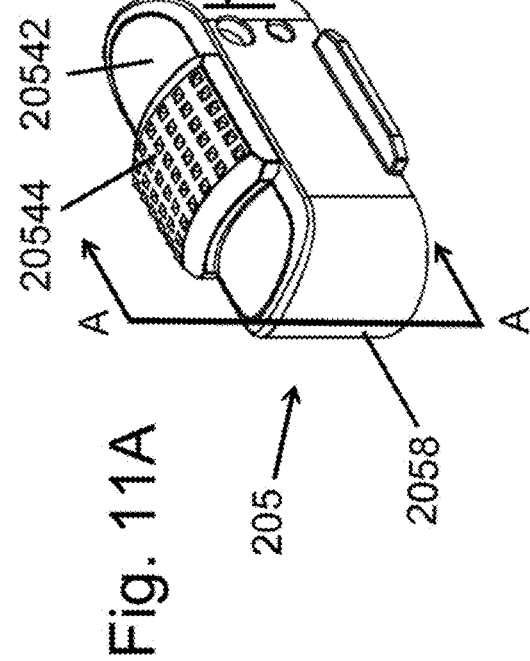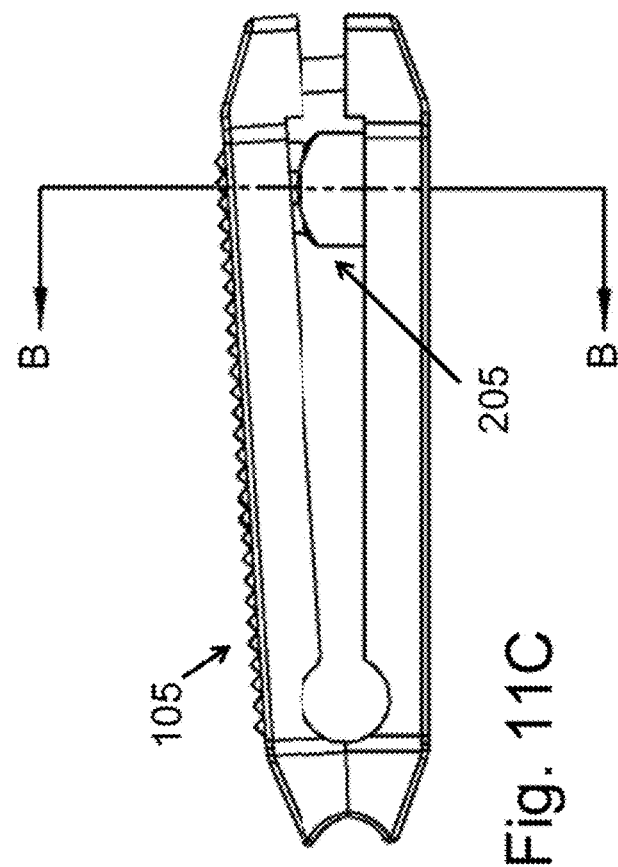

Before implantation

After implantation

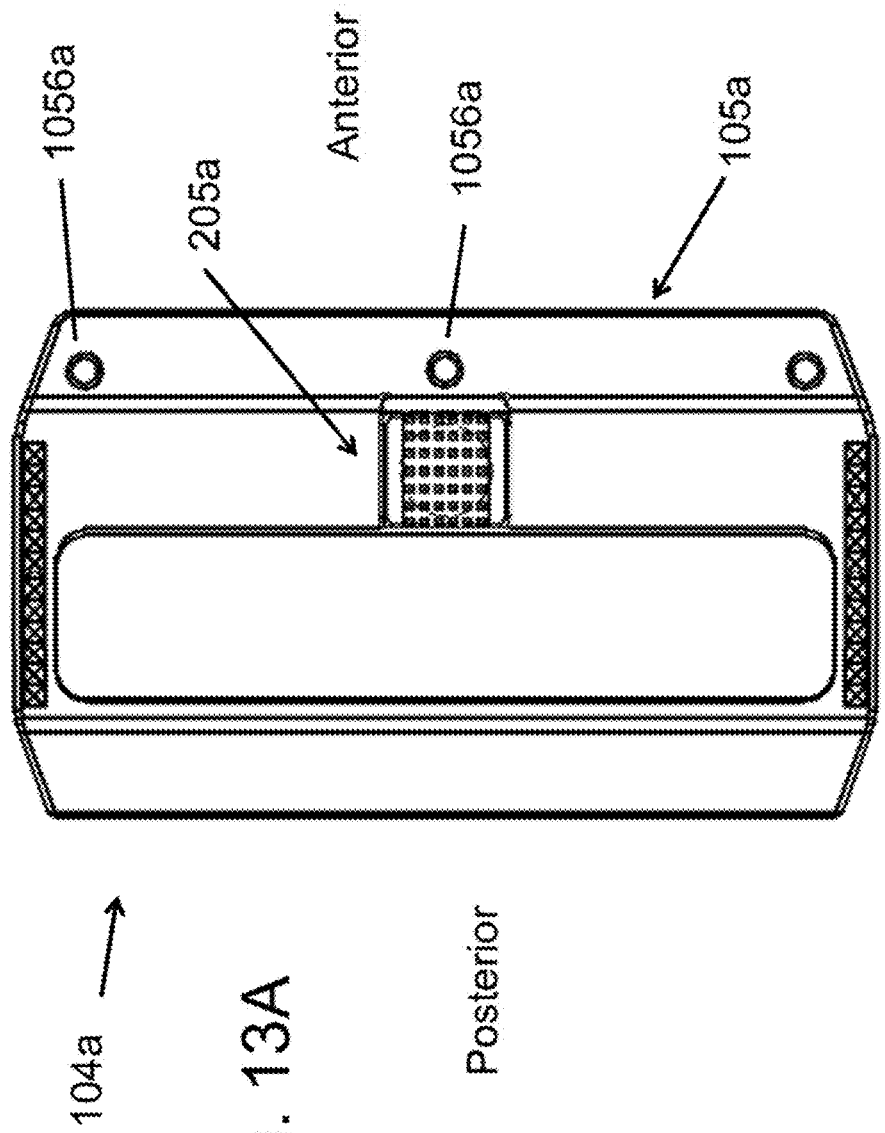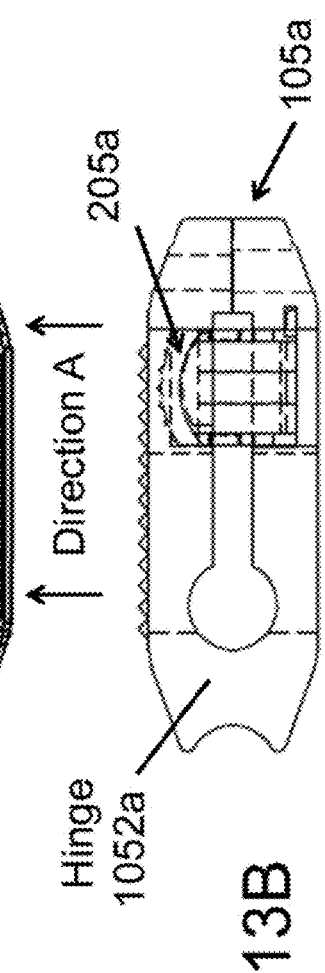
Fig. 13A
Fig. 13B

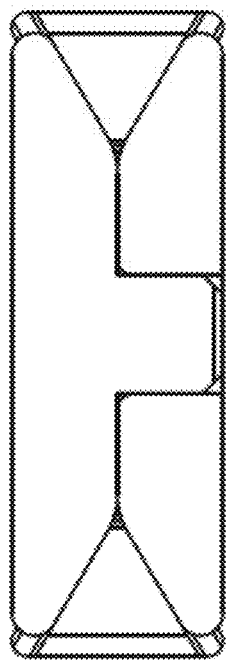
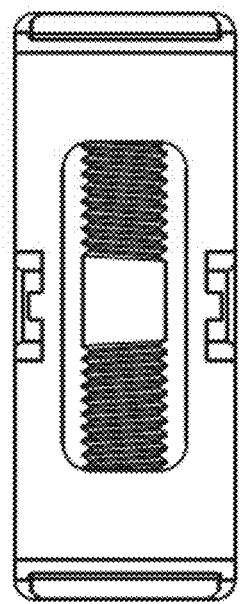
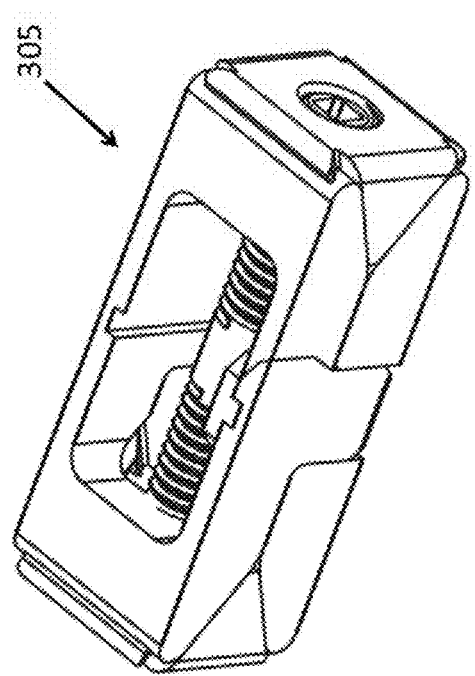
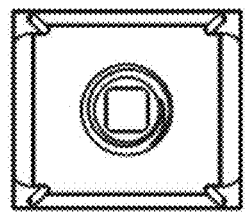
FIG. 19

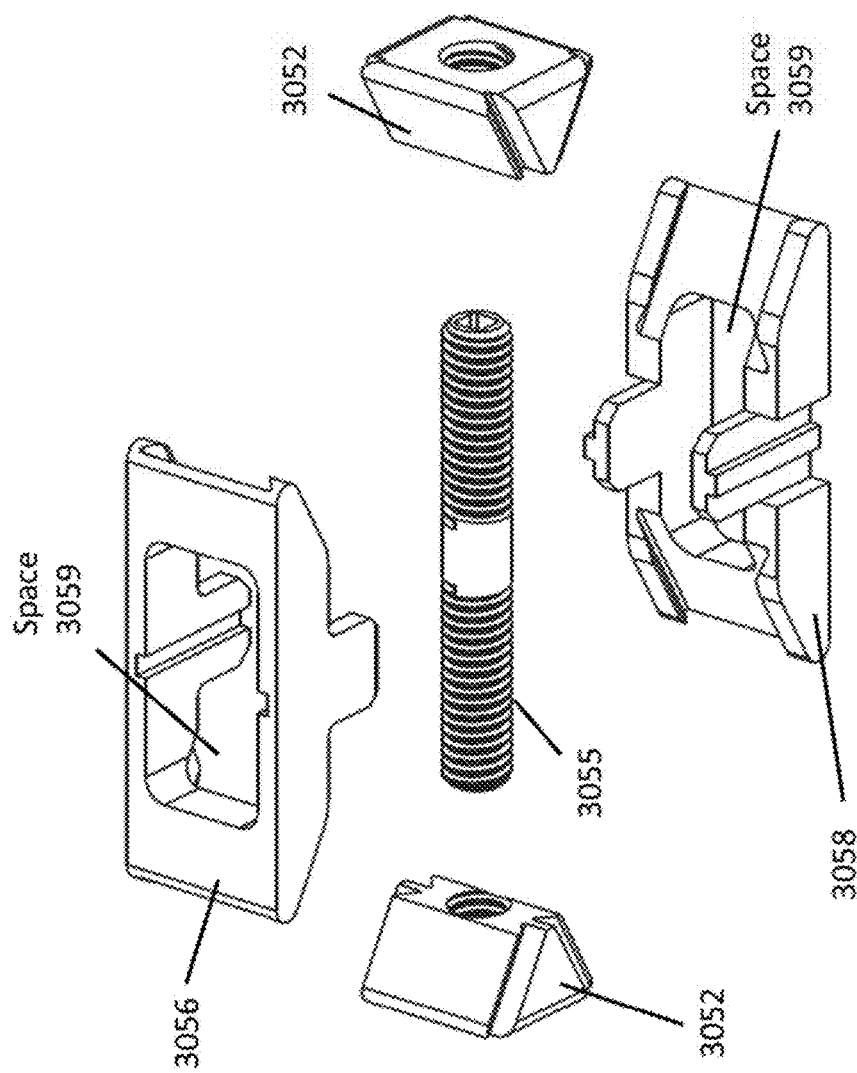

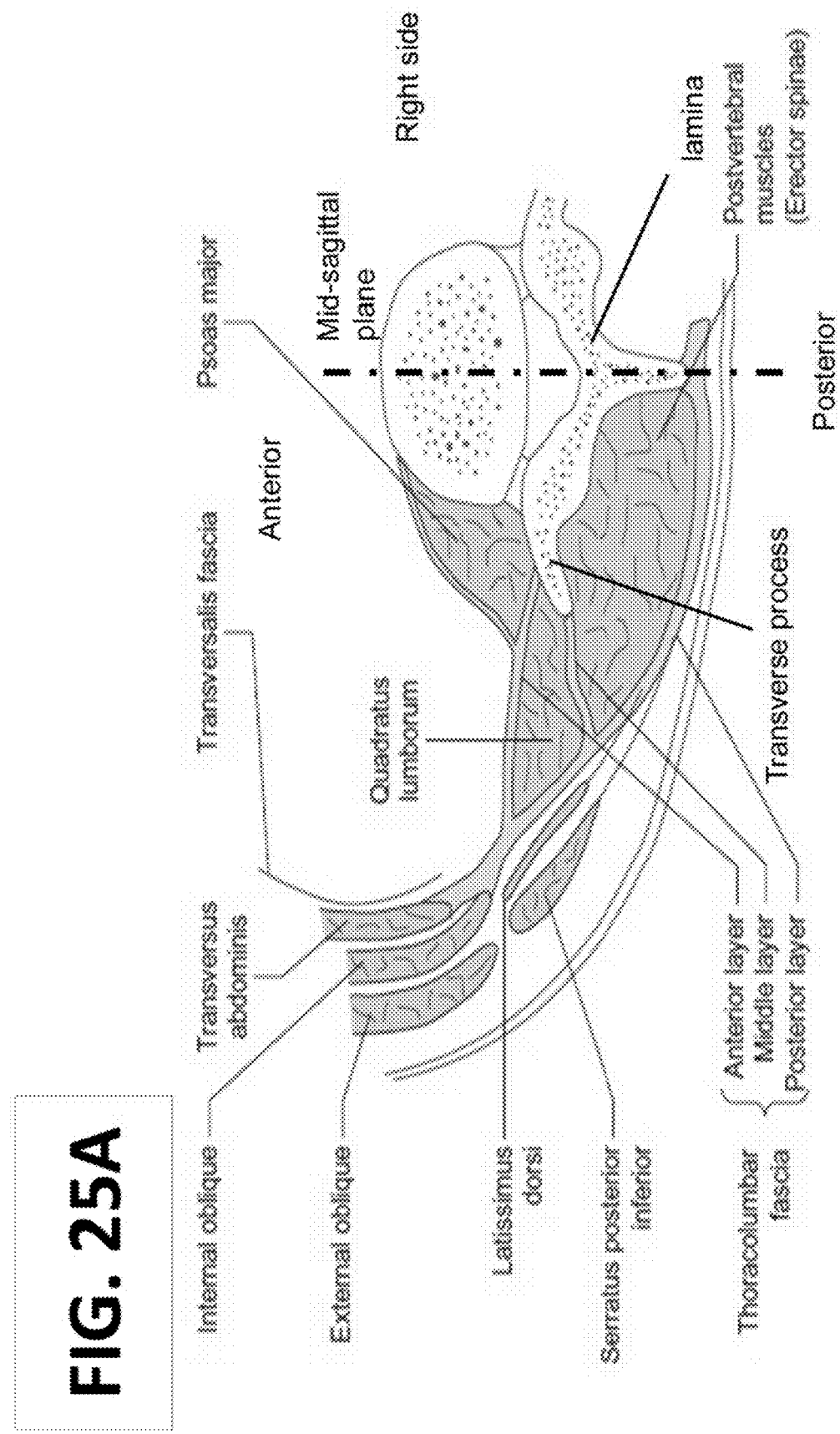

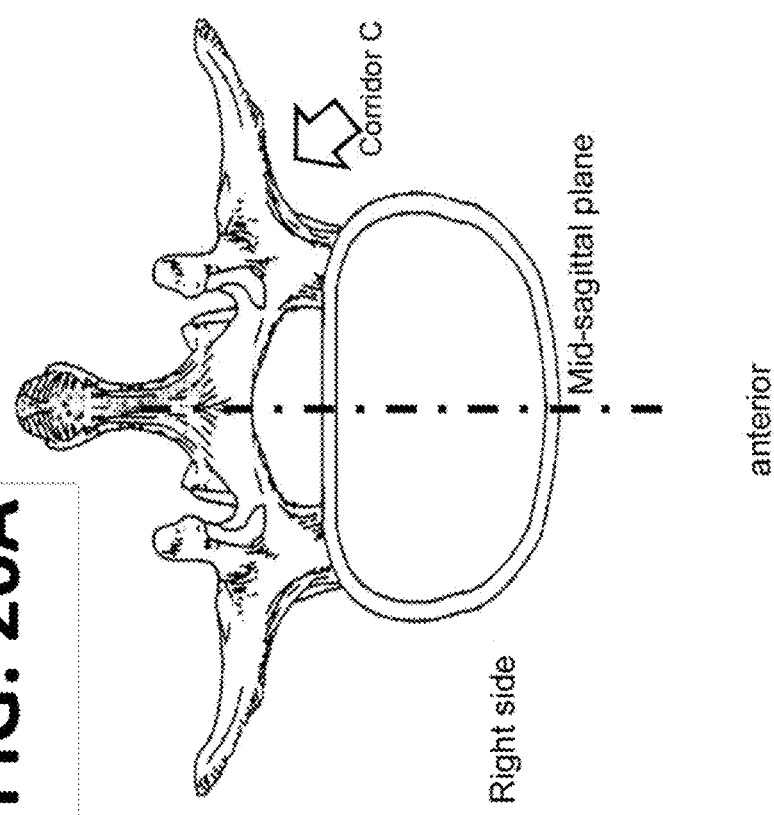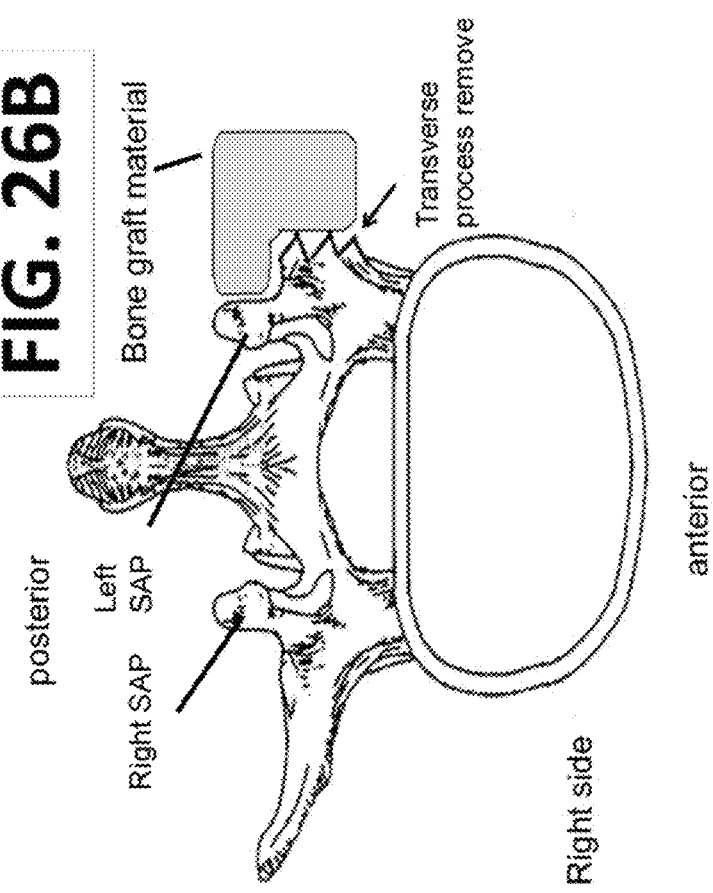

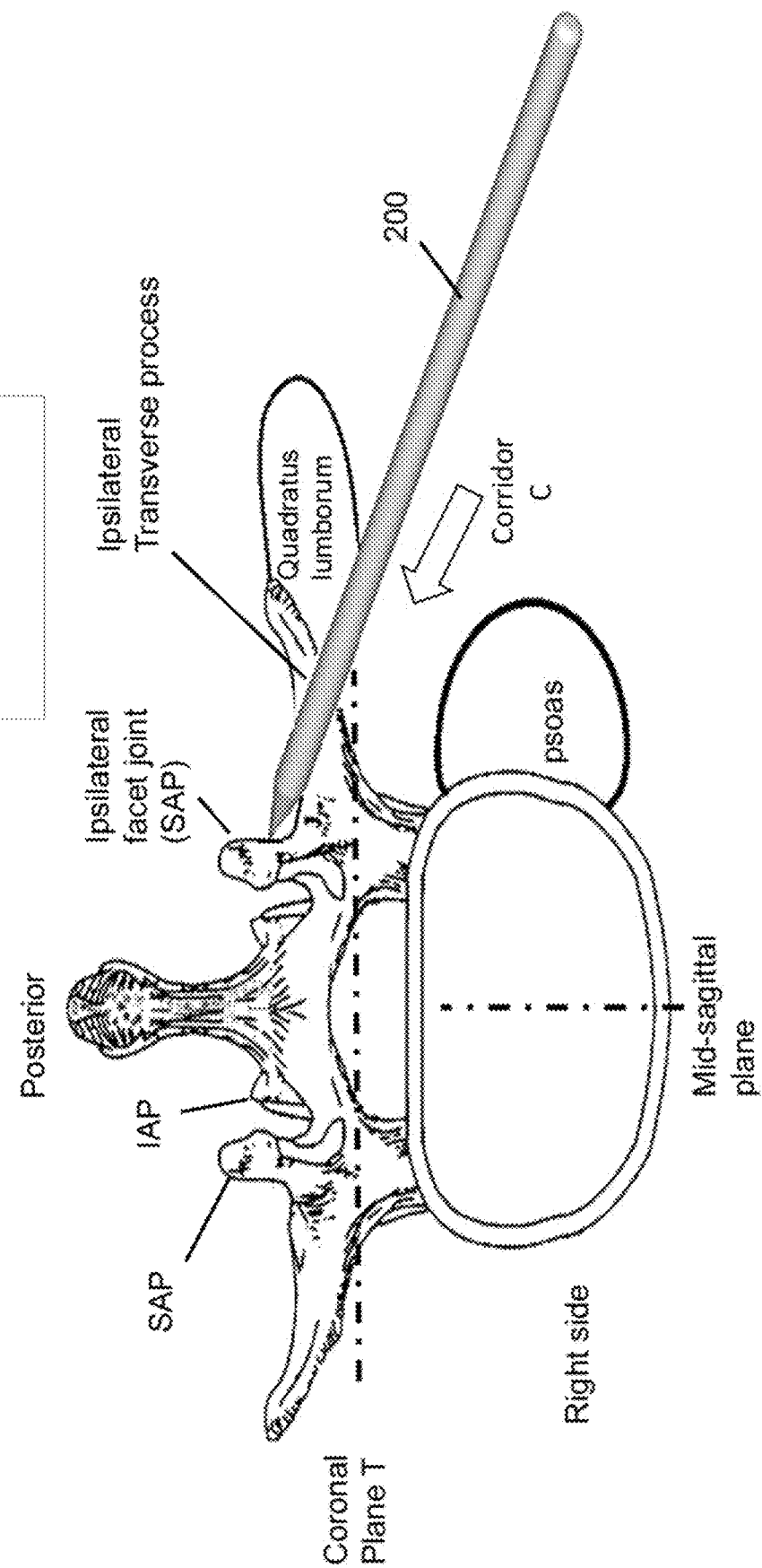

DEVICES AND METHODS FOR VERTEBRAL BONE REALIGNMENT

PRIORITY

This application is a continuation-in-part of and claims priority to co-owned U.S. patent application Ser. No. 15/793,895 filed on Oct. 25, 2017 of the same title, which claims priority to U.S. Provisional Patent Application Ser. No. 62/496,721 entitled "DEVICES AND METHODS FOR VERTEBRAL BONE RE-ALIGNMENT", filed Oct. 25, 2016, each of which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

This disclosure relates generally to medical devices, and in one exemplary aspect to bone fixation systems, components thereof, and methods of implant placement, which can be used to, inter alia, adjust, align and maintain the spatial relationship(s) of adjacent bones or bony fragments during and/or after surgical reconstruction of skeletal segments. While illustrated for use in the vertebral column, it is understood that the disclosed implants and methods may be used in any application skeletal segment.

2. Description of Related Technology

Whether from congenital malformation, degenerative disease, traumatic disruption, infection or neoplastic invasion, alteration in the anatomical alignment between the spinal vertebrae can cause significant pain, deformity, neurological decline and disability. Spinal disease is a major health problem in the industrialized world and the surgical treatment of spinal pathology is an evolving discipline. The traditional surgical treatment of abnormal vertebral motion and/or formation is the complete immobilization and bony fusion of the involved spinal segment and an extensive array of surgical techniques and implantable devices have been formulated to accomplish the treatment objective.

Regardless of the specific objectives of surgery, many surgeons employ implantable devices that maintain the desired spatial relationship(s) between adjacent vertebral bodies. However, conventional implantable devices are limited in that they are, inter alia, primarily "one size fits all," including standardized configurations and sizes which are non-adjustable and/or not particularly adapted for certain applications. Thus, such conventional implants may be insufficient for treatment of patients with unusual or complex spinal curvatures and maladies, which may occur in conditions such as e.g., coronal plane deformity (such as scoliosis), sagittal plane deformity (such as alternation in segmental kyphosis or lordosis), axial translation, spondylolisthesis, etc.

Hence there is a salient need for alternative methods and devices for the alteration and/or correction of spinal curvature, which, inter alia, enable variable and/or adjustable configurations for implantable devices, such as to realign adjacent vertebrae according to the spinal structure or curvature of a specific subject.

SUMMARY

Improved devices, systems, and methods to alter vertebral alignment are described herein.

In one aspect, an implantable device is disclosed. In one embodiment, the device comprises a distraction mechanism, and a first member or a host member configured to at least partly retain the distraction mechanism.

In one variant, the host member comprises a set of substantially planar elements configured to articulate relative to one another around at least one axis, so as to permit insertion and/or removal of the distraction mechanism. The distraction mechanism can cause the implantable device to change a height of one side so as to allow for intervertebral correction of e.g., scoliosis.

In another variant, the host member is configured to enable adjustment of height of both sides of the implant.

In another aspect, a method of inserting an implantable device within an intervertebral space is disclosed. In one embodiment, the method includes inserting an assembled implant device in the disc space, and adjusting a height of at least a portion thereof so as to compensate for asymmetries in the disc space caused by, e.g., scoliosis.

In another aspect, a method of treating a spinal misalignment is disclosed. In one embodiment, the method includes utilizing an implant assembly to alter the spinal alignment of a target functional spinal unit in the coronal plane in order to treat coronal plane deformities such as, e.g., scoliosis.

In another embodiment, the method includes utilizing an implant assembly to alter the spinal alignment of a target functional spinal unit in the sagittal plane in order to treat sagittal plane deformities such as, e.g., abnormal lordosis and/or kyphosis.

In yet another embodiment, the method comprises utilizing an implant assembly to alter the spinal alignment of the target functional spinal unit in the axial plane in order to, for example, treat translational deformities such as e.g., anterior/posterior or lateral spondylolisthesis.

In another aspect, a distraction mechanism for use within an implantable device is disclosed. In one embodiment, the distraction mechanism includes a piston which utilizes a working fluid to drive the piston (and hence a top portion of the mechanism) into compressive contact with an inferior surface of a superior vertebral segment. In another embodiment, the mechanism uses a mechanical (non-fluidic) arrangement for the compression (e.g., worm drive, gear mechanism, etc.).

In a further aspect, a system for correction of spinal conditions is disclosed. In one embodiment, the system includes: (i) a host housing member, (ii) a distraction mechanism, and (iii) a tool for adjusting the distracting mechanism after implantation.

In a further aspect of the present disclosure, a modular device assembly is disclosed. In one embodiment, the modular device assembly is configured to be at least partially seated within an intervertebral disc space, the intervertebral disc space disposed between a superior vertebral bone and an adjacent inferior vertebral bone. In one variant, the modular device assembly includes: a receiving member including: a first top surface; and a first opposing bottom surface movably coupled with the first top surface, the first top surface and the first opposing bottom surface of the receiving member cooperatively configured to reversibly receive a distraction module therebetween, the distraction module including: a second top surface; a second opposing bottom surface configured to be movable relative to the second top surface; and an actuator.

In one implantation, the distraction module is configured to cause upon actuation: displacement of the second top surface of the distraction module away from the second opposing bottom surface of the distraction module; and an increase of a distance between at least a portion of the first top surface and at least a portion of the first opposing bottom surface of the receiving member.

In another implementation, the distraction module is further configured to be received by the receiving member as a unitary assembly.

In another aspect of the present disclosure, another modular device assembly is disclosed. In one embodiment, the modular device assembly is configured for implantation within an intervertebral disc space, the intervertebral disc space disposed between a superior vertebral bone and an adjacent inferior vertebral bone, and the modular device assembly includes: a housing member including: a first top surface; and a first bottom surface; and a unitary distraction module including: a second top surface; a second bottom surface; and a distraction mechanism.

In one variant, the modular device assembly further includes an axis extending from the first top surface to the first bottom surface and through at least a portion of the distraction mechanism of the distraction module.

In another variant, the distraction mechanism is configured to, upon actuation, be devoid of rotational movement centered about the axis.

In another aspect of the present disclosure, another modular device assembly is disclosed. In one embodiment, the modular device assembly is configured for implantation within an intervertebral disc space, the intervertebral disc space disposed between a superior vertebral bone and an adjacent inferior vertebral bone, and the modular device assembly includes: a housing member including: a first surface; a second surface; and a coupler configured to reversibly receive at least one unitary distraction module; and the at least one unitary distraction module, the at least one unitary distraction module including: a third surface; a fourth surface; and a distraction mechanism.

In one variant, the distraction mechanism is configured to be devoid of gear engagement along an axis extending from the first surface to the second surface and at least partly through the distraction mechanism of the distraction module.

In another aspect of the present disclosure, a method for the treatment of a functional spinal unit of a subject is disclosed. In one embodiment, the functional spinal unit extends along a longitudinal axis of the subject and comprising a superior vertebral bone, an inferior vertebral bone and an intervertebral disc space positioned at least partly between the superior vertebral bone and the inferior vertebral bone, and the method includes: approaching at least one side surface of the intervertebral disc space; selecting a component of a modular implant assembly based on an assessment of a dimension of the intervertebral disc space, the selected components including: a receiving member, the receiving member including (i) a first top surface, (ii) a first opposing bottom surface, (iii) a first side surface comprising a malleable member configured to movably couple the first top surface and the first opposing bottom surface, and (iv) a first cavity configured to at least partially seat a distraction module; advancing the receiving member into the intervertebral disc space; advancing the distraction module into the first cavity of the receiving member; and positioning a bone forming material at least partially within the receiving member.

BRIEF DESCRIPTION OF THE DRAWINGS

FIGS. 1A-1C show diagrammatic representations of a spinal vertebral bone in multiple views.

FIGS. 6A and 6B illustrate one embodiment of an implantable device according to the present disclosure.

FIG. 7A shows top and side plan views of the device of FIGS. 6A and 6B, with distraction mechanism inserted.

FIG. 7B shows a side plan view of the device of FIGS. 6A and 6B, in a closed position.

FIG. 7C shows a side plan view of the device of FIGS. 6A and 6B, in an open position, with distraction mechanism installed.

FIG. 8A shows a top perspective view of the device of FIGS. 6A and 6B.

FIG. 8B shows a side elevation view of the device of FIG. 8A.

FIG. 8C shows a front elevation view of the device of FIG. 8A.

FIG. 9A shows a top perspective view of one embodiment of the distraction mechanism of FIGS. 6A and 6B.

FIG. 9B shows a top view of the distraction mechanism of FIG. 9A.

FIG. 9C shows a front view of the distraction mechanism of FIG. 9A.

FIG. 9D shows a side view of the distraction mechanism of FIG. 9A.

FIGS. 10A, 10B, 10C, and 10D show top, top perspective, and side views of various constituent members of the distraction mechanism of FIG. 9.

FIG. 11A shows a top perspective view of the exemplary distraction mechanism of FIG. 9.

FIG. 11B shows a front cross-sectional view (taken along line B-B) of the exemplary distraction mechanism of FIG. 9, shown positioned within a host member of the implant device.

FIG. 11C shows a side plan view of the device of FIGS. 6A and 6B.

FIG. 11D shows a front cross-sectional view (taken along line B-B) of the device of FIGS. 6A and 6B.

FIG. 13A illustrates a top elevation view of another embodiment of the implantable device (after implantation) with the distraction mechanism positioned in the anterior aspect of the member.

FIG. 13B shows a side elevation view of the device of FIG. 13A (i.e., viewed along Direction A).

FIGS. 19-22 illustrate various perspective views of an implantable device distraction mechanism according to aspects of the present disclosure.

FIGS. 25A-25B illustrate cross sectional views of a targeted disc space, illustrating one exemplary approach thereto.

FIGS. 26A-26B illustrate exemplary cross-sectional views of a targeted disc space including an exemplary surgical corridor and bone graft material.

FIGS. 28-29 illustrate an exemplary method of accessing a facet space according to aspects of the present disclosure.

Figure 2B:
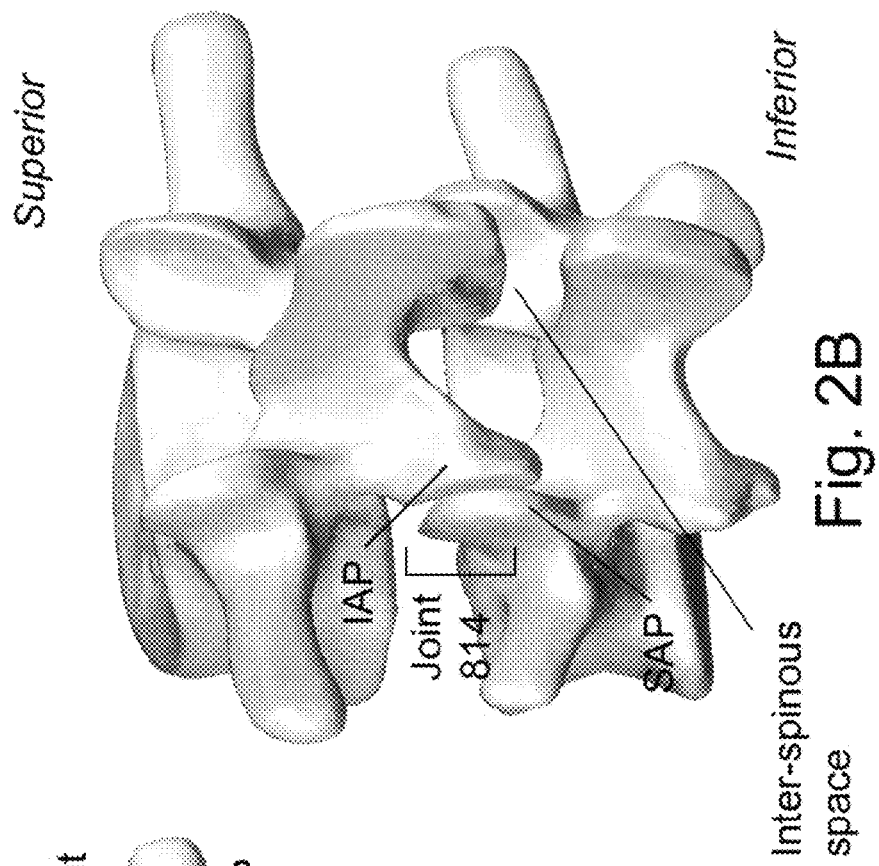
FIGS. 2A and 2B illustrate a functional spinal unit (FSU), which includes two adjacent vertebrae and the intervertebral disc between them.

All Figures © Copyright 2013-2020. Samy Abdou. All rights reserved.

DETAILED DESCRIPTION

In order to promote an understanding of the principals of the disclosure, reference is made to the drawings and the embodiments illustrated therein, and wherein like numerals refer to like parts throughout. Nevertheless, it will be understood that the drawings are illustrative and no limitation of the scope of the claims is thereby intended. Any such alterations and further modifications in the illustrated embodiments, and any such further applications of the principles of the disclosed devices as illustrated herein are contemplated as would normally occur to one of ordinary skill in the art.

Overview

In one aspect, improved devices, systems, and methods to alter vertebral alignment are described herein. Specifically, a variable height implantable device and its systems (e.g., related components) and methods of use are disclosed herein.

It will be appreciated that in a variety of disorders, the vertebral bones of a human (or other vertebrate organism) may become mal-aligned and produce, among other conditions, translational, rotational and/or angulational deformities of the spinal column. The devices and methods disclosed herein can advantageously be used in the treatment of many spinal disorders, such as, inter alia, coronal plane deformity (such as scoliosis), sagittal plane deformity (such as alternation in segmental kyphosis or lordosis), axial translation, vertical translation, spondylolisthesis, and the like.

In one implementation, a spinal segment to be surgically treated using the methods and apparatus disclosed herein includes at least a superior vertebral bone, an immediately inferior vertebral bone, and the intervening intervertebral disc space. A spinal segment comprised of two immediately adjacent vertebral bones and the intervertebral disc space disposed therebetween defines a "functional spinal unit" (FSU)—as described further below. An FSU to be surgically treated will be referred to as a target FSU and its intervertebral disc space as a target intervertebral disc space.

In one embodiment, a method of treatment includes entering the target intervertebral disc space and removing at least a portion of the viscoelastic material that comprises the natural nucleus pulposus within (at least a portion of) the intervertebral disc space. The target intervertebral disc space may be accessed using various surgical approaches (such as e.g., a direct anterior approach, an anterolateral approach, and/or a direct lateral approach, posterolateral approach, posterior approach, etc.), thereby creating one or more operative corridors at desired vertebral level(s) of the spinal column.

After removal of the viscoelastic material, the method further includes implanting a variable-height orthopedic implant into the target intervertebral disc space. The implanted orthopedic device is then actuated to vary a height of the implant in at least one aspect, and at least a portion of the implant is left in place in a substantially fixed position after the surgical procedure is complete.

The implanted apparatus enables, inter alia, customized (and heterogeneous) adjustment in distraction as between different target intervertebral disc spaces (and even different portions of the same target intervertebral space(s)). This is accomplished in one embodiment via use of one or more variable-geometry distraction mechanism used in conjunction with an implantable member, the latter which at least partly receives the former so as to create an implantable assembly that can be adjusted by the surgeon to achieve the desired geometry and spatial relationships.

Detailed Description of the Exemplary Embodiments

Exemplary embodiments of the apparatus and methods of the present disclosure are now described in detail.

It will be appreciated that while the exemplary embodiments are described with respect to human beings, various of the methods, apparatus and systems disclosed herein may be applied to other species having a spinal structure (i.e., vertebrates).

FIGS. 1A-1C show diagrammatic representations of a spinal vertebral bone 802 in multiple views. For clarity of illustration, the vertebral bone of FIGS. 1A-1C and those of other illustrations disclosed herein are represented schematically and it should be appreciated that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. It will be appreciated that the disclosed devices and methods may be employed at any applicable spinal level.

Additionally, the term "sagittal plane", as used herein, refers without limitation to the plane that splits the body into left and right segments. The terms "mid-sagittal plane" or "median plane", as used herein, refer to the plane that specifically splits the body into equal left and right halves. The term "coronal plane", as used herein, refers without limitation to the plane that divides the body into anterior (front) and posterior (back) segments. It will be appreciated that the coronal and sagittal planes are substantially perpendicular to one another.

As can be seen in FIGS. 1A-1C, the vertebral bone 802 contains an anteriorly-disposed vertebral body 804, a centrally-disposed spinal canal 806 and a posteriorly-placed lamina 808. The pedicle segments 810 of the vertebral bone 802 form the lateral aspects of the spinal canal 806 and connect the laminas 808 to the vertebral body 804. The spinal canal 806 contains neural structures such as the spinal cord and/or nerves. A midline protrusion termed the spinous process (SP) extends posteriorly from the medial aspect of laminas 808. A protrusion extends laterally from each side of the posterior aspect of the vertebral bone 802 and is termed the transverse process (TP). A right transverse process (RTP) extends to the right from the lateral aspect of the right pedicle. A left transverse process (LTP) extends to the left from the lateral aspect of the left pedicle. A superior protrusion extends above the lamina 808 on each side of the vertebral midline, and is termed the superior articulating process (SAP). An inferior protrusion extends inferiorly below the lamina 808 on each side of the vertebral midline, and is termed the inferior articulating process (IAP).

As a brief aside, it is noted that the posterior aspect of the pedicle 810 can be accessed at an indentation 811 in the vertebral bone 802 between the lateral aspect of the SAP and the medial aspect of the TP. In surgery, it can be common practice to anchor a bone fastener into the pedicle portion 810 of a vertebral bone 802 by inserting the fastener through indentation 811 and into the underlying pedicle 810 in a posterior to anterior direction.

Figure 2A:
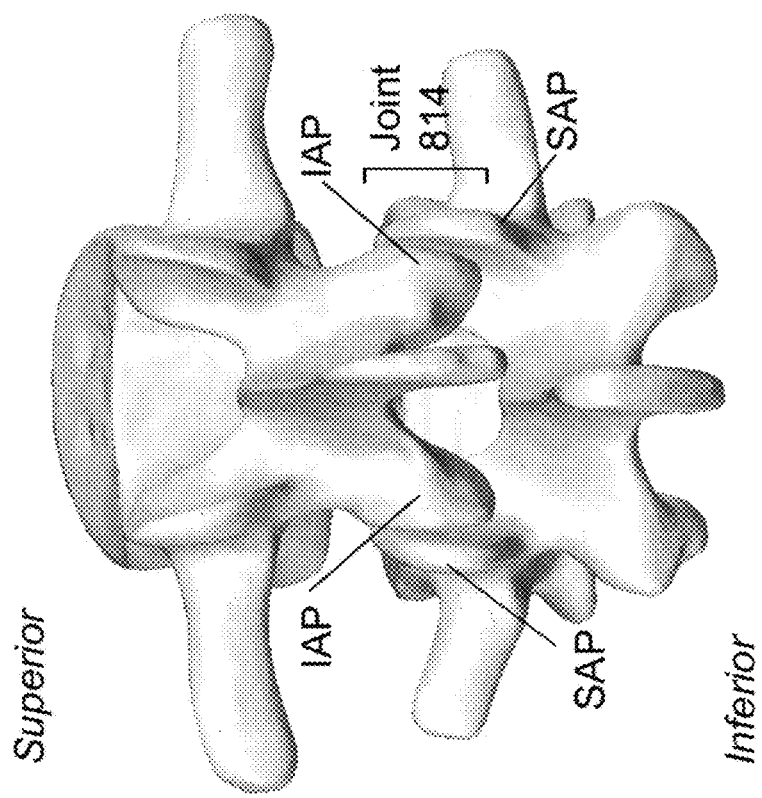

FIGS. 2A and 2B illustrate a functional spinal unit (FSU), which includes two adjacent vertebrae and the intervertebral disc disposed therebetween. The intervertebral disc resides between the inferior surface of the upper vertebral body and the superior surface of the lower vertebral body, although it is not specifically shown in the figures. FIG. 2A shows the posterior surface of the adjacent vertebrae and the articulations between them. FIG. 2B shows an oblique view. The FSU contains three joints between the two vertebral bones, with the intervertebral disc comprising the anterior joint. The posterior joints include a facet joint 814 on each side of the midline, wherein each facet joint 814 is comprised of the articulation between the IAP of the superior vertebral bone and the SAP of the inferior bone.

These illustrations and definitions of anatomical structures are known to those of ordinary skill in the art. They are described in more detail in *Atlas of Human Anatomy*, by Frank Netter, third edition, Icon Learning Systems, Teterboro, N.J., the entirety of which is incorporated herein by reference. It should be appreciated that the directional language and terms regarding orientation such as upper, lower, upward, downward etc., are used throughout merely for convenience of description and are not limiting.

A method of device implantation is now illustrated and described. One or more FSUs is/are targeted for surgical manipulation and treatment. In preparation for surgery, the patient can be, but is not necessarily, placed in a lateral decubitus position, such as that shown in FIG. 3. It is understood that a target intervertebral disc space may be accessed using any known surgical approach, and the illustrated method serves as a non-limiting example.

Figure 4:
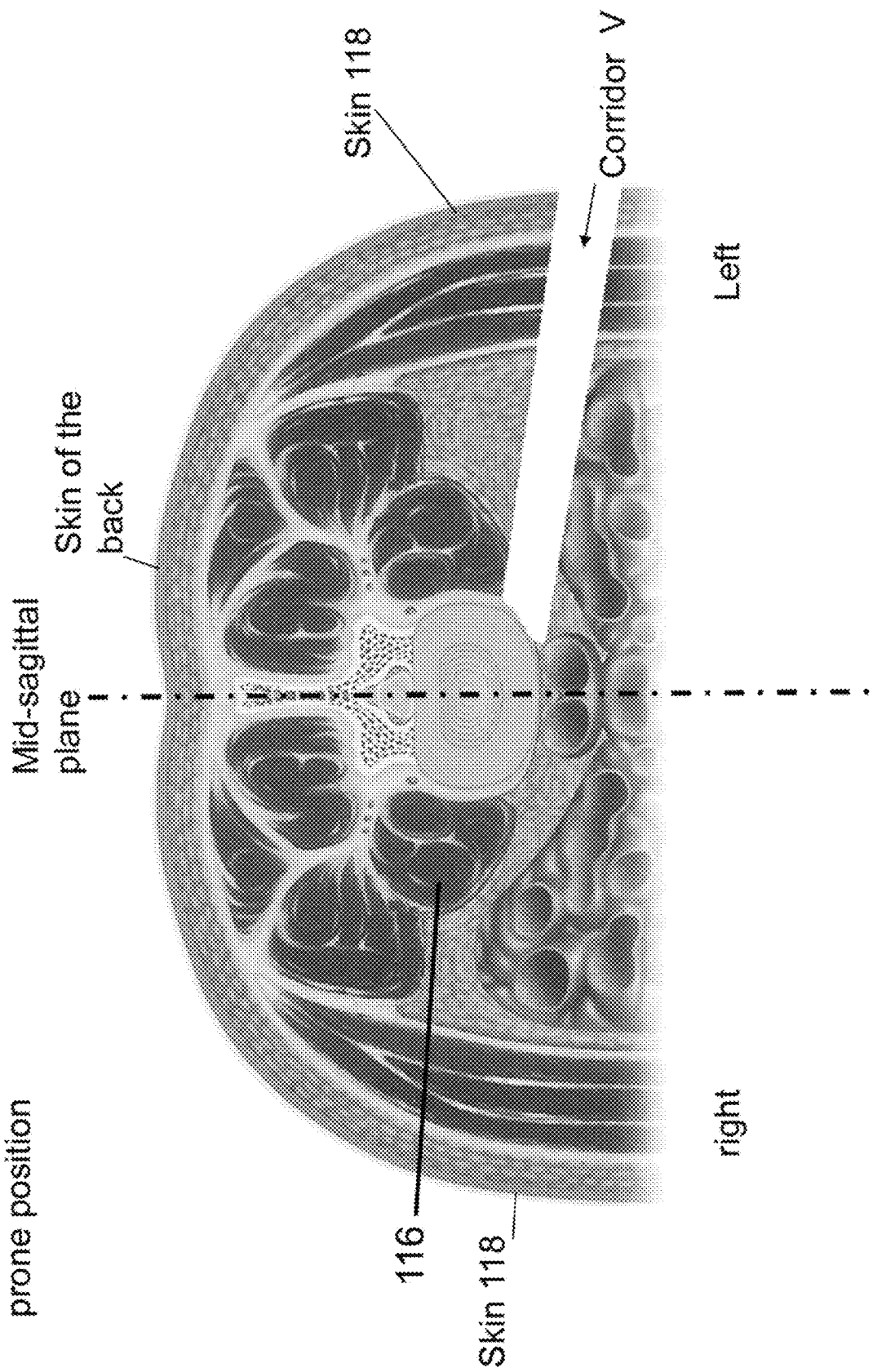
FIG. 4 illustrates a cross sectional view of the torso at the level of a targeted disc space in the lumbar spine.

The level(s) of the spine that is to be implanted can be localized on an imaging modality (such as X-ray, CT, MRI and the like) in at least one plane. After the customary sterile preparation of the operative site, the surgeon can localize an incision point on the skin that is anterior to coronal plane T. Preferably, but not necessarily, the incision may be made immediately anterior to a coronal plane that is parallel to coronal plane T and passes through the anterior-most (tip) aspect of the target disc space. A lateral corridor "V" (FIG. 4) can be made through the skin 118 from the flank incision and taken onto the target intervertebral disc space. In the illustrated embodiments, the disc space may be entered using one or more of three locations shown in FIG. 5; i.e.: a) medial to the aorta and may comprise the midline (and/or its branches, the common iliac arteries, etc.) to form a direct anterior approach (505); b) lateral to the aorta but anterior to the Psoas Major muscle—to form an anterolateral approach (507); and c) laterally and through the body of the Psoas Major muscle—to form a direct lateral approach (509). The insertion corridor of a direct lateral approach is known to those skilled in the art as the "XLIF" procedure, among other names. See *"Extreme Lateral Interbody Fusion (XLIF): a novel surgical technique for anterior lumbar interbody fusion"*—Ozgur, Aryan et al. in *Spine J.* 2006 July-August; 6(4):435-43, which is incorporated herein by reference in its entirety.

Figure 5:
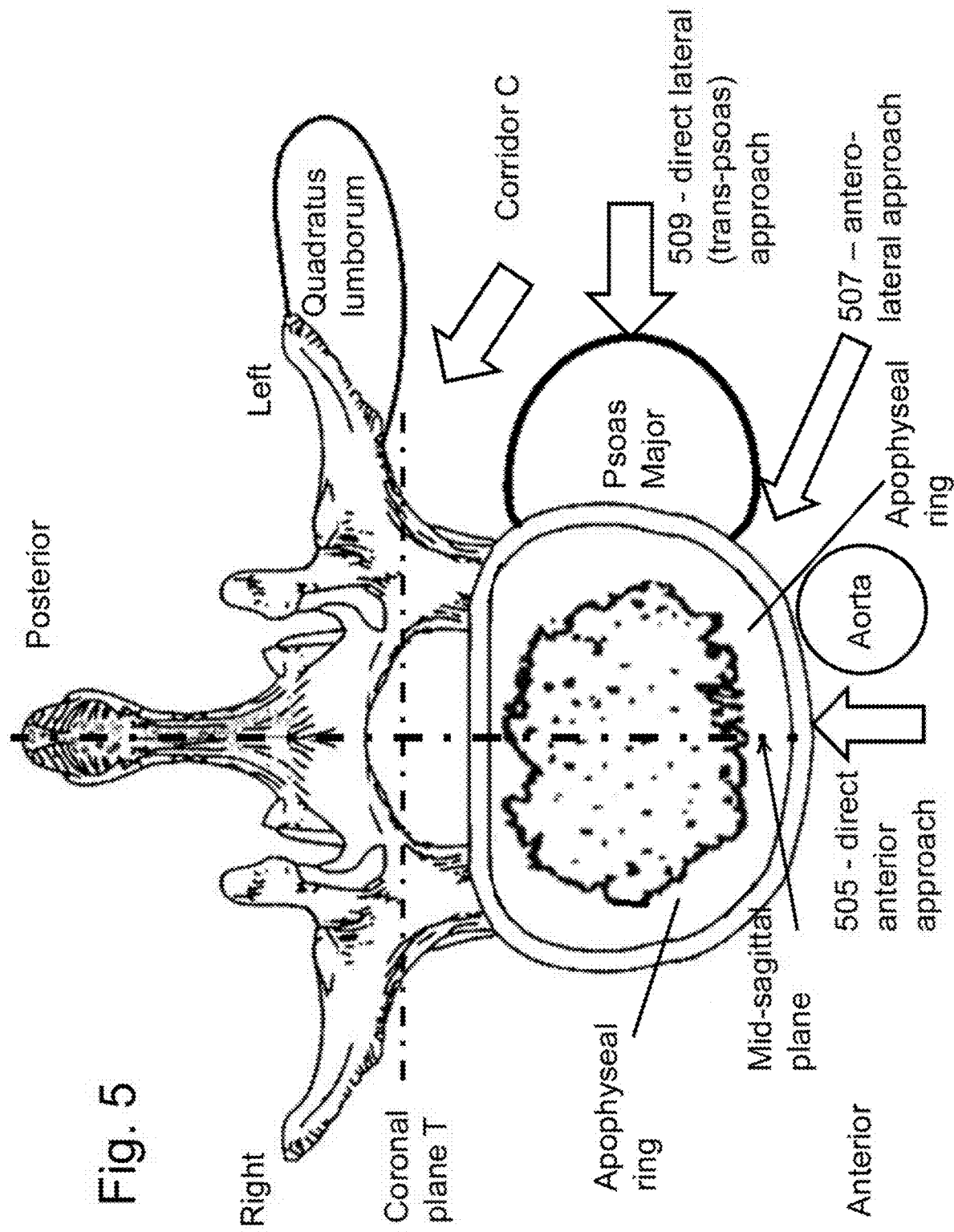
FIG. 5 illustrates a cross sectional view of a targeted disc space in the lumbar spine, illustrating various approaches thereto.

In one implementation of the method, the target intervertebral disc space is entered using the anterolateral approach 507, shown in FIG. 5, which is at least partially positioned between the lateral Aorta and the anterior surface of the ipsilateral Psoas major muscle. After removal of at least a portion of the nucleus pulposus of the target intervertebral disc space, a variable-height implant 104 (see FIG. 6A) may be placed into the disc space. Preferably, the implant 104 extends across the midsagittal plane of the disc space with one end segment positioned onto the left side of the apophyseal ring of the inferior vertebral bone and a second end segment positioned on the right side of said apophyseal ring (as subsequently shown and discussed with respect to FIGS. 12A and 12B), although it will be appreciated that other orientations and dispositions may be used (as subsequently shown and discussed with respect to FIGS. 13A and 13B). Additionally, the present disclosure contemplates that the implants 104 may be configured with a more round or oval form factor, and rotated at varying degrees (e.g., around an axis generally co-linear or parallel with the spinal column of the patient) so as to best accommodate the particular configuration of the prevailing target intervertebral disc space. Moreover, such rotations or other positional variations may be applied on a per-implant basis; e.g., wherein one target space uses one rotation/orientation, and another target space within the same patient uses another.

In one variant of the method, the superior and inferior vertebral bones of the target FSU are distracted away from one another in order to increase the vertical height of the target intervertebral disc space during implantation. Such optional distraction step may be performed with, for example, one or more distraction instrument(s) or devices that are used during surgery, and which are removed prior to the end of the procedure or after placement of the orthopedic implant(s); however, it is also recognized that dissolvable, inflatable, or other means of distracting may be utilized, other than the one or more removable distraction devices previously referenced.

In another embodiment, the method includes inserting a variable-height implantable device into a target intervertebral disc space in order to change the coronal plane alignment of the target FSU. The implant may be placed into the target intervertebral disc space using any of the known surgical approaches, such as, for example, the direct anterior approach, the anterolateral approach, and/or the direct lateral approach, discussed supra.

Figure 12A:
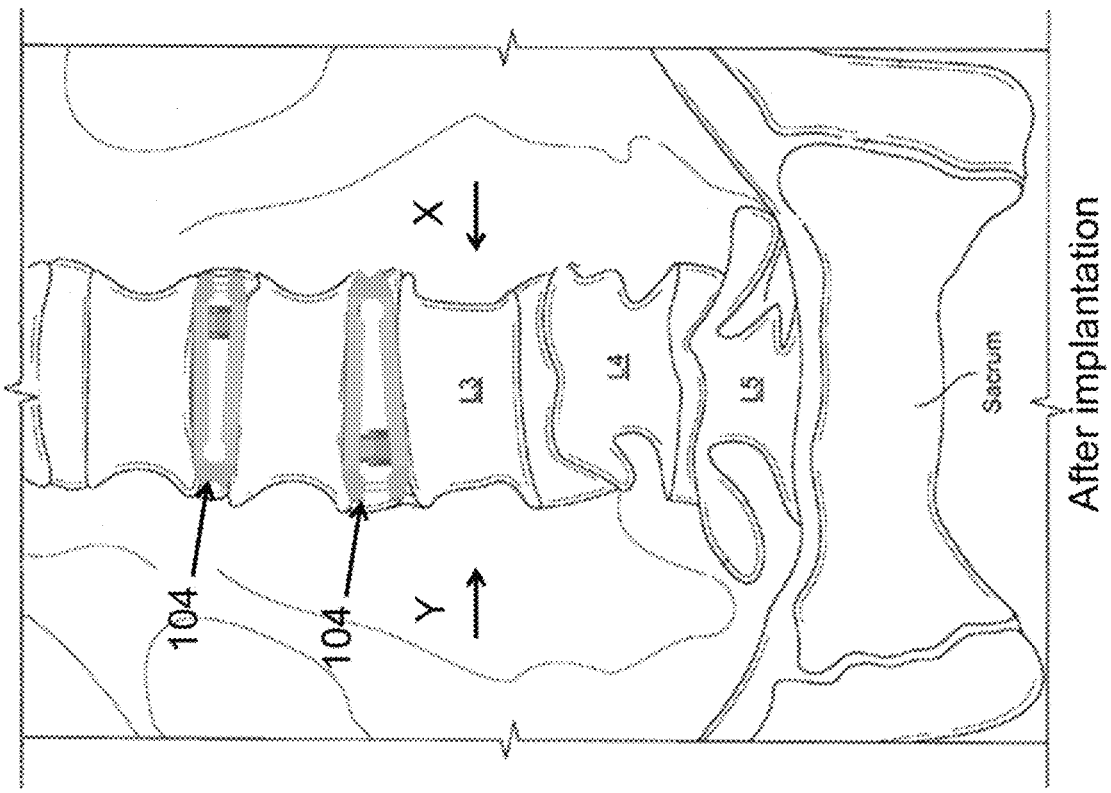
FIG. 12A shows a front elevation view of a lumbar spine with a coronal plane deformity (such as, for example, scoliosis).
Figure 12B:
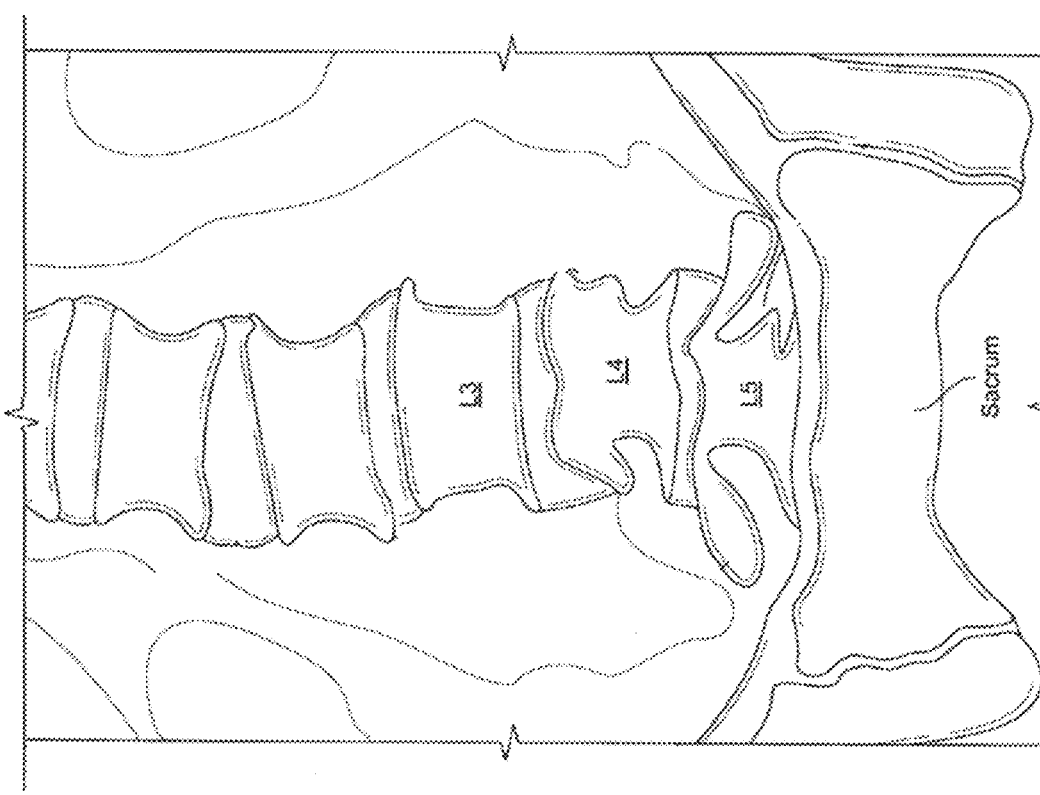
FIG. 12B shows a front elevation view of the lumbar spine of FIG. 12A with the device installed to produce a deformity (scoliosis) correction.

In one variant of the method, the implant is inserted with the first lateral side of the implant (i.e., a side of the implant that will be positioned closest to a first lateral side surface of the target intervertebral disc space) having a height that is less than or equal to the height of the second lateral side (i.e., a side of the implant side that will be positioned closest to the second lateral side surface, opposing the first lateral side surface, of the target intervertebral disc space) (see FIGS. 12A and 12B). After the implant is positioned at a desired position within the target intervertebral disc space, a mechanism of the implant is actuated so as to increase the height of one, but not both, of the first lateral side or the second lateral side of the implant. Thus in one implementation, a coronal section though the implanted intervertebral disc space will show that the implant, after actuation of the distraction mechanism, is wedge-shaped with the distance between the inferior surface of the superior vertebral bone and the superior surface of the inferior vertebral bone being greater on one lateral side surface of the target intervertebral disc space than on the opposing lateral side surface of said disc space.

In another variant, the implant comprises an anterior side (i.e., a side of the implant that will be positioned closest to the anterior midline (mid-sagittal) of the implanted intervertebral disc space) and an opposing posterior side (i.e., a side of the implant that will be positioned closest to the posterior midline (mid-sagittal) of the implanted intervertebral disc space) (see FIGS. 13A and 13B). The implant is positioned at the desired position within the intervertebral disc space, and then the mechanism within the implant is actuated so as to increase the height of one, but not both, of the anterior side or the posterior side of the implant. Thus in one implementation, a mid-sagittal section though the implanted intervertebral disc space will show that the implant, after actuation of the distraction mechanism, is wedge-shaped with the distance between the inferior surface of the superior vertebral bone and the superior surface of the inferior vertebral bone being greater at one of the anterior or posterior side sides of the implanted intervertebral disc space than at the opposing side of the target disc space.

FIGS. 6A and 6B illustrate an embodiment of the variable-height implant having a distraction mechanism according to the present disclosure. The illustrated implant 104 may, for example, comprise a first member 105 (i.e., a host member) having an "upper" element 1051a with superior surface adapted to abut the inferior surface of the vertebral bone immediately superior to the target disc space, and a "lower" element 1051b with an inferior surface adapted to abut the superior surface of the vertebral bone immediately inferior to the target disc space. The superior and inferior surfaces are connected by at least one side surface. In the present embodiment, a hinge 1052 or other mechanism for articulation is positioned at one side of upper and lower elements 1051a, 1051b and is configured to allow the inferior surface to move relative to the superior surface, thereby increasing a distance therebetween. The hinge may be a malleable or even frangible member that is connected each of the superior and inferior surfaces. Alternatively or additionally, the hinge may comprise two abutment or engagement surfaces, each disposed on one of the superior and inferior surfaces of the first member, which rotate about a common axis (such as, for example, about a central pin). Cavities 1054 open within and/or onto the superior and inferior abutment surfaces and are adapted to accept and/or house a bone forming material (including, e.g., allograft and autograft bone) in order to form a bony fusion across member 105 and between the superior and inferior vertebral bones.

As can be seen in FIGS. 6A and 6B, the variable-height implant 104 further comprises a distraction mechanism 205 (i.e., a second expandable member), which is configured to be at least partially positioned within and/or at least partially seated within the first member 105. FIG. 6A illustrates a position for the insertion of the distraction mechanism 205 into the first member 105. After the distraction mechanism 205 is seated within the first member 105 (as in FIG. 6B), a surface 20544 extends through a window 1053 of the first member 105. A surface 20542 of mechanism 205 abuts the undersurface of upper element 1051a of the first member 105. Thus, when the distraction mechanism is seated, the surface 20542 abuts the first member 105, whereas the surface 20544 abuts the vertebral bone. This is further illustrated in the sectional view of FIG. 11B.

In one embodiment, upon actuation, the distraction mechanism 205 increases a height of at least one side of the first member 105. For example, upon actuation of the distraction mechanism 205, a distance between the upper and lower elements 1051a, 1051b is increased on at an expandable side 1058 (i.e., an end opposing the hinge 1052) of the first member 105. In alternate examples, the distraction mechanism may increase the height of more than one side of the first member 105. However, as illustrated herein (see FIGS. 7B and 11B), the increase in height is at least greater on one side (i.e., the expandable side 1058) than the other side(s)—so that the implant assumes a "wedge-like" configuration that can be used to realign spinal bones.

An exemplary contracted position 1040 of the implant 104 is shown in FIG. 7A, while an exemplary expanded position 1042 is shown in FIG. 7B. It will be appreciated that the implant 104 can be adjusted to assume various intermediate positions and/or positions having a greater distance between the upper and lower elements 1051a, 1051b. It is noted that, during implantation, the first member 105 is preferably inserted into the disc space in a configuration where the opposing sides are of substantially equal height (position 1040 of FIG. 7A). After implantation of the implant 104, subsequent actuation of the distraction mechanism 205 will cause the first member 105 to assume a wedge-shaped configuration (position 1042 of FIG. 7B).

In one implementation, the distraction mechanism 205 is adapted to be delivered to the surgeon as a separate device, and then installed within the first member 105 at the time of the procedure. As discussed elsewhere herein, alternatively, the distraction mechanism can be integral to the first member. Notably, the distraction mechanism 205 may be configured to be utilized with other configurations or types of implants (not shown) other than the first member 105 of the depicted implant device 104. Additionally or alternatively, the portions of the first member 105 which receive the distraction mechanism 205 can be made of a standardized configuration, such that any given distraction mechanism can be fitted with any member 105 (such as, e.g., dependent on a specific treatment or specific spinal condition). Alternatively, heterogeneous sizes and/or overall expanded/fully contracted lengths of distraction may be provided. For instance, in one such approach, three (3) sizes are provided (e.g., small, medium, and large) for different sized implant devices 104, such as for target intervertebral disc spaces (or patients) of different sizes. It is also appreciated that a single distraction mechanism 205 can be substituted (with proper adaptation of the receiving host member 105) with two or more smaller mechanisms and/or the first member 105 may be configured to receive two or more distraction mechanisms at various locations within the member, such as to permit finer adjustment of various particular portions (e.g., anterior and/or posterior portions) of the implant relative to the inferior/superior surfaces of the vertebrae which it engages when installed.

As can be seen in FIG. 8, the expandable side 1058 (i.e., the non-hinged side opposing the hinge 1052) of the first member 105 may comprise two or more segments or pins 1056 or other such mechanisms, which may be configured to, inter alia, provide added rotational stability to one or more of the implant sides. In some implementations, these pins or segments can also be configured to enable fastening or locking of the upper and lower elements 1051*a*, 1051*b* relative to one another after the distraction mechanism(s) 205 has been inserted within the first member 105, and/or after the implant 104 has been inserted into the target intervertebral space. For instance, the pins may comprise threaded or rotation-lockable couplings which engage the upper and lower elements 1051*a*, 1051*b* so as to "clamp" the variable-height implant 104 and/or the distraction mechanism 205 in place once the desired configuration (e.g., a desired height of the expandable side 1058 of the first member 105) is achieved.

FIG. 9 illustrates multiple views of the exemplary embodiment of the distraction mechanism 205. Many embodiments of expandable interbody implants are known in the art, and these devices employ a host of differing mechanisms for device expansion and/or actuation. These mechanisms include, but are not limited to, mechanical linkages, wedges, pulleys, balloons, magnets, and/or pistons. It will be appreciated that while a fluid-based piston assembly is shown as one option (e.g., using a substantially incompressible working fluid), a compressible fluid (e.g., gas-based) working fluid may be used in certain alternate embodiments, as may a purely mechanical (i.e., non-fluidic) mechanism, such as a worm-screw drive, gear mechanism, or the like.

For example, in one embodiment, the distraction mechanism may comprise a worm screw drive or gear mechanism and an associated ridged track, which is configured to be turned (wound) via an attachable and/or insertable adjustment tool. The tool may be operated in a first rotational direction to increase a height of the distraction mechanism 205, thereby increasing a distance between upper and lower elements 1051*a*, 1051*b*. Further, in some examples, the tool may be operated in a second rotational direction to decrease a height of the distraction mechanism 205, thereby decreasing a distance between upper and lower elements 1051*a*, 1051*b*. Various exemplary mechanical (non-fluidic) mechanisms that can be adapted into the distraction mechanism 205 for use in combination with the first member 105 are shown and described in U.S. Pat. No. 7,909,870 and U.S. Patent Publication No. 2003/0163199, each of which is incorporated herein by reference in its entirety.

In another embodiment, the distraction mechanism may comprise a balloon made of either non-compliant or compliant material which may be porous or non-porous, or may include a mesh material which may be coated or lined with a porous or non-porous material. The balloon may further include a port for coupling to a source of an inflation and/or expansion medium (e.g., a gas, a liquid, a semi-solid, a gel, a liquid that hardens into a solid material, etc.) for inflating and/or expanding the distraction mechanism. The devices may further include one or more anchoring or attachment features for fixing the balloon within the first member 105. Actuation of such an embodiment of the distraction mechanism may involve inflation of the balloon with the expansion medium, wherein the act of balloon inflation provides at least part of the force needed to produce (i) the change in configuration of the structure of the housing/structure distraction mechanism (such as an increase in the height of the housing or a change in its dimension, such as length and/or width, of a segment of the housing, and/or (ii) the force needed to produce the change in configuration of the first member 105 (such as increase in a distance between the upper and lower elements 1051*a*, 1051*b* on at least one end (e.g., the expandable side 1058) of the first member 105). An exemplary balloon driven distraction mechanism that can be adapted into the distraction mechanism 205 for use in combination with the first member 105 is shown and described in U.S. Pat. No. 8,123,807, which is incorporated herein by reference in its entirety.

While the distraction mechanism 205 is illustrated as a piston-based distraction mechanism, it is understood that any distraction mechanism (such as one or more of those described supra) may be alternatively employed.

Notably, the distraction mechanism 205 may also be configured for reversible mating with the first member 105 intra-operatively, when handled by the surgeon. That is, the distraction mechanism may have one or more degrees of chirality or "handedness," such that (i) it can be inserted in one orientation, and also in the opposite orientation (e.g., rotated 180-degrees from the first orientation around an axis generally parallel to the patient's spine), and/or (ii) can be inverted such that its otherwise superior surface can function as its inferior surface, or vice versa). The foregoing approaches advantageously mitigate the implanting surgeon "fumbling" with the mechanism 205 during surgery to achieve the proper orientation, and more importantly can avoid any instances where the mechanism 205 is installed in an improper orientation within the host member 105. To that end, the mechanism 205 and its host member 105 may also include mechanical alignment features such as keys, indexing, pins, etc. such that it can only be inserted one way. Additionally or alternatively, the distraction mechanism may be intra-operatively removable from the first member 105, when handled by the surgeon. That is, in an example where the pins 1056 provide clamping or locking of the first member 105 after distraction caused by the distraction member 205, the distraction member may be reversibly distracted (i.e., its height decreased) and removed from the first member prior to completion of the surgical procedure, while the first member retains its wedge-like configuration.

FIG. 10 illustrates an exemplary configuration of the constituent members 2054 and 2058 of the distraction mechanism 205. In the exemplary configuration, a piston 20546 is received within a cavity 20586 of the member 2058. Side protrusions 20548 are each received within cavities 20588 and function to provide, inter alia, alignment and rotational stability to the distraction mechanism 205. The member 2054 has surfaces 20542 that abut the undersurface of the superior surface 1051*a* of the first member 105, whereas surface 20544 extends through the window 1053 (see FIGS. 6B and 11B). In certain embodiments, multiple sub-segments (such as sealants/gaskets, O-rings, etc.), which may be used with the described piston-based approach, are known components of piston devices, and are not repeated here for diagrammatic simplicity. Note that in one implementation, the distraction mechanism 205 contains multiple apertures 20581 and 20583 that allow filling and/or bleeding of the working fluid from the piston chamber. See also, e.g., U.S. Patent Application Publication No. 2007/0093901, herein incorporated by reference in its entirety, which describes the exemplary use of pistons in the manufacture of an expandable interbody implant, such as may also be used within the distraction mechanism 205 described above.

Advantageously, the exemplary embodiment of the distraction mechanism 205 is configured such that it can be actuated from at least two separate sides. That is, the aperture(s) 20583 is/are formed within a first surface and the aperture(s) 20581 is formed within a second surface of mechanism 205. Hence, different directions of approach can be used to actuate the distraction mechanism 205. In one implementation, the distraction mechanism 205 is configured to actuate whether the actuation tools approach (e.g., are attached to it) from either or both of Direction F or Direction G of (FIG. 7B); i.e., from one side of the device 104 or the other. For example, either or both of handles 10590 illustrated in FIG. 7A can be used actuate the distraction mechanism 205. The handles 10590 can also be provided regardless of the nature of the distraction mechanism used (mechanical linkages, wedges, pulleys, balloons, magnets, pistons and the like), such that the device may be actuated whether the first member 105 is approached from one side or the opposing second side. FIGS. 11A and 11B illustrate sectional views of the exemplary embodiment of the distraction mechanism 205 alone (FIG. 11A), and with the distraction mechanism 205 positioned within the first member 105 (FIG. 11B).

FIGS. 12A and 12B illustrate an example of a spinal deformity correction that may be achieved with use of one or more aspects of the disclosed invention(s). In one implementation, a surgeon may be given a kit comprising the first member 105, the distraction mechanism(s) 205, and handling or installation instruments for, at least, positioning said members, and/or actuation of the distraction mechanism(s) 205 (such as handle(s) 10590). The patient can be prepared and a surgical procedure performed by the surgeon as described above.

Exemplary Applications

In one embodiment, a variable-height implant may be configured to form a lateral wedge configuration and be used to alter the spinal alignment of a target functional spinal unit in the coronal plane in order to treat coronal plane deformities such as, e.g., scoliosis. FIG. 12A shows a lumbar spine with a coronal plane deformity (such as, for example, scoliosis). Application of the variable-height implant 104 (comprising both the first member 105 and the distraction mechanism 205) via one or more of the surgical procedures described above produces the deformity (scoliosis) correction shown in FIG. 12B. Note that the implant 104 advantageously may be implanted from either side of the spine (along either of directions "X" or "Y"; however, implantation of the depicted inferior (lower) implant, in the direction X, would be impossible under the prior art. For example, an implant having a fixed wedge shape (i.e., having a first side of a greater height than a second opposing side) is implantable from only one side of the target intervertebral disc space. Specifically, the foregoing fixed wedge implant can only be inserted into a disc space leading with the second opposing side (the side having a smaller height) and trailing with the first side (having a greater height).

Returning to FIG. 12B, in one exemplary application of the present invention, the variable-height implant 104 is passed into the target disc space along direction X, while the implant is in the collapsed configuration 1040 (FIG. 7A) and the leading edge (the edge that enters the disc space first) is of lesser or equal height to the trailing edge of the implant (i.e., the edge that enters the disc space last). In an alternate exemplary application, the variable-height implant 104 is passed into the target disc space along direction Y, while the implant is in the collapsed configuration 1040 (FIG. 7A). In either application, the distraction mechanism 205 may be actuated after placement of the (assembled) implant 104 into the target disc space.

It will be appreciated, however, that in the alternate exemplary application, the variable-height implant 104 may passed into the target disc space along direction Y, while the implant is in the expanded configuration 1042 (FIG. 7B) or a partially expanded configuration, after full or partial actuation of the distraction mechanism 205.

It will be further appreciated that the assembly of the implant device 104 may be conducted after the first member 105 is inserted into the target disc space in some cases. Specifically, in one variant, the first member 105 alone is inserted in the direction X into the target space, and then subsequently, the surgeon accesses the disc space (and implant host member 105) via a different approach. In another variant, the first member 105 alone is inserted via an anterior approach (having a larger surgical corridor) into the target disc space, and then subsequently, the surgeon accesses the disc space (and the first member 105) via a posterior approach (having a smaller surgical corridor). In each of the foregoing variants, the distraction mechanism 250 is initially in its completely compressed state (i.e., smallest possible vertical profile, such that the surgeon can slide the mechanism 250 into e.g., a lateral groove formed on the first member 105 (not shown), or even separate the upper and lower elements 1051a, 1051b far enough while in the disc space such that the distraction mechanism can be inserted therebetween (and subsequently expanded as described supra).

As previously discussed, a variable-height implant may be configured to form an anterior to posterior wedge configuration and be used to treat sagittal plane deformity such as, e.g., abnormal lordosis and/or kyphosis—as shown in the implant 104a of FIGS. 13A and 13B. This device embodiment may be used to correct sagittal plane deformity, and would be employed to perform the "second method embodiment" discussed above. (It is understood that whether used to correct coronal or sagittal plane deformity, the implant may be delivered into the disc space using any known surgical approach for device implantation. Specifically, approaches 505, 507 and/or 507 of FIG. 5, may be employed).

FIG. 13A illustrates the implant 104a when viewed from above (for example, after implantation) including a distraction mechanism 205a positioned in the anterior aspect of a first member 105a (including three pins 1056a). FIG. 13B shows a side view—as would be seen with the device of FIG. 13A is viewed along direction A. It will be appreciated that the implant 104a may be used with any of the surgical procedures and may include the variations discussed herein. It will be further appreciated that the variable height implant 104a (in use) can be included in a kit with and/or used in combination with the implant 104 during a surgical procedure.

In yet another embodiment, a variable-height implant may be configured to form a wedge configuration used to treat translational deformities such as e.g., anterior/posterior or lateral spondylolisthesis.

It will be appreciated that the flexibility in use and configuration, as well as the modularity, of the first members 105, 105*a* and the distraction mechanisms 205, 205*a* are advantageous over prior implantation devices and methods. In other words, the configuration of the implant assembly and the method of implantation can be adapted by a surgeon to be spinal condition and/or patient specific. Such specificity may enable a surgeon to map out and prepare the implant components and surgical strategy prior to the implantation procedure. Alternatively, the surgeon can respond "on the fly" as a surgery progresses, if necessary, to provide a "best fit" implant configuration and implantation process (particularly in response to unforeseen issues that may unexpectedly arise and/or in treatment of especially complex spinal conditions). For example, any of the first members 105, 105*a* or the distraction mechanisms 205, 205*a* can be utilized as a free standing implant (e.g., where the distraction mechanism is implanted in the target disc space and actuated without prior insertion into the first (host) member, where the first member is inserted without a distraction mechanism and does not require distraction after implantation, where the first member is implanted with and distracted by the distraction mechanism, which is subsequently removed from the first member, etc.), and/or they can be used in combination (e.g., where the distraction mechanism is fitted within and is actuatable within the first member, as described supra). In other examples, various implant assemblies can be used in combination within the same target FSU or other target FSUs (e.g., adjacent FSUs) to treat complex spinal curvature conditions. The various implant assemblies can be inserted from any desired approach and/or entry point of the target FSU (such as those discussed supra).

Exemplary Embodiment of an Implant

The segment to be surgically treated is comprised of at least a superior vertebral bone, an immediately inferior vertebral bone and the intervening intervertebral disc space. (A segment comprising two immediately adjacent vertebral bones and the intervertebral disc space between them is called a "functional spinal unit" (FSU)—as will be discussed further below. The functional spinal unit to be surgically treated will be referred to as the target functional spinal unit and its intervertebral disc space as the target intervertebral disc space.) In an embodiment, the target intervertebral disc space is entered and at least a portion of the viscoelastic material that would comprise the natural nucleus pulposus is removed. The target intervertebral disc space may be accessed using any known surgical approach—including, but not limited to, anterior, anterolateral, lateral, posterior-lateral or posterior approaches.

Figure 14:
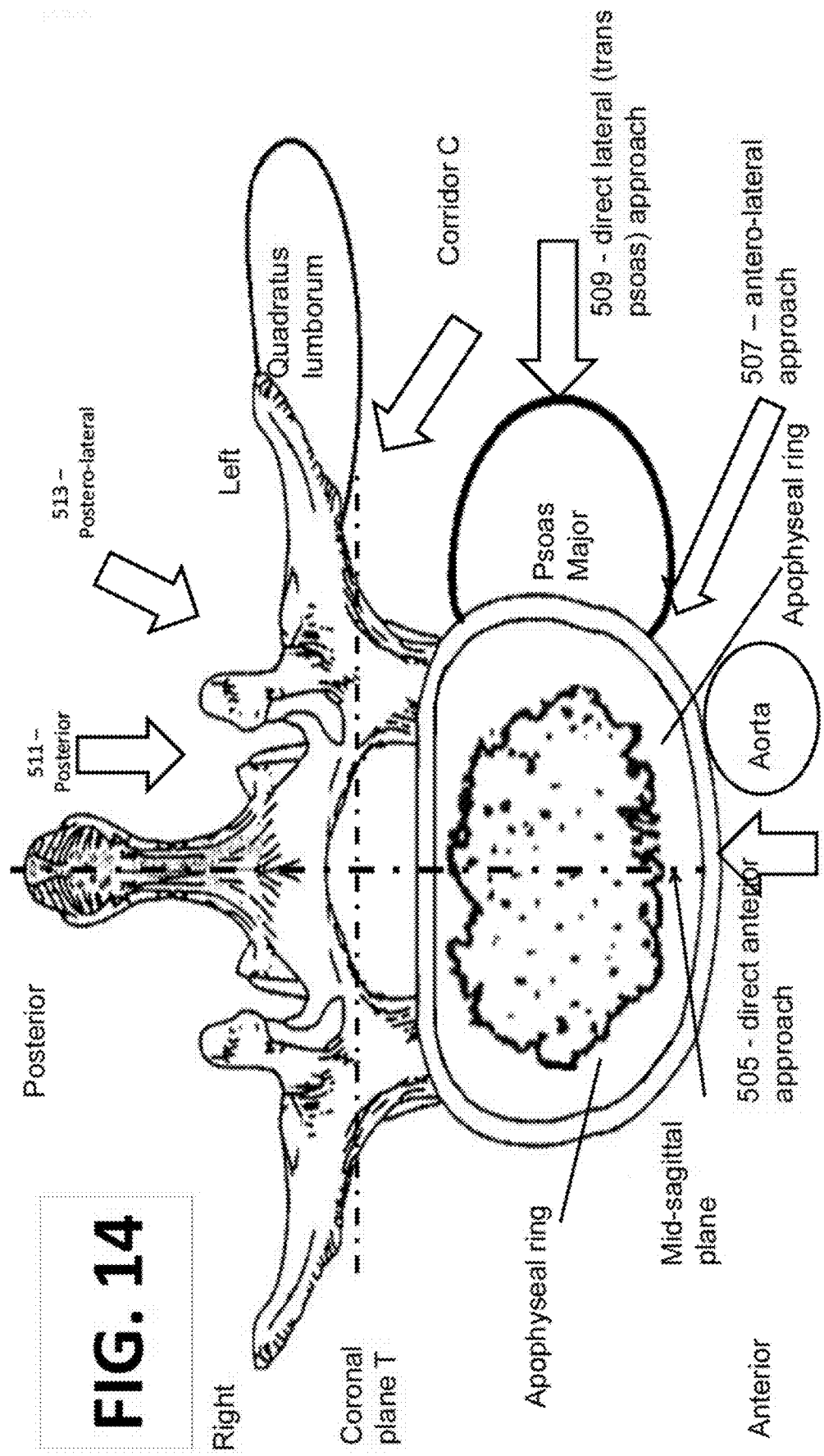
FIG. 14 illustrates an exemplary cross sectional view of a targeted disc space in the lumbar spine, illustrating various approaches thereto.

Referring to FIG. 14, in anterior, anterolateral or lateral approaches, the target disc space may be entered through the abdominal cavity using at least one or more of the three following locations: a) 505, medial to the aorta and may comprise the midline (and/or its branches, the common iliac arteries, etc) to form a direct anterior approach; b) 507, lateral to the aorta but anterior to the Psoas Major muscle—to form an anterolateral approach; and c) 509, laterally and through the body of the Psoas Major muscle—to form a direct lateral approach (FIG. 14). After removal of the viscoelastic material, an orthopedic implant may be implanted into the target intervertebral disc space using the same surgical corridor and then left in place after surgery is complete. Additionally, the superior and inferior vertebral bones may be distracted away from one another in order to increase the vertical height of the target intervertebral disc space. The optional distraction step may be performed with distraction instrument(s) that are transiently used during surgery and then removed prior to the end of the procedure or by said orthopedic implant(s) that is positioned during surgery and left in place.

Figure 3:
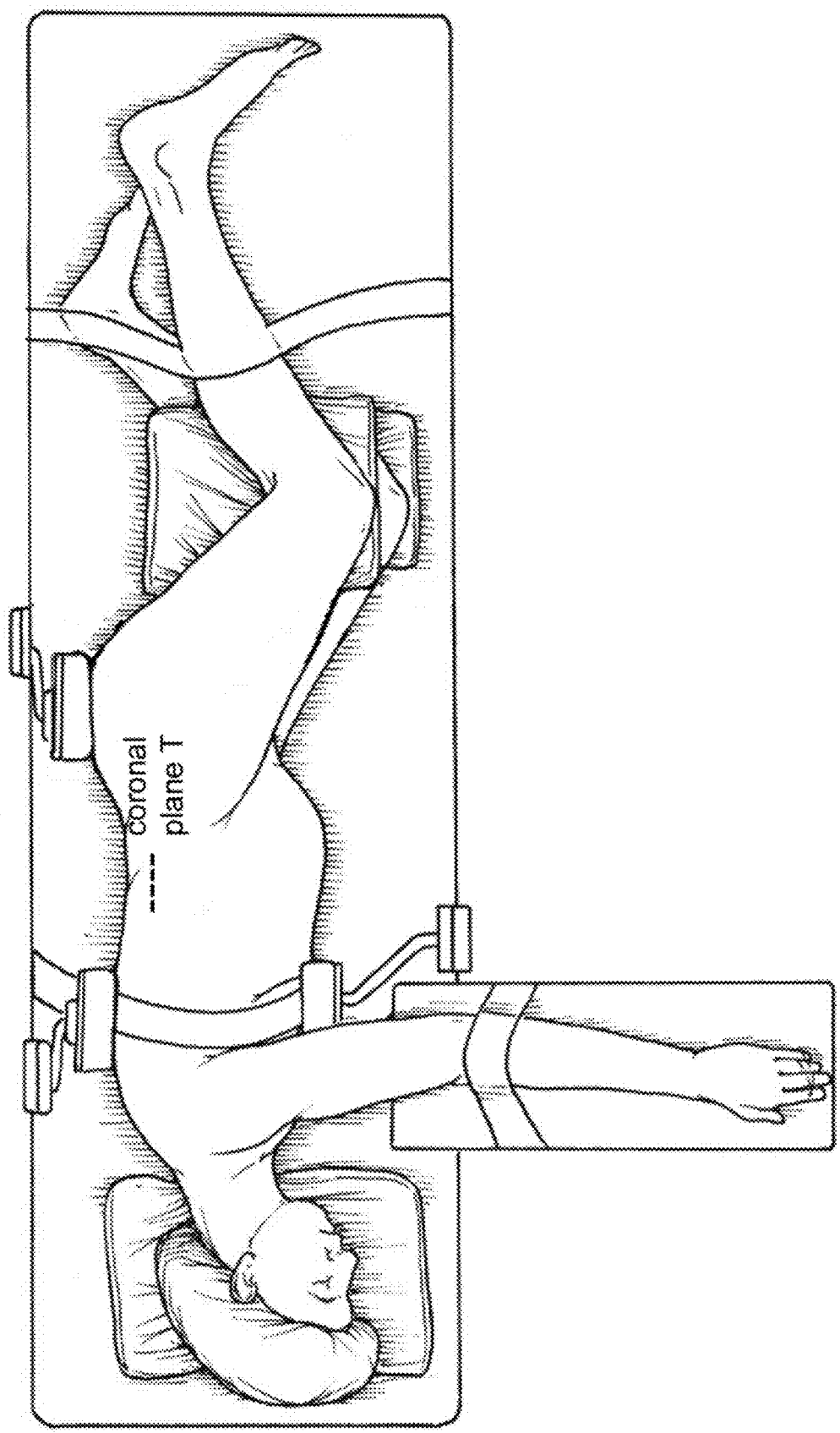
FIG. 3 shows a schematic representation of the posterior aspect of a patient who is positioned in a lateral decubitus orientation.

The insertion corridor of approach 509 is known to those skilled in the art as the trans-psoas approach, direct lateral (DLIF), Extreme Lateral Interbody Fusion (XLIF) approach, among other names. (See "Extreme Lateral Interbody Fusion (XLIF): a novel surgical technique for anterior lumbar interbody fusion." By Ozgur, Aryan et al. in *Spine J.* 2006 July-August; 6(4):435-43, which is hereby incorporated by reference in its entirety.) The insertion corridor of approach 511 and 513 is performed using a posterior surgical approach that is posterior to coronal plane T (FIG. 3). These approaches do not require traversing the abdominal cavity but provide limited access windows through which the implant may be positioned into the intervertebral disc space since the spinal canal, and the nerves contained therein, limit the corridor size.

In a first embodiment, an implantable device is inserted into an intervertebral disc space in order to change the alignment of the spinal segment containing the implanted intervertebral disc space. The implant may be placed into the intervertebral disc space using any of the known surgical approaches, such as, for example, approach 505, 507 509, 511 and/or 513 discussed above.

In one aspect of the disclosure, the implant comprises at least two members, the first being a housing (which may comprise more than one segment), the housing configured to abut each of the vertebral bones superior and inferior to the target intervertebral disc space into which the implant is positioned. In an embodiment, the first member is not a balloon but is comprised of a solid material. In one variant, the solid material is malleable and adapted for implantation into a human or animal subject. In another embodiment, the first member is at least partially comprised of a balloon.

Figure 15:
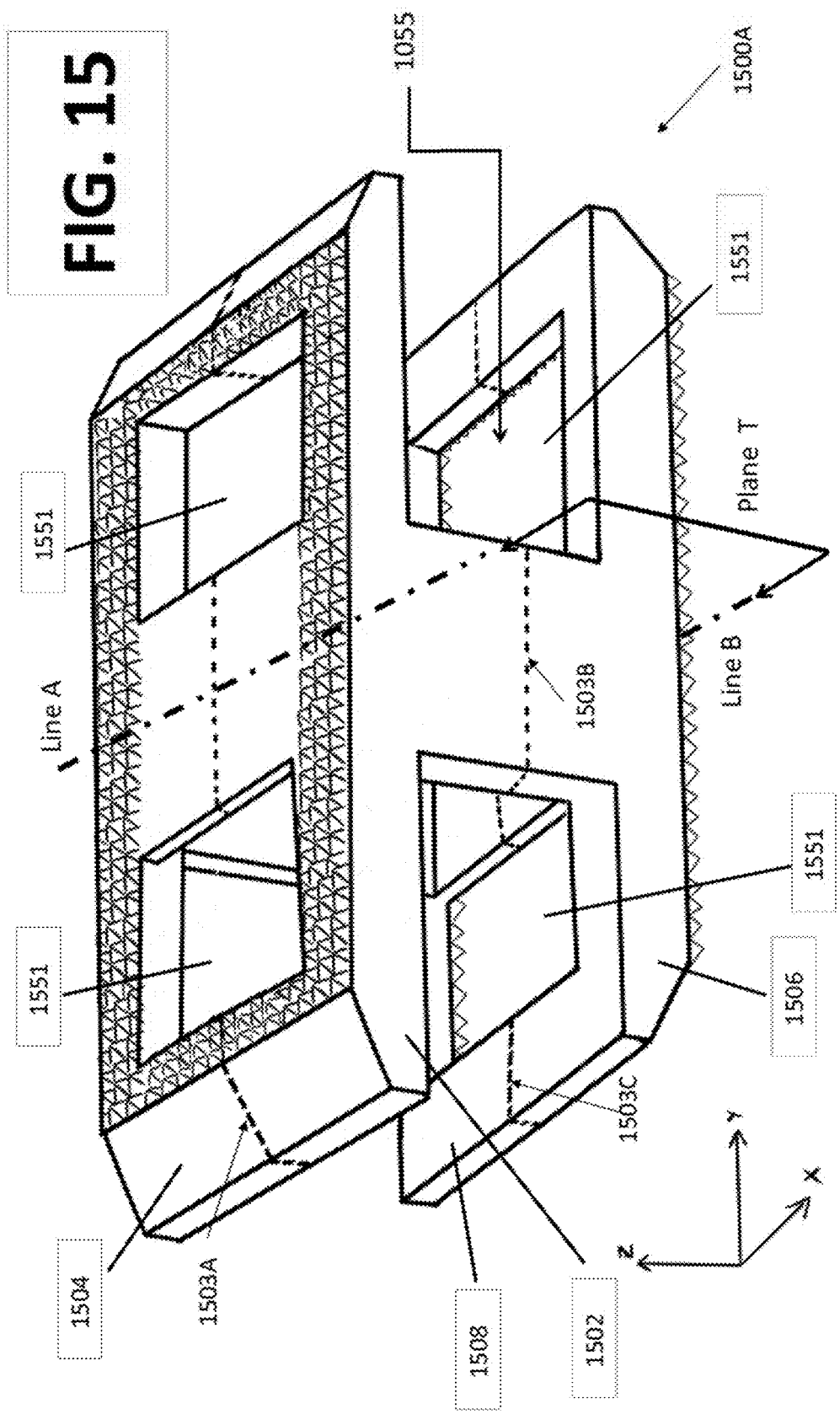
FIGS. 15-17 illustrate one embodiment of an implantable device housing, according to aspects of the present disclosure.
Figure 16:
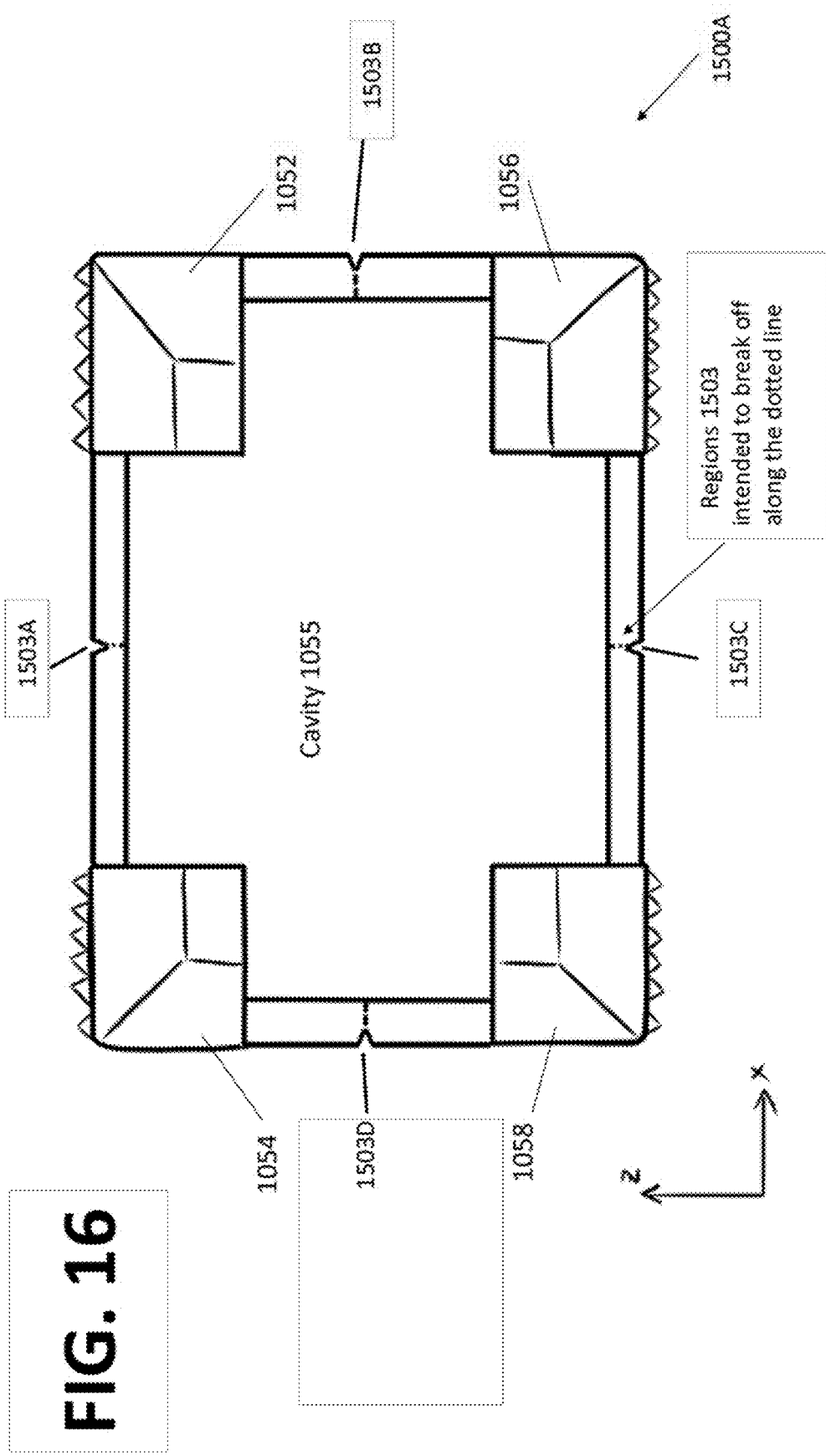
Figure 17:
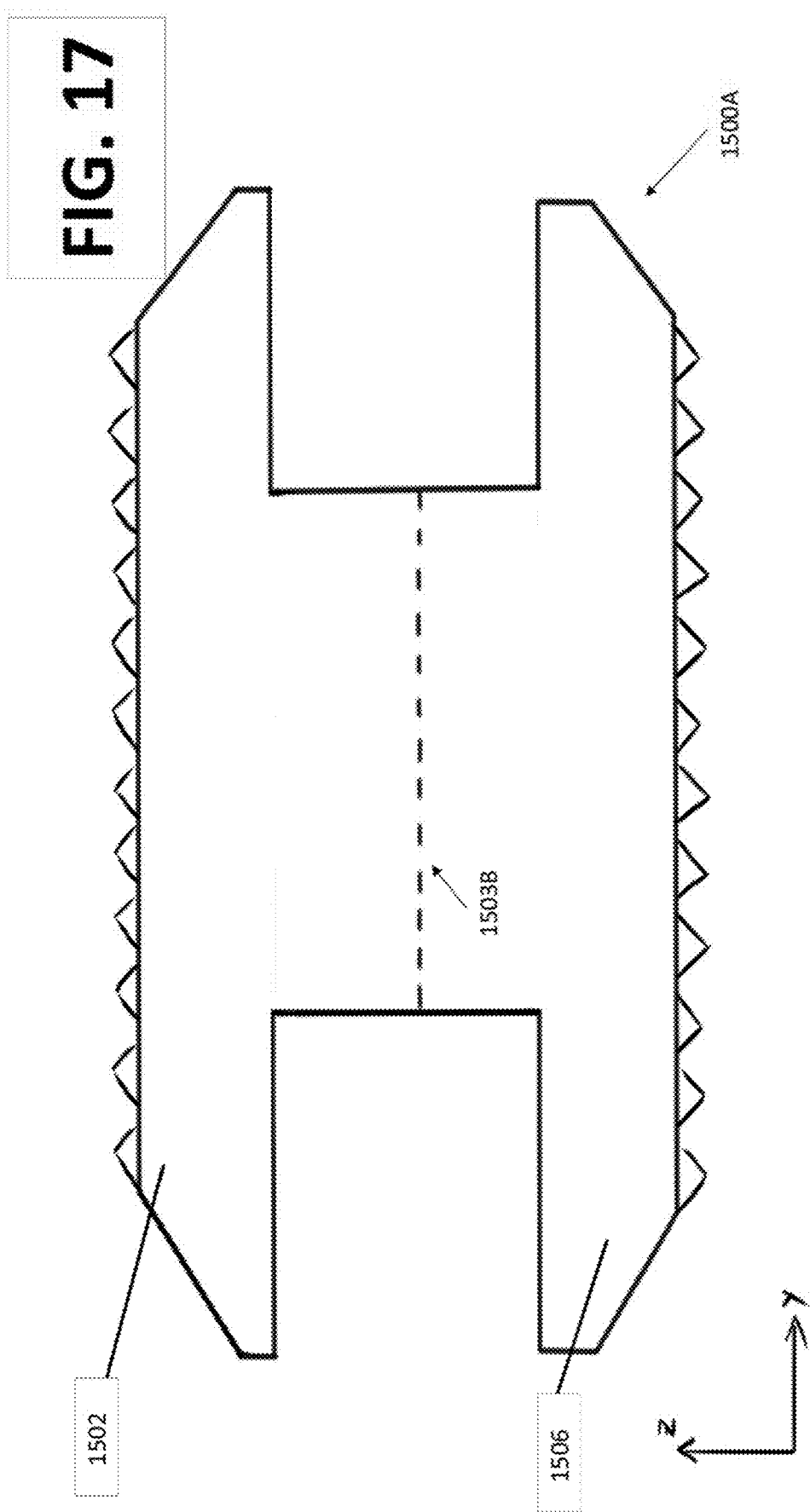

One exemplary embodiment of housing 1500A is illustrated in FIGS. 15-17. In an embodiment, the housing 1500A may be comprised of at least a first segment configured to at least abut an inferior aspect of the superior vertebral bone and second segment configured to at least abut a superior segment of the inferior vertebral bone. The housing 1500A of FIG. 15, for example, may comprise two segments 1502, 1504 that may be implanted to about the inferior aspect of the superior vertebral bone. It may also comprise two segments 1506 and 1508 that may be implanted to abut the superior aspect of the inferior vertebral bone. Housing 1500A is illustrated within an intervertebral disc space in FIG. 18.

A section through housing 1500A is shown in FIG. 6. The section is shown at plane T of FIG. 15. (Plane T is comprised of a plane containing parallel, but not co-linear, Line A and Line B.) Two or more of segments 1502, 1504, 1506 and 1508 may be held together during the advancement of housing 1500A into the target intervertebral disc space. After implantation, one or more segments may be detached from one another and/or distracted apart so that the overall surface area of the outer aspect of implant 1500A and/or the volume contained within the outer aspect of housing 1500A is enlarged after said detachment and/or distraction. This may be accomplished by increasing a distance between at least two segments of housing 1500A so as to increase the overall length, height and/or width of the housing 1500A.

The segments of 1502, 1504, 1506 and 1508 may be held together during the advancement of the housing 1500A into the target intervertebral disc space using any means known or yet to be known for holding the segments in proximity to one another during the step of implant advancement. These means include, but are not limited to, clips, friction members, screws/nuts, ratchets, tethers (whether malleable or non-malleable) and the like. In addition to, or instead of, a means for direct attachment to one another, the segments may be held together by their common attachment to a member outside of the housing 1500A itself—such as, for example, the placement instrument(s) used for advancing housing 1500A into the target intervertebral disc space.

In an embodiment, the segments of housing 1500A may be held together by one or more weakened regions 1503 (1503A/1503B/1503C/1503C shown in FIG. 16), as show in FIGS. 15 and 16. Four of the weakened regions 1503 are shown in FIG. 16. At least four more weakened regions 1503 in the housing 1500A are not shown in the cross section of FIG. 16. The weakened regions 1503 may comprise, for example, areas of decreased material thicknesses, as shown, and the thicknesses may be dimensioned to control the force at which the weakened regions 1503 break and the segments separate from one another. In addition to thickness, the force(s) needed to cause segment separation may be dependent on, among other factors, on the material from which housing 1500A is manufactured. The force(s) needed to cause segment separation may be pre-set at the time of manufacturing and the housing 1500A may be made and provided to the end-user (such as, for example, surgeon) in various embodiments from which the end user selects the implant that may best fit their need for the target disc space. It is contemplated that various break off segments within a single housing 1500A may be pre-set so as to require different force levels/thresholds to cause the different pairs of segments to separate. In one embodiment, the manufacturer may pre-set different force requirements for segment separation of housing 1500A members that are intended for use in different levels (cervical, thoracic and/or lumbar) of the spinal column. These features allow the end user (surgeon) to customize the housing 1500A to the anatomy of the target disc space. In one variant, the force level required for segment separation within a housing 1500A may be pre-set to allow a desired dimension (length, width and/or height) of the implant to preferentially enlarge to a greater extent than another dimension. In one variant, the force level required for segment separation may be re-set so as to produce a particular order of segment separation wherein, for example, the length, width and/or height are increased in a particular desired order.

For example, the housing 1500A can be configured such that a first force level/threshold is required to separate segments in a first direction and a second, greater force level is required to separate segments in a second direction. In one implementation, the housing 1500A may be configured to first separate along top and bottom weakened regions (from a first force level), and then separate along side weakened regions (from a second, greater force level). In another implementation, the housing 1500A is configured to separate along side weakened regions first (from a first force level) and top/bottom weakened regions second (from a second, greater force level). A surgeon may: (i) choose to expand the housing in only one direction (length, width, or height) by applying only a first level of force and not reaching the second level of force or (ii) choose to expand the housing in two directions (two of length, width, or height) in a predetermined order by increasing the applied force to the first level and then to the second level.

In one variant, the weakened regions 1503 are separated into two or more sets, such that weakened regions in the same set are configured to break at the same level of force. In one implementation, weakened regions formed along opposite sides of the housing are grouped in the same sets. In another implementation, weakened regions formed in adjacent sides of the housing are grouped in the same sets. In one implementation, each weakened region is configured to break at a different, predetermined level of force. This would allow the housing 1500A, for example, to expand into a wedge shape by breaking only one weakened region. In another example, two or more adjacent weakened regions of the housing 1500A could be separated, leading to a lopsided expanded housing.

In various exemplary embodiments of the disclosure, the weakened regions 1503 of the housing 1500A are located along central lines of housing 1500A (as shown in FIG. 16). In other embodiments, at least some of the weakened regions 1503 are located closer to some segments of the housing 1500A than others. In another embodiment of the disclosure, the weakened regions 1503 of the housing 1500A are formed along straight lines. In other embodiments, at least some of the weakened regions 1500 may be formed along curved lines. In one embodiment, the weakened regions 1503 are aligned to the sides of the housing 1500A (i.e., are parallel with one or more edges of the housing). In another embodiment, at least some of the weakened regions are formed at an acute or obtuse angle to at least one of the housing sides.

The second member of the implant 1500 may be used as a distraction member to separate the segments of housing 1500A. Alternatively, or in addition, the housing 1500A may be distracted by the (non-implanted) instrumentation used for the insertion of the housing 1500A at the target disc space. In an embodiment of the latter, the second member may be then used to retain the separated segments of housing 1500A in the desired position/configuration relative to one another after removal of the (non-implanted) instrumentation used for the insertion of the housing 1500A. Alternatively, the second member may be used to further distract the segments of housing 1500A so as to provide greater customization to the final implant configuration.

The second member may be of fixed dimensions or a it may comprise an expandable distraction member that may be actuated to assume different dimensions. Many embodiments of expandable distraction members are known in the art and these devices employ a host of differing mechanisms for device expansion. These mechanisms include, but are not limited to, mechanical linkages, wedges, pulleys, balloons, magnets, pistons and the like. US Pat. Application No. 2007/0093901, among others, describes the use of pistons in the manufacture of an expandable interbody implant.

Figure 21B:
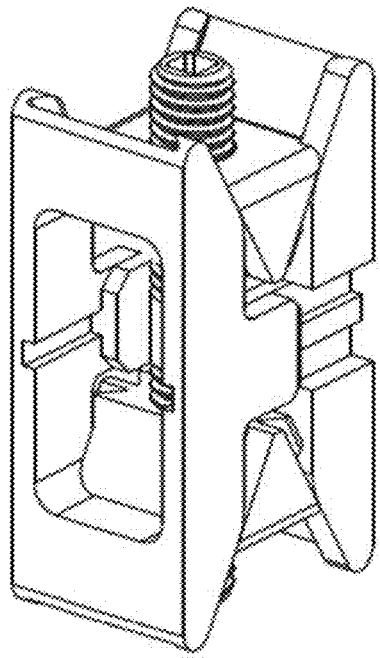
Figure 21A:
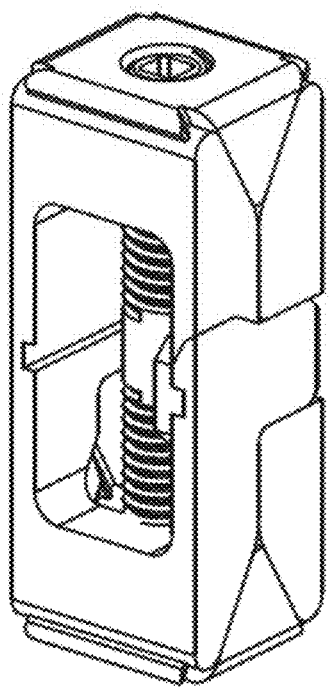
Figure 22:
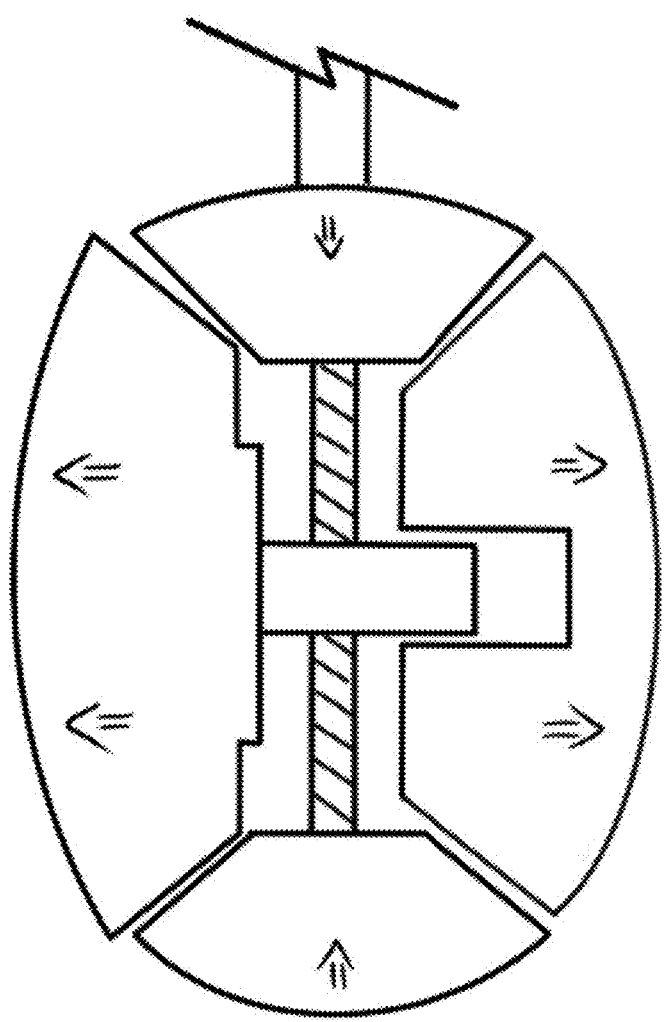

It is understood that any of the expandable distraction members recited above may be used. By way of non-limiting example, FIGS. 19 through 21 illustrate an example of a second member that comprises expandable distraction member 305. FIG. 19 shows a perspective view as well as three orthogonal views. An exploded view is shown in FIG. 20. A collapsed view is shown in FIG. 21A and an expanded view is shown in FIG. 21B. The expandable member 305 comprises wedge member 3052 (which may be similar or differing design, slop, size, etc), locking screw 3055 and abutment surfaces 3056 and 3058. A space 3059 may be contained at least partially in distraction member 305 and configured to house a bone forming substance so as to form a fusion between the vertebral bones superior to and inferior to the target disc space. FIG. 22 shows a schematic view of the distractive motion occurring within distraction member 305 by turning locking screw 3055 in a first direction. It is understood that rotation of screw 3055 in the first direction produces the distracted position shown in FIG. 21B, whereas rotation of screw 3055 in the opposite direction reverses the motion of FIG. 22 and returns member 305 to the collapsed configuration of FIG. 21A.

Figure 18:
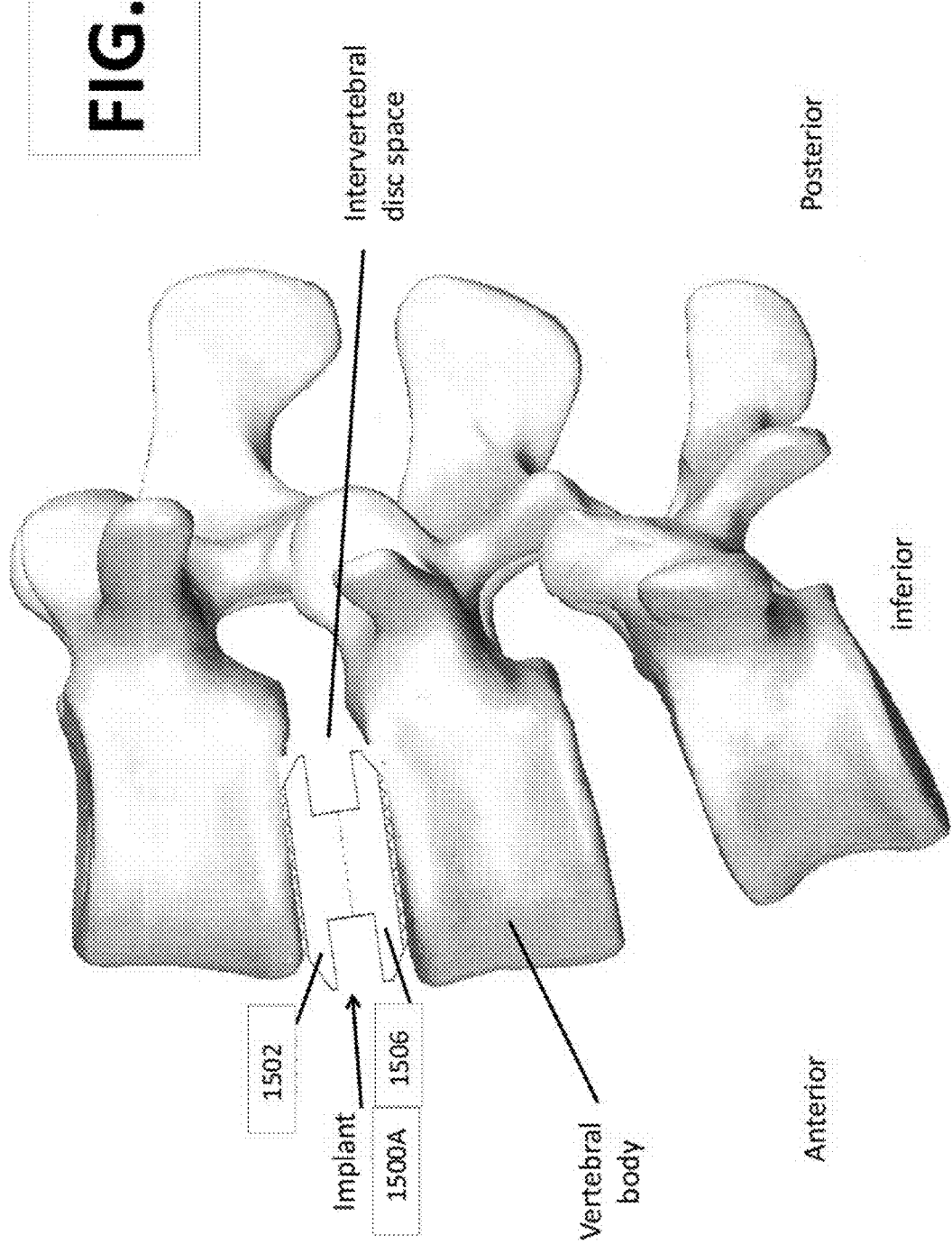
FIG. 18 illustrates a trajectory of approaching a space within a spinal column, according to aspects of the present disclosure.
Figure 23:
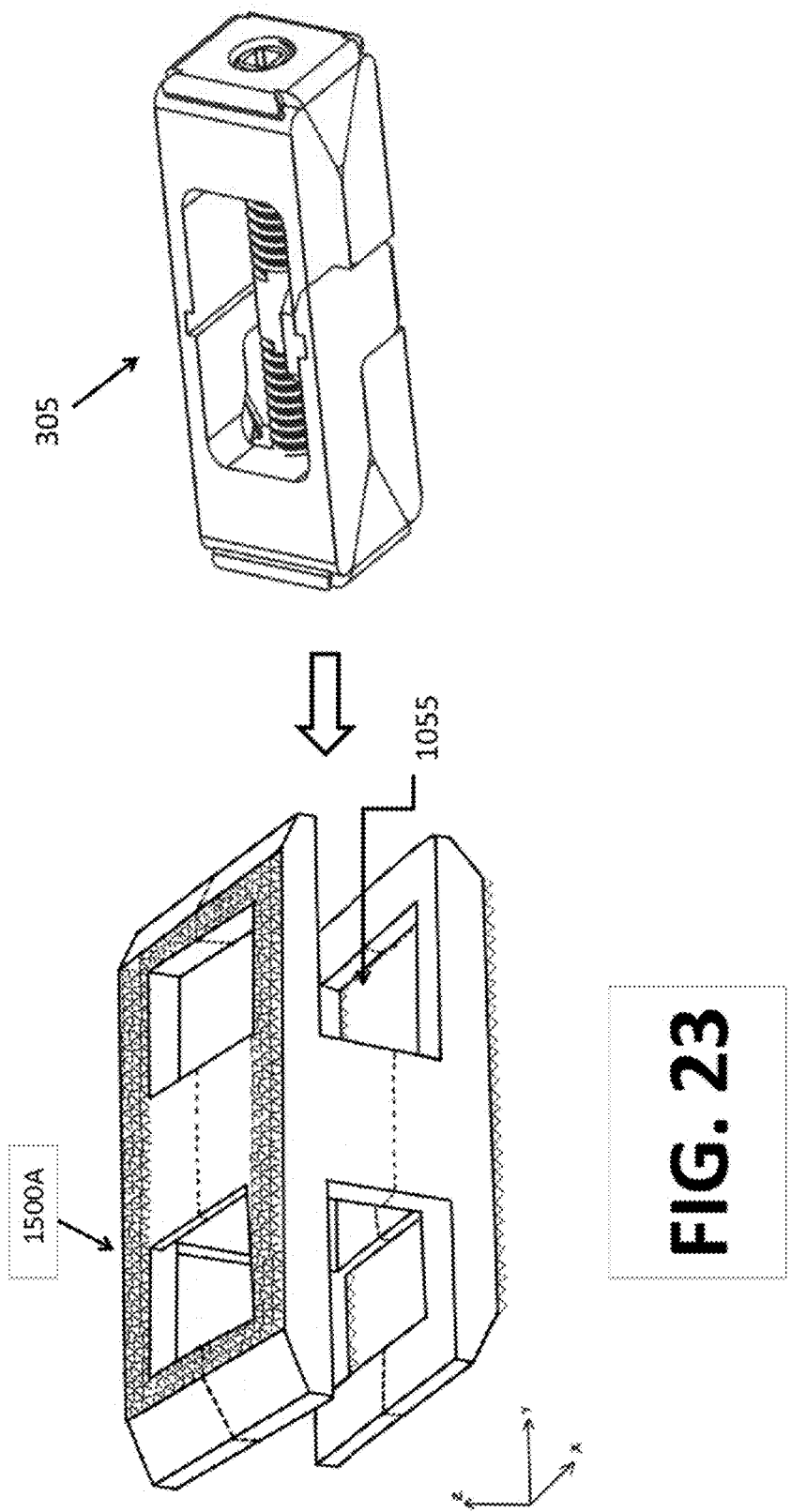
FIG. 23 illustrates an implantable device housing and distraction mechanism according to aspects of the present disclosure.

In use, housing 1500A is advanced into the target disc space as shown in FIG. 18. Distraction member 305 is then advanced into cavity 1055 of housing 1500A as show in FIG. 23. Member 305 may be advanced into cavity 1055 in the fully collapsed position. It may be of sufficiently small so as to exert insufficient force to separate the segments of housing 1500A during its advancement into cavity 1055. Alternatively, member 305 may be advanced into cavity 1055 in a partially distracted state so as to separate the segments of housing 1500A during its advancement into cavity 1055. In another embodiment, member 305 may by sufficiently large in the fully collapsed state so as to separate the segments of housing 1500A during its advancement into cavity 1055.

Figure 24B:
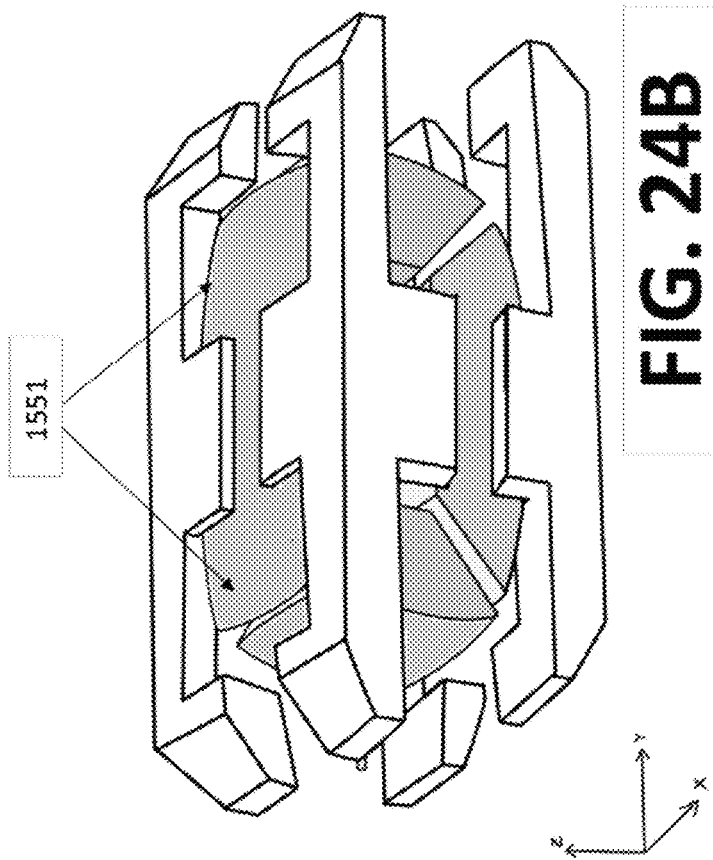
FIG. 24B illustrate an exemplary embodiment of an implantable device housing and distraction mechanism in a second expanded configuration.
Figure 24A:
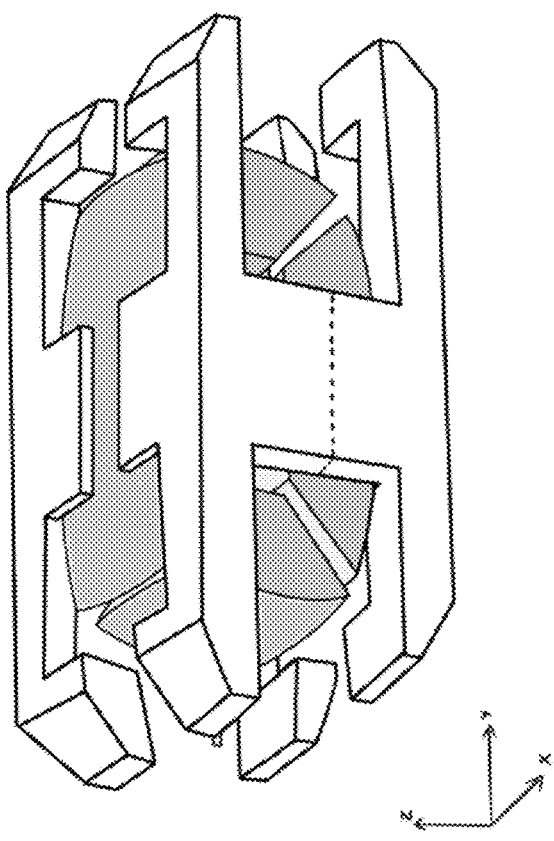
FIG. 24A illustrate an exemplary embodiment of an implantable device housing and distraction mechanism in a first expanded configuration.
Figure 25B:
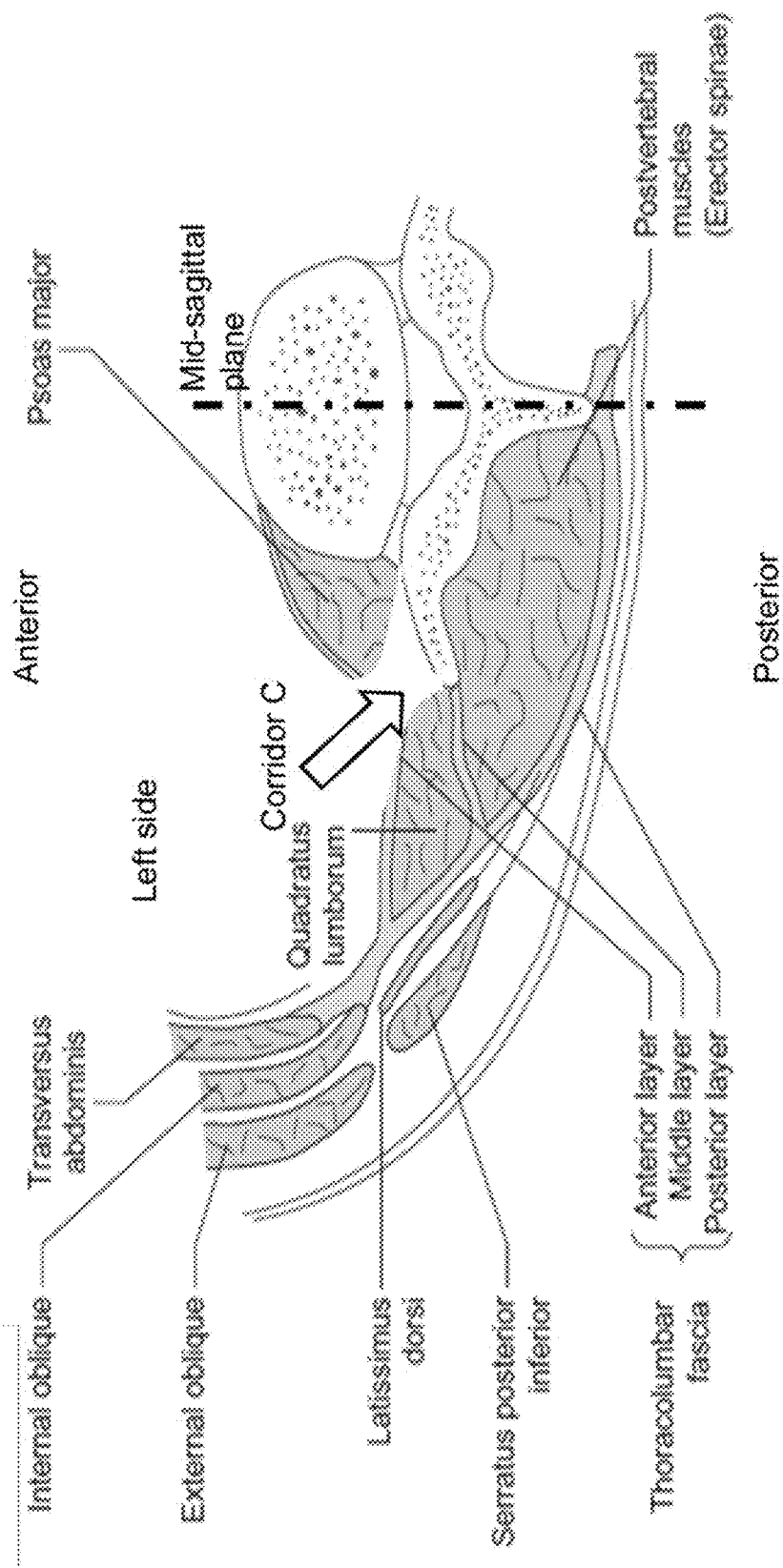

In an embodiment, after member 305 is seated within cavity of 1055 of housing 1500A, screw 3055 may be actuated to produce expansion of member 305 and provide sufficient force to break at least one region 1503 that had not been broken by the advancement of member 305 into cavity 1055. As discussed above, the specifics of which region 1503 is broken, and in what order, will depend on the specific design of the regions 1503. FIGS. 24A and 24B illustrate the breaking of different regions 1503. Finally, apertures 1551 allow the bone forming material to form a fusion across the housing 1500A and between the superior and inferior vertebral bones that surround the target disc space.

Vertebral Bone Fixation

Many surgeons employ bone screws or other fasters to immobilize the vertebral bones adjacent to the target disc space while the disc space heals and the bony fusion solidifies. These bone screws/fasters provide greater fixation when placed into the posterior aspect of the vertebral bones. Hence, when employing the posterior corridor (511) or the posterolateral corridor (513) (FIG. 14), the bone screws/fasters can be placed without the need for additional surgical exposure.

When using the intra-abdominal approaches (approach 505, 507 and 509), insertion of the bone screws/fasteners will require an additional surgical exposure to access the posterior elements of the vertebral bone. A novel approach has been developed wherein the same incision/corridor used for approach 505, 507 or 509 can be extended to access the posterior elements of the vertebral bone. In that approach, at least a portion of the surgical corridor (corridor C of FIG. 3) may be oriented so as to extend through the anterior layer of the thoracolumbar fascia. (A full description of the anatomy of the thoracolumbar fascia is contained in: The thoracolumbar fascia: anatomy, function and clinical considerations. Willard F H, et al. *J Anat.* 2012 December; 221(6): 507-536. The article is hereby incorporated by reference in its entirety.) Development of this surgical corridor (corridor C) is illustrated in FIGS. 3, 14 and 15. As shown, corridor C is developed between the posterior aspect of the ipsilateral Psoas Major and the anterior and medial aspect of the ipsilateral Quadratus Lumborum muscle. While corridor C is intended to substantially extend between these two muscles, it may contain at least a segment of each of them. Corridor C is thereby intended to be anterior to the anterior surface of the ipsilateral transverse process of the inferior vertebral bone of the target FSU and posterior to at least the posterior one half of the ipsilateral Psoas major muscle when the latter is measured in a sagittal plane that traverses it. In the superior lumbar spine, the Psoas is usually a small muscle and it increases in size as it extends inferiorly. In some segments of the spine, such as the thoracic spine, the Psoas major muscle is not present at all. Where the muscle is absent, it is understood that Corridor C is defined by its relationship to the ipsilateral transverse process and not by its relationship to the Psoas muscle.

Preferably, the anterior layer of the thoracolumbar fascia is traversed by corridor C. Dissection may be continued through corridor C in order to traverse coronal plane T in an anterior to posterior direction. In this way, the ipsilateral transverse processes of the vertebral bones of the target functional spinal unit may be reached. Similarly, segments of the target functional spinal unit that are positioned posterior to coronal plane T may be accessed through corridor C—as well be discussed further below.

If desired, the ipsilateral transverse process of either said superior or inferior vertebral bone of the target functional spinal unit may be removed through corridor C (FIGS. 26A and 26B). The harvested transverse process bone may be used as autograft bone for a fusion procedure that is concurrently performed at the same operation. That is, the preceding steps constitute a method for removal of a transverse process of said target functional spinal unit. In this method, an intra-abdominal (and, preferably, extra-peritoneal) surgical corridor is developed through a plane between the ipsilateral psoas major muscle and at least a segment of the ipsilateral quadratus lumborum muscle. The ipsilateral transverse process of one or both vertebral bones of the target functional spinal unit is removed. If desired, the removed transverse process may be used as a bone graft (i.e., autograft) material to fuse two or more skeletal bones of the individual during the same surgical procedure. Preferably, the harvested transverse process bone is incorporated into the bone graft that is used to fuse the superior vertebral bone to the inferior vertebral bone of said target functional spinal unit. That is, at least a portion of the bone graft that is used to fuse the superior to the inferior vertebral bones (by positioning a segment of the bone graft to abut the superior vertebrate bone and a segment to abut the inferior vertebral bone) is comprised of bone derived from the harvested transverse process.

At least a portion of the harvested transverse process bone may be preferably, but not necessarily, placed into the target intervertebral disc space in order to form an interbody fusion within the target functional spinal unit. Further, bone graft material (whether containing autograft bone, allograft bone, a synthetic material, or any other substance adapted to form bone) may be placed to extend along the longitudinal axis of the spine from the lateral aspect of the superior articular process (SAP) of the superior vertebral bone to the superior articular process (SAP) of the inferior vertebral bones of the target functional spinal unit. The bone graft material will eventually form a fusion mass that connects the SAP and transverse processes (or the remaining stump thereof) of adjacent vertebral bones (FIG. 26B).

Figure 27:
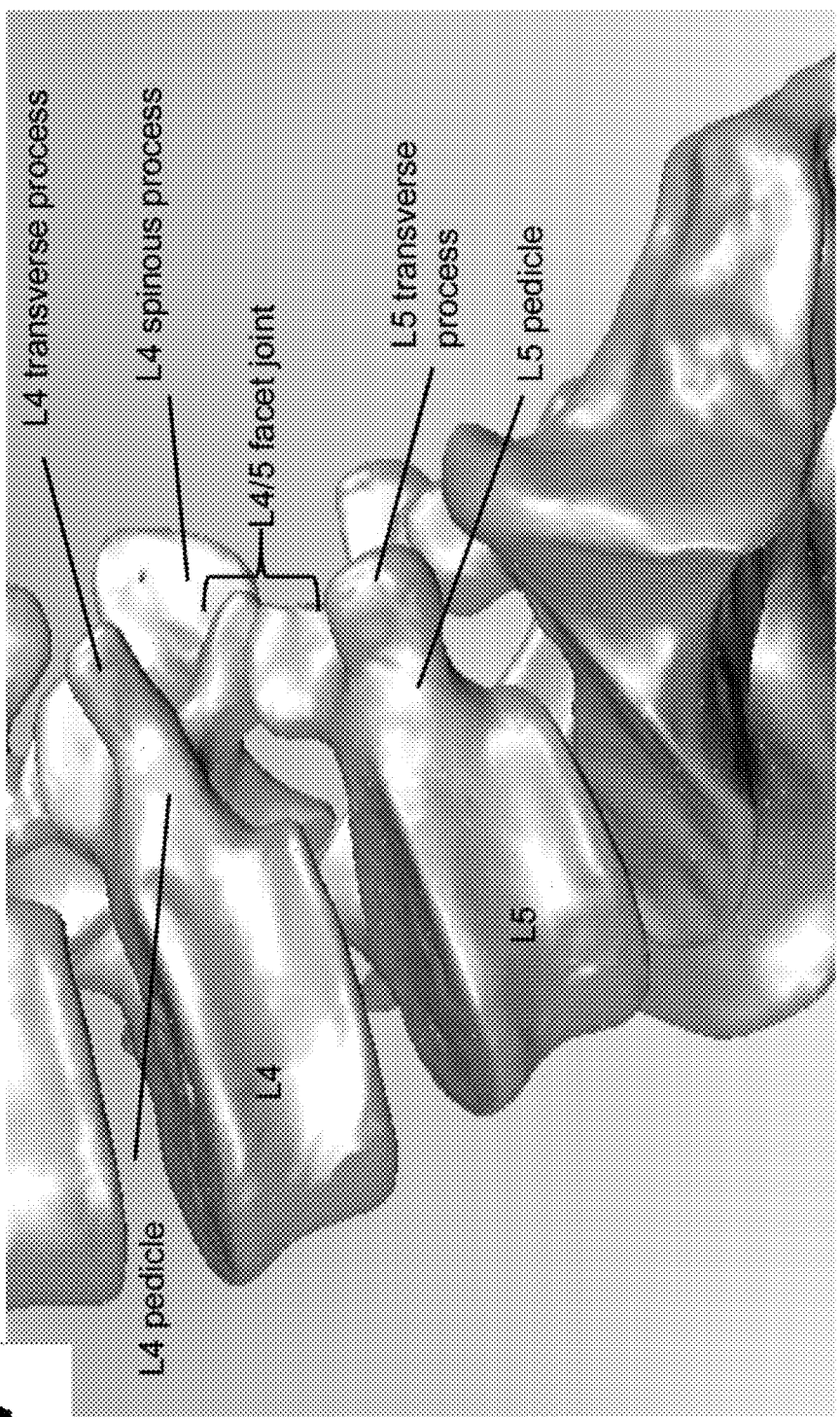
FIG. 27 illustrates a vertebral column.
Figure 28:
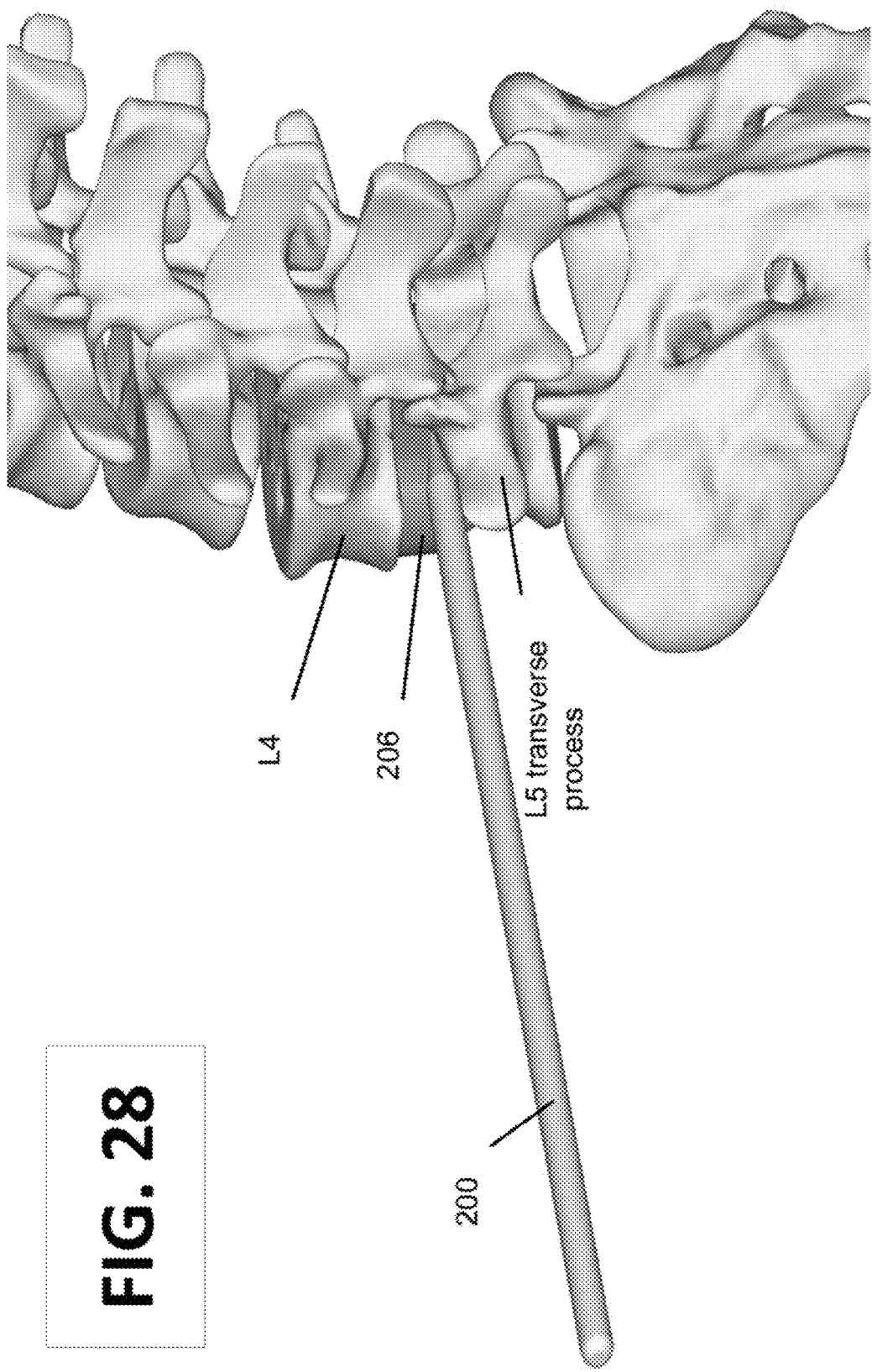

A facet joint, by definition, is an articulation comprised of the superior articulating process (SAP) of an inferior vertebral bone and the inferior articulating process (IAP) of the immediately superior vertebral bone. In the target functional spinal unit, a right and a left facet joints form articulations between the superior and inferior vertebral bone—with a single facet joint on each side of the mid sagittal plane of the vertebral column (FIG. 27). Using corridor C to reach the ipsilateral transverse process, as described above, the ipsilateral facet joint (ipsilateral to said skin incision) can be also accessed. Preferably, but not necessarily, the ipsilateral transverse process of the inferior vertebral bone of the target functional spinal unit is removed in order to provide a wider corridor through which to access said ipsilateral facet joint. However, it is understood that the transverse process may be left in place or only partially removed and the ipsilateral facet joint accessed around it. When the transverse process is not fully removed, the facet joint is preferably accessed through an anterior to posterior trajectory that passes superior to said ipsilateral transverse process of the inferior vertebral bone—as shown in FIGS. 28 and 29. The trajectory used to access the ipsilateral facet joint via corridor C will necessarily cross coronal plane T in an anterior to posterior trajectory (FIG. 29) and will substantially follow member 200. Note that the tip of member 200 is positioned at the lateral surface of the SAP of the inferior vertebral bone of the target FSU.

The preceding steps constitute a method to access the ipsilateral facet joint between the superior and inferior vertebral bones of a target functional spinal unit. Once accessed, the ipsilateral facet joint may be at least partially removed, if desired, to decompress the nerve elements. The joint, whether whole or after partial resection, may be also implanted with fastener(s) that serve to limit and/or completely immobilize movement between the said superior and inferior vertebral bones, as will be further illustrated below.

Figure 30B:
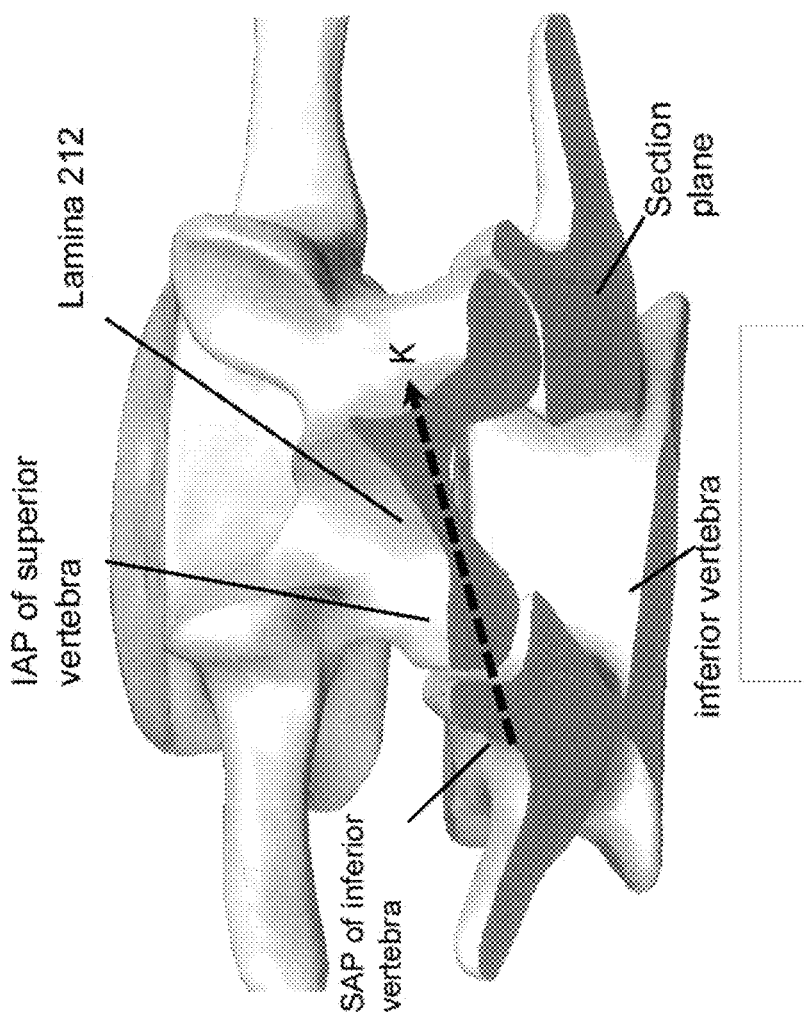
FIGS. 30A-30B illustrate an exemplary way of approaching a facet space, according to aspects of the present disclosure.
Figure 30A:
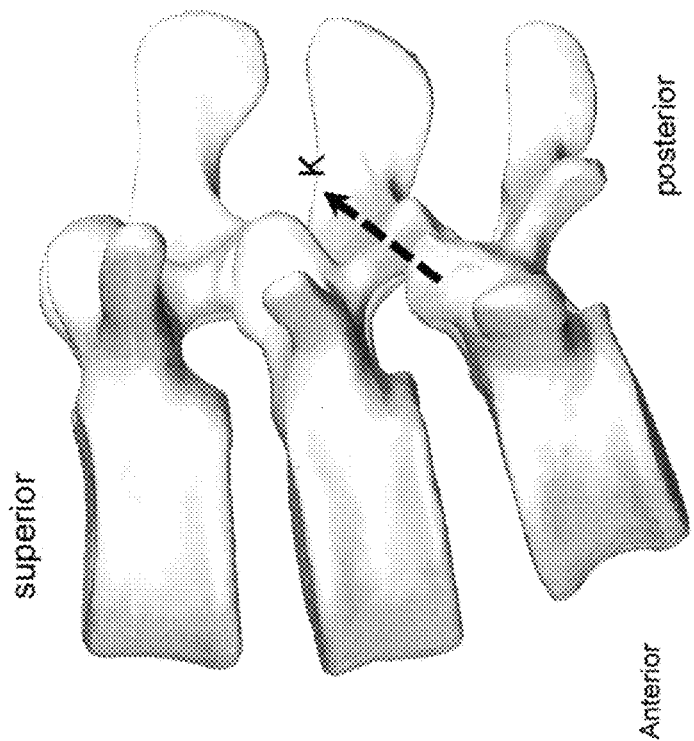
Figure 31B:
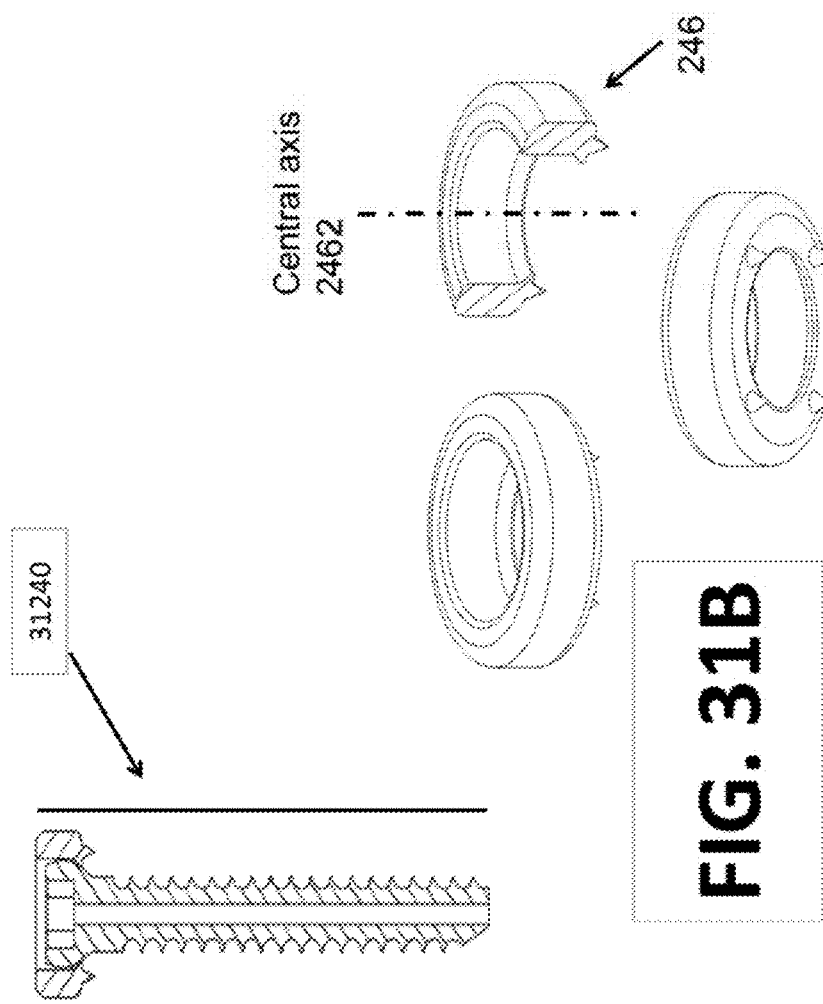
FIGS. 31A-31B illustrate an exemplary embodiment of screw/nut components that may be used with the implantable device of the present disclosure.
Figure 31A:
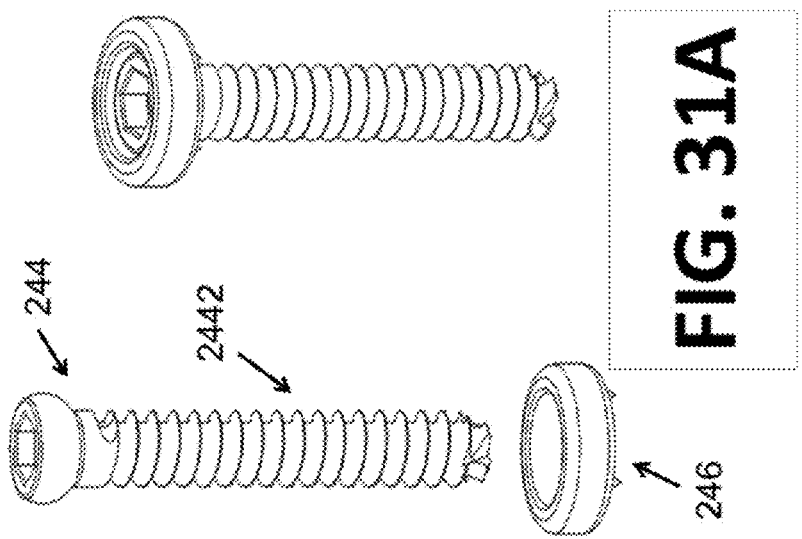

After the ipsilateral facet is accessed through corridor C, a fastener may be placed into the ipsilateral facet joint in order to immobilize the movement between the superior and inferior vertebral bones across said joint. Following a lateral to medial trajectory (such as, for example, the trajectory of member 200), the fastener may be passed through the lateral aspect of the SAP of the inferior vertebral bone, across the facet joint space and into the IAP of the superior vertebral bone—as shown by arrow K in FIGS. 30A and 30B. Note that the fastener may be further passed into the ipsilateral lamina 212 of the superior vertebra as shown in FIG. 30B. FIG. 30B illustrates sectional view passing through the facet joints between the L3 and L4 vertebral bones. The plane of the sectional view is shown by the anterior-posterior direction of arrow K of FIG. 30A. The lateral-medial direction of arrow is shown in FIG. 30B.

The disclosed device embodiments or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as, for example, porous titanium, titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. The system or any of its components may be made by "additive manufacturing", such as, for example, "3D" printing. Lastly, the system or any of its components can also be entirely or partially made of a shape memory material or other deformable material.

Methods

One embodiment of a method of use for the implant assemblies disclosed herein includes inserting an implant assembly into the target intervertebral disc space using any desired surgical approach to the spine (such as those described supra). The assembly comprises a first (host) member and a second member comprising a distraction mechanism. The first member comprises at least a first and a second segment that are configured to move relative to one another, wherein, for example, movement of the first segment relative to the second segment apart increases a height, a length, and/or a width of the first member. Preferably, but not necessarily, the first member does not comprise its own distraction mechanism; however in some examples, the first member may comprise an integral distraction mechanism. In one variant, the method further includes anchoring one of upper and lower elements of the first member to one of the superior and inferior vertebral bones of the target FSU (such as, for example, by via a first bone screw). Further, the method may include anchoring the other of the upper and lower elements of the first member to the other of the superior and inferior vertebral bones of the target FSU (such as, for example, by via a second bone screw).

The method further includes actuating the distraction mechanism after positioning of the implant assembly at the desired location within the target disc space. The first member and the second member are coupled such the act of actuating of the distraction mechanism (the second member) causes a distance between the upper and lower elements to increase on at least one end or side of the first member. Additionally, a distance between one or more portions of the upper and lower elements may decrease, and/or both ends a distance between the upper and lower elements at both ends of the first member may increase. For example, the upper and lower elements the first member to move away from (or towards) one another. In another example, one of the upper and lower elements may move away from (or towards) the other of the upper and lower elements. In this way, the act of actuating of the distraction mechanism of the second member increases at least one of the height, length, and/or width dimensions of the implant assembly and alters the distance between the superior and inferior bones within at least one plane (coronal, axial, and/or sagittal planes) of the spine.

Alternate Configurations

It is appreciated that while the foregoing description describes an implant device 104 that may have one side (but not the other) increased in height, the present disclosure contemplates alternate implant configurations which have more degrees of freedom. For instance, in one such configuration, both sides of the implant can be adjusted as to height, whether increased or decreased, so as to obtain an optimal relative height/size profile for the target space. In one such implementation (not shown), rather than being hinged as shown in FIGS. 6A and 6B, the pivot or axes of rotation of the implant upper and lower segments is disposed more centrally to the implant 104, such that the two sides of the implant can "toggle" or alternate.

In yet another implementation, both sides of the implant can increase or decrease in tandem with one another, such as via use of a hinge or pivot that is centrally located on the implant, yet which can also translate in a direction normal to the plane of the implant device (i.e., such that the upper and lower elements 1051*a*, 1051*b* can move closer or further apart from one another, while also having different heights if desired.

In such configurations, more than one distraction member 205 may also be utilized, such as where one distraction member is disposed at or near each end (side) of the implant device.

Once the desired configuration is achieved, the translation mechanism (e.g., a set screw or other mechanism) can be fastened and locked so as to make the configuration effectively permanent (at least during the lifetime of the implantation). Adhesives or yet other means for maintaining the desired position can be utilized as well. In one variant, the distraction mechanism can be removed after fastening or locking of the first member of the desired position.

In another embodiment for the variable height implant, the implantable device comprises at least two members, the first being a body (which may comprise more than one segment) configured to abut each of the superior and inferior vertebral bones of the target FSU containing the target intervertebral disc space. In one implementation, the first member is comprised of a solid material, which may further be malleable so as to facilitate conformance with at least portions of the target space, and is adapted for implantation into the subject. In another implementation, the first member may be at least partially comprised of a balloon or variable-geometry inflatable bladder. The second member comprises a distraction mechanism that provides the force needed to increase the height of one or both lateral sides of the implant, as well as the structure to maintain the increased height of the implant. In one variant, the distraction mechanism comprises a separate member that can be reversibly inserted/coupled onto the first member by the operator at the time of the surgical procedure.

In another variant, the second member is permanently attached to or integrally formed with the first member. In one implementation, the mechanism comprises an actuatable mechanical device, such as a hydraulic piston. In another implementation, the mechanism is at least partially comprised of a balloon.

In still another embodiment, the implant device is a kit comprised of at least the first and second members. In one implementation, the first and second members can be used alone or in combination depending on the specific condition or configuration of a spine of a patient.

The disclosed device embodiments or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like.

Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation.

Further, any surface may be made with a porous ingrowth surface (such as, for example, porous titanium, titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. The system or any of its components may be made by "additive manufacturing", such as, for example, "3D" printing.

Lastly, the system or any of its components can also be entirely or partially made of a shape memory material or other deformable material.

While this specification contains certain specific features and attributes, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

It will also be recognized that while certain aspects of the disclosure are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure disclosed and claimed herein.

What is claimed is:

1. A modular device assembly configured to be at least partially seated within an intervertebral disc space, the intervertebral disc space disposed between a superior vertebral bone and an adjacent inferior vertebral bone, the modular device assembly comprising:

a receiving member comprising:
   a first top surface; and
   a first opposing bottom surface movably coupled with the first top surface, the first top surface and the first opposing bottom surface of the receiving member cooperatively configured to reversibly receive a distraction module therebetween, the distraction module comprising:
      a second top surface;
      a second opposing bottom surface configured to be movable relative to the second top surface; and
      an actuator configured to receive a non-implantable driver and actuate the second top surface of the distraction module relative to the second opposing bottom surface of the distraction module;

wherein the distraction module is configured to cause upon actuation:
    displacement of the second top surface of the distraction module away from the second opposing bottom surface of the distraction module; and
    an increase of a distance between at least a portion of the first top surface and at least a portion of the first opposing bottom surface of the receiving member; and
wherein the distraction module is further configured to be received by the receiving member as a unitary assembly.

2. The modular device assembly of claim 1, wherein the first top surface comprises one or more surface features configured to facilitate fixation onto bone.

3. The modular device assembly of claim 1, wherein the modular device assembly is devoid of a distraction module other than the distraction module contained within the distraction module.

4. The modular device assembly of claim 1, wherein the receiving member further comprises a locking mechanism configured to immobilize the first top surface relative to the first opposing bottom surface.

5. The modular device assembly of claim 1, wherein the second top surface of the distraction module further comprises one or more features configured to promote fixation onto bone.

6. The modular device assembly of claim 1, wherein the distraction module further comprises two or more actuators.

7. The modular device assembly of claim 1, wherein the receiving member further comprises a hinge segment configured to effectuate the movably coupling of the first top surface with the first opposing bottom surface.

8. The modular device assembly of claim 1, wherein the distraction module of the distraction module is devoid of gear engagement.

9. A modular device assembly configured for implantation within an intervertebral disc space, the intervertebral disc space disposed between a superior vertebral bone and an adjacent inferior vertebral bone, the modular device assembly comprising:
    a housing member comprising:
        a first top surface; and
        a first bottom surface opposing at least a portion of the first top surface, the first top surface configured to be movable relative to the first bottom surface; and
    a unitary distraction module comprising:
        a second top surface;
        a second bottom surface opposing at least a portion of the second top surface, the second top surface configured to be movable relative to the second bottom surface; and
        a distraction mechanism that is configured to cause, upon actuation, (i) displacement of the second top surface away from the second bottom surface, and (ii) an increase of a distance between the first top surface and the first bottom surface, the displacement and the increase being concurrent with each other;
    wherein:
        the modular device assembly further comprises an axis extending from the first top surface to the first bottom surface and through at least a portion of the distraction mechanism of the unitary distraction module; and
        the distraction mechanism is configured to, upon actuation, be devoid of rotational movement centered about the axis.

10. The modular device assembly of claim 9, wherein the first top surface of the housing member comprises one or more surface features configured to increase fixation into bone as compared to the first top surface without the one or more surface features.

11. The modular device assembly of claim 9, wherein the modular device assembly is configured to utilize no distraction mechanism other than the unitary distraction module.

12. The modular device assembly of claim 9, wherein the receiving member further comprises a locking mechanism configured to immobilize the first top surface relative to the first bottom surface.

13. The modular device assembly of claim 9, wherein the second top surface of the unitary distraction module further comprises one or more features configured to promote fixation into bone.

14. The modular device assembly of claim 9, wherein the unitary distraction module further comprises at least one feature that is configured to, when directly coupled with a non-implantable driver, cause actuation of the unitary distraction mechanism.

15. The modular device assembly of claim 9, wherein the receiving member further comprises a hinge element configured to movably couple the first top surface and the first bottom surface.

16. The modular device assembly of claim 9, wherein the distraction mechanism of the unitary distraction module is configured to be actuated utilizing only non-gear based apparatus.

17. A modular device assembly configured for implantation within an intervertebral disc space, the intervertebral disc space disposed between a superior vertebral bone and an adjacent inferior vertebral bone, the modular device assembly comprising:
    a housing member comprising:
        a first surface;
        a second surface opposing at least a portion of the first surface, the first surface movably coupled with the second surface; and
        a coupler configured to reversibly receive at least one unitary distraction module; and
    the at least one unitary distraction module, the at least one unitary distraction module comprising:
        a third surface;
        a fourth surface opposing at least a portion of the third surface, the third surface configured to be movable relative to the fourth surface; and
        a distraction mechanism that is configured to cause, upon actuation, displacement of the third surface away from the fourth surface, and an increase of a distance between the first surface and the second surface; and
    wherein the distraction mechanism is configured to be devoid of gear engagement along an axis extending from the first surface to the second surface and at least partly through the distraction mechanism of the distraction module.

18. The modular device assembly of claim 17, wherein the first surface comprises a surface having one or more features configured to promote fixation onto bone.

19. The modular device assembly of claim 17, wherein:
    the axis comprises an at least approximately vertical axis;
    the first and second surfaces comprise upper and lower surfaces, respectively;
    the third and fourth surfaces comprise upper and lower surfaces, respectively; and the modular device assembly consists of a single distraction mechanism.

20. The modular device assembly of claim 17, wherein the housing member further comprises a locking mechanism configured to fix a position of the first surface relative to a position of the second surface.

21. The modular device assembly of claim 17, wherein the third surface further comprises one or more features configured to promote fixation onto bone.

22. The modular device assembly of claim 17, wherein the unitary distraction module comprises a feature that is configured to, while coupled to a user-guided driver apparatus, actuate the distraction mechanism.

23. The modular device assembly of claim 17, wherein the receiving member further comprises a jointed element configured to movably couple the first surface and the second surface.

24. The modular device assembly of claim 17, wherein:
the unitary distraction module further comprises a notch portion;
the housing member further comprises a cutout portion corresponding to the notch portion of the unitary distraction module; and
the notch portion and the cutout portions are configured to cooperatively prevent rotational movement about a second axis, the second axis being substantially orthogonal to the axis extending from the first surface to the second surface.

25. A method for the treatment of a functional spinal unit of a subject, the functional spinal unit extending along a longitudinal axis of the subject and comprising a superior vertebral bone, an inferior vertebral bone and an intervertebral disc space positioned at least partly between the superior vertebral bone and the inferior vertebral bone, the method comprising:
approaching at least one side surface of the intervertebral disc space, the at least one side surface comprising an anterior side surface, a posterior side surface, a first lateral side surface, or an opposing second lateral side surface;
selecting a component of a modular implant assembly based on an assessment of a dimension of the intervertebral disc space, the selected components comprising:
a receiving member, the receiving member comprising (i) a first top surface, (ii) a first opposing bottom surface, (iii) a first side surface comprising a malleable member configured to movably couple the first top surface and the first opposing bottom surface, and (iv) a first cavity configured to at least partially seat a distraction module;
the distraction module being separately formed from the receiving member and comprising: (i) a second top surface configured to couple with the first top surface and (ii) a second opposing bottom surface configured to couple with the first opposing bottom surface;
advancing the receiving member into the intervertebral disc space, and positioning the first top surface to abut an inferior surface of the superior vertebral bone and the first opposing bottom surface to abut a superior surface of the inferior vertebral bone;
advancing the distraction module into the first cavity of the receiving member, the advancing of the distraction module being accompanied by an increase in a first vertical distance, as measured along the direction of the longitudinal axis of the subject, between a segment of the first top surface and a segment of the second opposing bottom surface; and
positioning a bone forming material at least partially within the receiving member, the bone forming material positioned to extend from the inferior surface of the superior vertebral bone to the superior surface of the inferior vertebral bone.

26. The method of claim 25, wherein the first side surface of the receiving member is integrally formed.

27. The method of claim 25, further comprising at least partially positioning the distraction module outside of the first cavity during the advancing of the receiving member into the intervertebral disc space.

28. The method of claim 25, further comprising at least partially positioning the distraction module outside of the intervertebral disc space during the advancing of the receiving member into the intervertebral disc space.

29. The method of claim 25, wherein the advancing of the distraction module into the first cavity of the receiving member increases a vertical height of a first side surface of the modular implant assembly by a greater distance than an opposing second side surface of the modular implant assembly, the vertical height measured along the direction of the longitudinal axis of the subject.

30. The method of claim 29, further enabling the modular implant assembly to assume a wedge-like configuration after the advancing of the distraction module into the first cavity of the receiving member.

31. The method of claim 25, wherein, prior to the advancing of the distraction module into the first cavity, the receiving member is devoid of a mechanism for the distraction of the first top surface away from the first opposing bottom surface.

32. The method of claim 25, wherein the distraction module further comprises:
(i) a distraction mechanism configured to cause, upon actuation, displacement of the second top surface away from the second opposing bottom surface of the distraction module; and
(ii) an actuator configured to couple with a non-implantable driver and enable said actuation of the distraction mechanism.

33. The method of claim 32, further comprising using the actuator to actuate the distraction mechanism, the actuating of the distraction mechanism increasing a vertical distance as measured along the direction of the longitudinal axis of the subject, between the second top surface and the second opposing bottom surface.

34. The method of claim 33, wherein the actuating of the distraction mechanism produces a further increase in a vertical distance, as measured along the direction of the longitudinal axis of the subject, between the first top surface and the first opposing bottom surface of the receiving member.

35. The method of claim 25, wherein the receiving member further comprises at least one physical feature configured to retain the distraction member therein.

36. The method of claim 25, wherein the first cavity is configured to receive the bone forming material, the first cavity comprising at least one aperture configured to open onto at least one of the superior vertebral bone or the inferior vertebral bone.

* * * * *